United States Patent
Tafesse et al.

(10) Patent No.: US 9,828,348 B2
(45) Date of Patent: Nov. 28, 2017

(54) BENZIMIDAZOLE DERIVATIVES AND USE THEREOF

(71) Applicant: Purdue Pharma L.P., Stamford, CT (US)

(72) Inventors: Laykea Tafesse, Robbinsville, NJ (US); Jiangchao Yao, Princeton, NJ (US); Xiaoming Zhou, Plainsboro, NJ (US)

(73) Assignee: Purdue Pharma L.P., Stamford, CT (US)

( * ) Notice: Subject to any disclaimer, the term of this patent is extended or adjusted under 35 U.S.C. 154(b) by 0 days.

(21) Appl. No.: 14/534,257

(22) Filed: Nov. 6, 2014

(65) Prior Publication Data

US 2015/0133500 A1    May 14, 2015

Related U.S. Application Data

(60) Provisional application No. 61/901,507, filed on Nov. 8, 2013.

(51) Int. Cl.

| | |
|---|---|
| *A61K 31/454* | (2006.01) |
| *C07D 401/04* | (2006.01) |
| *C07D 235/14* | (2006.01) |
| *C07D 403/06* | (2006.01) |
| *C07D 405/04* | (2006.01) |
| *C07D 403/04* | (2006.01) |

(52) U.S. Cl.
CPC ......... *C07D 235/14* (2013.01); *C07D 401/04* (2013.01); *C07D 403/04* (2013.01); *C07D 403/06* (2013.01); *C07D 405/04* (2013.01)

(58) Field of Classification Search
CPC ... C07D 401/04; C07D 403/04; C07D 405/04
USPC .......................................... 514/322; 546/199
See application file for complete search history.

(56) References Cited

U.S. PATENT DOCUMENTS

| | | | |
|---|---|---|---|
| 2,878,248 A | 3/1959 | Crounse | |
| 3,271,249 A | 9/1966 | Clegg et al. | |
| 3,549,754 A * | 12/1970 | Egerton et al. ............ | 514/224.8 |
| 5,210,091 A * | 5/1993 | Axelsson ............ | C07D 235/30 |
| | | | 514/322 |
| 6,281,211 B1 | 8/2001 | Cai et al. | |
| 6,335,354 B2 | 1/2002 | Hogenkamp | |
| 6,414,011 B1 | 7/2002 | Hogenkamp et al. | |
| 6,479,484 B1 | 11/2002 | Lan et al. | |
| 6,500,825 B2 | 12/2002 | Lan et al. | |
| 6,613,803 B1 | 9/2003 | Wang et al. | |
| 6,638,947 B2 | 10/2003 | Wang et al. | |
| 6,696,442 B2 | 2/2004 | Wang et al. | |
| 6,737,418 B2 | 5/2004 | Hogenkamp et al. | |
| 6,770,661 B2 | 8/2004 | Shao et al. | |
| 6,867,210 B2 | 3/2005 | Hogenkamp et al. | |
| 6,919,363 B2 | 7/2005 | Hogenkamp et al. | |
| 7,022,714 B2 | 4/2006 | Sun et al. | |
| 7,078,426 B2 | 7/2006 | Hogenkamp et al. | |
| 7,091,210 B2 | 8/2006 | Lan et al. | |
| 7,160,879 B2 * | 1/2007 | DeSimone ........... | C07D 235/14 |
| | | | 514/218 |
| 7,169,782 B2 | 1/2007 | Sun et al. | |
| 7,202,232 B2 | 4/2007 | Chen et al. | |
| 7,229,993 B2 | 6/2007 | Goehring et al. | |
| 7,393,872 B2 | 7/2008 | Lan | |
| 7,541,465 B2 | 6/2009 | Lan et al. | |
| 7,872,127 B2 | 1/2011 | Lan et al. | |
| 8,426,431 B2 | 4/2013 | Lan et al. | |
| 8,524,756 B2 | 9/2013 | Chen et al. | |
| 8,609,696 B2 | 12/2013 | Cogan et al. | |
| 8,796,280 B2 | 8/2014 | Page et al. | |
| 8,945,724 B2 | 2/2015 | Yamamoto et al. | |
| 9,168,255 B2 | 10/2015 | Goehring et al. | |

(Continued)

FOREIGN PATENT DOCUMENTS

| | | |
|---|---|---|
| GB | 2263637 A | 8/1993 |
| WO | 91/013063 | 9/1991 |

(Continued)

OTHER PUBLICATIONS

DiNetta et al. CA RN 3367-02-0.*
Axelsson et al. "Preparation of benz . . . " CA118:191736.*
Das et al. "Preparation of substituted . . . " CA157:548642.*
Walensky et al. "Small molecules for . . . " CA155:291909.*
Vlahakis et al. "Selective inhibition . . . " Bioorg. Med. Chemm. vo. 21, p. 6788-95 (2013).*
Axelsson et al. "Preparation of . . . " CA118:191736 (1993).*
Improper Markush, Fed. Reg. 76(27) p. 7162-7175, slide 1, 64-67 (2011).*

(Continued)

*Primary Examiner* — Charanjit Aulakh
(74) *Attorney, Agent, or Firm* — Purdue Pharma L.P.; Alan L. Koller; Weiying Yang

(57) ABSTRACT

The invention provides compounds that are useful as sodium channel blockers. In one aspect, the invention provides compounds of Formula I:

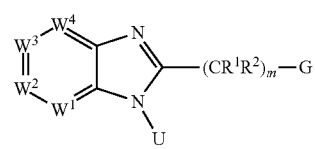

and pharmaceutically acceptable salts, solvates, hydrates, or diastereomers thereof, wherein $W^1$, $W^2$, $W^3$, $W^4$, U, G, m, $R^1$, and $R^2$ are defined in the disclosure. In certain embodiments, the invention provides compounds of Formulae II to V as set forth supra. The invention also provides the use of compounds of any of the above discussed formulae to treat a disorder responsive to blockade of sodium channels. In one embodiment, Compounds of the Invention are useful for treating pain.

10 Claims, No Drawings

(56) References Cited

U.S. PATENT DOCUMENTS

| | | | |
|---|---|---|---|
| 9,340,504 | B2 | 5/2016 | Park |
| 9,340,542 | B2 | 5/2016 | Lockman |
| 2002/0037926 | A1 | 3/2002 | Lan et al. |
| 2003/0083315 | A1 | 5/2003 | Tsuchiya et al. |
| 2003/0225080 | A1 | 12/2003 | Wang et al. |
| 2004/0176364 | A1 | 9/2004 | Sun et al. |
| 2004/0192691 | A1 | 9/2004 | Hogenkamp et al. |
| 2005/0043305 | A1 | 2/2005 | Hogenkamp et al. |
| 2005/0209176 | A1 | 9/2005 | Meutermans et al. |
| 2005/0209282 | A1* | 9/2005 | Wilson .............. C04B 35/632 514/320 |
| 2007/0138950 | A1 | 6/2007 | Yamamoto et al. |
| 2007/0254912 | A1 | 11/2007 | Chen et al. |
| 2008/0318932 | A1 | 12/2008 | Lan |
| 2009/0192169 | A1 | 7/2009 | Egle et al. |
| 2013/0289044 | A1 | 10/2013 | Goehring et al. |
| 2013/0296281 | A1 | 11/2013 | Kyle et al. |
| 2013/0303526 | A1 | 11/2013 | Ni et al. |
| 2013/0303535 | A1 | 11/2013 | Tsuboi et al. |
| 2013/0345211 | A1 | 12/2013 | Kyle et al. |
| 2014/0005212 | A1 | 1/2014 | Ni et al. |
| 2014/0249128 | A1 | 9/2014 | Tadesse et al. |
| 2014/0288092 | A1 | 9/2014 | Yao |
| 2014/0303139 | A1 | 10/2014 | Ni et al. |
| 2014/0309228 | A1 | 10/2014 | Engel |
| 2014/0315783 | A1 | 10/2014 | Shao |
| 2015/0045397 | A1 | 2/2015 | Tafesse et al. |
| 2015/0057300 | A1 | 2/2015 | Tafesse et al. |
| 2015/0175569 | A1 | 6/2015 | Lynch et al. |
| 2015/0259293 | A1 | 9/2015 | Ni et al. |
| 2015/0284383 | A1 | 10/2015 | Lynch et al. |
| 2015/0335642 | A1 | 11/2015 | Shao |
| 2015/0336974 | A1 | 11/2015 | Youngman |
| 2015/0353512 | A1 | 12/2015 | Tadesse et al. |
| 2016/0009659 | A1 | 1/2016 | Lockman et al. |
| 2016/0024022 | A1 | 1/2016 | Ni et al. |
| 2016/0031873 | A1 | 2/2016 | Yao et al. |
| 2016/0052911 | A1 | 2/2016 | Yao |
| 2016/0145210 | A1 | 5/2016 | Tafesse et al. |
| 2016/0207923 | A1 | 7/2016 | Youngman et al. |
| 2016/0243129 | A1 | 8/2016 | Hummel et al. |
| 2017/0001986 | A1 | 1/2017 | Yu |
| 2017/0008882 | A1 | 1/2017 | Lynch |
| 2017/0022213 | A1 | 1/2017 | Youngman |
| 2017/0057942 | A1 | 3/2017 | Tafesse et al. |
| 2017/0096421 | A1 | 4/2017 | Yao et al. |

FOREIGN PATENT DOCUMENTS

| | | | |
|---|---|---|---|
| WO | 94/12461 | A1 | 6/1994 |
| WO | 02/092575 | A1 | 11/2002 |
| WO | 2004/011439 | A2 | 2/2004 |
| WO | 2006/034402 | A2 | 3/2006 |
| WO | 2007/075629 | A2 | 7/2007 |
| WO | 2010/029299 | A1 | 3/2010 |
| WO | 2010/012745 | A2 | 4/2010 |
| WO | 2011/001115 | A1 | 1/2011 |
| WO | 2012/116440 | A1 | 9/2012 |
| WO | 2013/051672 | A1 | 11/2013 |
| WO | 2014/135955 | A1 | 9/2014 |
| WO | 2014/151393 | A2 | 9/2014 |
| WO | WO-2015/094443 | | 6/2015 |
| WO | WO-2015/112801 | | 7/2015 |

OTHER PUBLICATIONS

Anger. T., et al., "Medicinal Chemistry of Neuronal Voltage-Gated Sodium Channel Blockers," J. Med. Chem. 44 (2):115-137, American Chemical Society, United States (2001).

Baker, M.D. and Wood, J.N., "Involvement of Na+ channels in pain pathways," Trends Pharmacol. Sci. 22(1):27-31, Elsevier Science Ltd., England (2001).

Black, J.A., et al., "Sensory neuron-specific sodium channel SNS is abnormally expressed in the brains of mice with experimental allergic encephalomyelitis and humans with multiple sclerosis," Proc. Natl. Acad. Sci. USA 97 (21):11598-11602, National Academy of Sciences, United States (2000).

Brown, C.M., et al., "Neuroprotective properties of lifarizine compared with those of other agents in a mouse model of focal cerebral ischaemia," Br. J. Pharmacol. 115(8):1425-1432, Stockton Press, England (1995).

Catterall, W.A., "Common modes of drug action on Na+ channels: local anesthetics, antiarrhythmics and anticonvulsants," Trends Pharmacol. Sci. 8:57-65, Elsevier Science Publishers, B.V., Netherlands (1987).

Chahine, M., et al., "Voltage-Gated Sodium Channels in Neurological Disorders," CNS Neurol. Disord. Drug Targets 7(2):144-158, Bentham Science Publishers Ltd., United Arab Emirates (2008).

Clare, J.J., et al., "Voltage-gated sodium channels as therapeutic targets," Drug Discov. Today 5(11):506-520, Elsevier Science Ltd., England (2000).

Cannon, S.C., "Spectrum of Sodium Channel Disturbances in the nondystrophic myotonias and periodic paralyses," Kidney Int. 57(3)172-779, International Society of Nephrology, United States (2000).

Graham, S.H., et al., "Neuroprotective Effects of a Use-Dependent Blocker of Voltage-Dependent Sodium Channels, BW619C89, in Rat Middle Cerebral Artery Occlusion," J. Pharmacol. Exp. Ther. 269(2):854-859, The American Society for Pharmacology and Experimental Therapeutics, United States (1994).

Hubner, C., et al., "Ion Channel Diseases," Human Molecular Genetics 11:2435-2445, Oxford University Press (2002).

Kyle, D.J., and Ilyin, V.I., "Sodium Channel Blockers," J. Med. Chem. 50(11):2583-2588, American Chemical Society, United States (2007).

Lai, J., et al., "Voltage-Gated Sodium Channels and Hyperalgesia," Annu. Rev. Pharmacol. Toxicol. 44:371-397, Annual Reviews, United States (2004).

Lai, J., et al., "The role of voltage-gated sodium channels in neuropathic pain," Curr. Opin. Neurobiol. 13(3):291-297, Elsevier Science Ltd., England (2003).

Laird, J.M.A., et al., "Deficits in Visceral Pain and Referred Hyperalgesia in Nav1.8 (SNS/PN3)—Null Mice," J. Neurosci. 22(19):8352-8356, Society for Neuroscience, United States (2002).

Liu, H., et al., "Mutations in Cardiac Sodium Channels: Clinical Implications," Am. J. Pharmacogenomics 3(3):173-179, Adis Data Information BV, New Zealand (2003).

Majumdar, B., et al., "An electrocochleographic study of the effects of lignocaine on patients with tinnitus," Clin. Otolaryngol. Allied Sci. 8(3):175-180, Blackwell Scientific Publications, England (1983).

Meisler, M.H. and Kearney, J.A., "Sodium channel mutations in epilepsy and other neurological disorders," J. Clin. Invest. 115(8):2010-2017, American Society for Clinical Investigation, United States (2005).

Moller, A., "Similiarities Between Chronic Pain and Tinnitus," The American Journal of Ontology 18:577-585 (1997).

Nassar, M.A., et al., "Nociceptor-specific gene deletion reveals a major role for Nav1.7 (PN1) in acute and inflammatory pain," Proc. Natl. Acad. Sci. USA 101(34):12706-12711, National Academy of Sciences, United States (2004).

Noble, D., "Unraveling the genetics and mechanisms of cardiac arrhythmia," Proc. Natl. Acad. Sci. USA 99 (9):5755-5756, National Academy of Sciences, United States (2002).

Simpson, J.J. and Davies, W.E., "Recent advances in the pharmacological treatment of innitus," Trends Pharmacol. Sci. 20(1):12-18, Elsevier Science, England (1999).

Taylor, C.P. and Meldrum, B.S., "Na+ channels as targets for neuroprotective drugs," Trends Pharmacol. Sci. 16 (9):309-316, Elsevier Science Ltd., England (1995).

Toledo-Aral, J.J., et al., "Identification of PN1, a predominant voltage-dependent sodium channel expressed principally in peripheral neurons," Proc. Natl. Acad. Sci. USA 94(4):1527-1532, The National Academy of Sciences, United States (1997).

(56) References Cited

OTHER PUBLICATIONS

Tonndorf, J., "The analogy between tinnitus and pain: A suggestion for physiological basis of chronic tinnitus," Hearing Research 28(2-3):271-275, Elsevier Science Publishers B.V., Netherlands (1987).
Wood, J.N., et al., "Voltage-Gated Sodium Channels and Pain Pathways," J. Neurobiol. 61(1):55-71, Wiley Periodicals, Inc., United States (2004).
Yogeeswari, P., et al., "Ion Channels as Important Targets for Antiepileptic Drug Design," Curr. Drug Targets 5 (7):589-602, Bentham Science Publishers Ltd., Netherlands (2004).
Srivatsa, U., et al., "Mechanisms of Antiarrhythmic Drug Actions and Their Clinical Relevance for Controlling Disorders of Cardiac Rhythm," Curr. Cardiol. Rep. 4(5):401-410, Current Science Inc., United States (2002).
Hussein, F.A., et al. "1-(P- or M-Cinnamoylphenyl)-5-Nitrobenzimidazoles" Iraqi Journal of Science 23(3): 293-309, University of Baghdad, Baghdad, Iraq (1982).
Schwalbe, C., et al. "Studies in the Carbazole Series" Proceedings of the Chemical Society, 26(340): 340, London (1911).
Khristich, B.I., et al., "Free-Radical Hydroxymethylation of Benzimidazole" Khimiya Geterotsiklicheskikh Soedinenii, No. 12: 1679-1681, Rostov State Universtity, Russia (1982).
Cooper, K., et al. "Enantiodifferentiation of Dihydropyridine Paf Antagonists" Biorganic & Medicinal Chemistry Letters 5(24): 3085-3090, Elsevier Sicence Ltd, Great Britain (1995).
Zhu, Y., et al. "4-Methyl-5-phenyl triazoles as selctive inhibitors of 11B-hydroxysteroid dehydrogenase type I" Biorganic & Medicinal Chemistry Letters, 18(11): 3405-3411, Elsevier Science Ltd, (2008).

\* cited by examiner

BENZIMIDAZOLE DERIVATIVES AND USE THEREOF

CROSS-REFERENCE TO RELATED APPLICATIONS

This application claims priority to U.S. Provisional Application Ser. No. 61/901,507, filed Nov. 8, 2013. The content of the afore-mentioned patent application is incorporated herein by its entirety.

BACKGROUND OF THE INVENTION

Voltage-gated sodium channels (VGSCs) are found in all excitable cells. In neuronal cells of the central nervous system (CNS) and peripheral nervous system (PNS) sodium channels are primarily responsible for generating the rapid upstroke of the action potential. In this manner sodium channels are essential to the initiation and propagation of electrical signals in the nervous system. Proper function of sodium channels is therefore necessary for normal function of the neuron. Consequently, aberrant sodium channel function is thought to underlie a variety of medical disorders (See Hubner et al., *Hum. Mol. Genet.* 11:2435-2445 (2002) for a general review of inherited ion channel disorders) including epilepsy (Yogeeswari et al, *Curr. Drug Target* 5:589-602 (2004)), arrhythmia (Noble, *Proc. Natl. Acad. Sci. USA* 99:5755-5756 (2002)), myotonia (Cannon, *Kidney Int.* 57:772-779 (2000)), and pain (Wood et al., *J. Neurobiol.*, 61:55-71 (2004)).

VGSCs are composed of one α-subunit, which forms the core of the channel and is responsible for voltage-dependent gating and ion permeation, and several auxiliary β-subunits (see, e.g., Chahine et al., *CNS & Neurological Disorders-Drug Targets* 7:144-158 (2008) and Kyle and Ilyin, *J. Med. Chem.* 50:2583-2588 (2007)). α-Subunits are large proteins composed of four homologous domains. Each domain contains six α-helical transmembrane spanning segments. There are currently nine known members of the family of voltage-gated sodium channel α-subunits. Names for this family include SCNx, SCNAx, and $Na_v$x.x (see Table 1, below). The VGSC family has been phylogenetically divided into two subfamilies $Na_v$1.x (all but SCN6A) and $Na_v$2.x (SCN6A). The $Na_v$1.x subfamily can be functionally subdivided into two groups, those which are sensitive to blocking by tetrodotoxin (TTX-sensitive or TTX-s) and those which are resistant to blocking by tetrodotoxin (TTX-resistant or TTX-r).

There are three members of the subgroup of TTX-resistant sodium channels. The SCN5A gene product ($Na_v$1.5, HI) is almost exclusively expressed in cardiac tissue and has been shown to underlie a variety of cardiac arrhythmias and other conduction disorders (Liu et al., *Am. J. Pharmacogenomics* 3:173-179 (2003)). Consequently, blockers of $Na_v$1.5 have found clinical utility in treatment of such disorders (Srivatsa et al., *Curr. Cardiol. Rep.* 4:401-410 (2002)). The remaining TTX-resistant sodium channels, $Na_v$1.8 (SCN10A, PN3, SNS) and $Na_v$1.9 (SCN11A, NaN, SNS2) are expressed in the peripheral nervous system and show preferential expression in primary nociceptive neurons. Human genetic variants of these channels have not been associated with any inherited clinical disorder. However, aberrant expression of $Na_v$1.8 has been found in the CNS of human multiple sclerosis (MS) patients and also in a rodent model of MS (Black et al., *Proc. Natl. Acad. Sci. USA* 97:11598-115602 (2000)). Evidence for involvement in nociception is both associative (preferential expression in nociceptive neurons) and direct (genetic knockout). $Na_v$1.8-null mice exhibited typical nociceptive behavior in response to acute noxious stimulation but had significant deficits in referred pain and hyperalgesia (Laird et al., *J. Neurosci.* 22:8352-8356 (2002)).

TABLE 1

Voltage-gated sodium channel gene family

| Type | Gene Symbol | Tissue Distribution | TTX $IC_{50}$ (nM) | Disease Association | Indications |
|---|---|---|---|---|---|
| $Na_v$1.1 | SCN1A | CNS/PNS | 10 | Epilepsy | Pain, seizures, neurodegeneration |
| $Na_v$1.2 | SCN2A | CNS | 10 | Epilepsy | Epilepsy, neurodegeneration |
| $Na_v$1.3 | SCN3A | CNS | 15 | — | Pain |
| $Na_v$1.4 | SCN4A | Skeletal muscle | 25 | Myotonia | Myotonia |
| $Na_v$1.5 | SCN5A | Heart muscle | 2,000 | Arrhythmia | Arrhythmia |
| $Na_v$1.6 | SCN8A | CNS/PNS | 6 | — | Pain, movement disorders |
| $Na_v$1.7 | SCN9A | PNS | 25 | Erythermalgia | Pain |
| $Na_v$1.8 | SCN10A | PNS | 50,000 | — | Pain |
| $Na_v$1.9 | SCN11A | PNS | 1,000 | — | Pain |

The $Na_v$1.7 (PN1, SCN9A) VGSC is sensitive to blocking by tetrodotoxin and is preferentially expressed in peripheral sympathetic and sensory neurons. The SCN9A gene has been cloned from a number of species, including human, rat, and rabbit and shows ~90% amino acid identity between the human and rat genes (Toledo-Aral et al., *Proc. Natl. Acad. Sci. USA* 94:1527-1532 (1997)).

An increasing body of evidence suggests that $Na_v$1.7 plays a key role in various pain states, including acute, inflammatory and/or neuropathic pain. Deletion of the SCN9A gene in nociceptive neurons of mice led to an increase in mechanical and thermal pain thresholds and reduction or abolition of inflammatory pain responses (Nassar et al., *Proc Natl. Acad. Sci. USA* 101:12706-12711 (2004)).

Sodium channel-blocking agents have been reported to be effective in the treatment of various disease states, and have found particular use as local anesthetics, e.g., lidocaine and bupivacaine, and in the treatment of cardiac arrhythmias, e.g., propafenone and amiodarone, and epilepsy, e.g., lamotrigine, phenyloin and carbamazepine (see Clare et al., *Drug Discovery Today* 5:506-510 (2000); Lai et al., *Annu. Rev. Pharmacol. Toxicol.* 44:371-397 (2004); Anger et al., *J. Med. Chem.* 44:115-137 (2001), and Catterall, *Trends Pharmacol. Sci.* 8:57-65 (1987)). Each of these agents is believed to act by interfering with the rapid influx of sodium ions.

Other sodium channel blockers such as BW619C89 and lifarizine have been shown to be neuroprotective in animal models of global and focal ischemia (Graham et al., *J. Pharmacol. Exp. Ther.* 269:854-859 (1994); Brown et al., *British J. Pharmacol.* 115:1425-1432 (1995)).

It has also been reported that sodium channel-blocking agents can be useful in the treatment of pain, including acute, chronic, inflammatory, neuropathic, and other types of pain such as rectal, ocular, and submandibular pain typically associated with paroxysmal extreme pain disorder; see, for example, Kyle and Ilyin., *J. Med. Chem.* 50:2583-2588 (2007); Wood et al., *J. Neurobiol.* 61:55-71 (2004); Baker et al., *TRENDS in Pharmacological Sciences* 22:27-31 (2001); and Lai et al., *Current Opinion in Neurobiology* 13:291-297 (2003); the treatment of neurological disorders such as epilepsy, seizures, epilepsy with febrile seizures, epilepsy with benign familial neonatal infantile seizures, inherited pain disorders, e.g., primary erthermalgia and paroxysmal extreme pain disorder, familial hemiplegic migraine, and movement disorder; and the treatment of other psychiatric disorders such as autism, cerebellar atrophy, ataxia, and mental retardation; see, for example, Chahine et al., *CNS & Neurological Disorders-Drug Targets* 7:144-158 (2008) and Meister and Kearney, *J. Clin. Invest.* 5:2010-2017 (2005). In addition to the above-mentioned clinical uses, carbamazepine, lidocaine and phenyloin are used to treat neuropathic pain, such as from trigeminal neuralgia, diabetic neuropathy and other forms of nerve damage (Taylor and Meldrum, *Trends Pharmacol. Sci.* 16:309-316 (1995)). Furthermore, based on a number of similarities between chronic pain and tinnitus, (Moller, *Am. J. Otol.* 18:577-585 (1997); Tonndorf, *Hear. Res.* 28:271-275 (1987)) it has been proposed that tinnitus should be viewed as a form of chronic pain sensation (Simpson, et al., *Tip.* 20:12-18 (1999)). Indeed, lidocaine and carbamazepine have been shown to be efficacious in treating tinnitus (Majumdar, B. et al., *Clin. Otolaryngol.* 8:175-180 (1983); Donaldson, *Laryngol. Otol.* 95:947-951 (1981)).

Many patients with either acute or chronic pain disorders respond poorly to current pain therapies, and the development of resistance or insensitivity to opiates is common. In addition, many of the currently available treatments have undesirable side effects.

In view of the limited efficacy and/or unacceptable side-effects of the currently available agents, there is a pressing need for more effective and safer analgesics that work by blocking sodium channels.

SUMMARY OF THE INVENTION

The invention provides compounds that are useful as blockers of sodium ($Na^+$) channels. In one aspect, the invention provides compounds as represented by the formulae infra., and the pharmaceutically acceptable salts, solvates, hydrates, and diastereomers thereof (also referred to herein as "the Compounds of the Invention"). In certain embodiments, the Compounds of the Invention can act as blockers of sodium ($Na^+$) channels.

In one aspect, the invention provides novel compounds of any one of Formulae I to V as set forth below, and the pharmaceutically acceptable salts, solvates, hydrates, and diastereomers thereof.

The invention also provides a method of treating a disorder responsive to the blockade of sodium channels in a mammal suffering from excess activity of said channels by administering an effective amount of a Compound of the Invention as described herein.

A further aspect of the invention is to provide a method for treating pain (e.g., acute pain, chronic pain, which includes but is not limited to, neuropathic pain, postoperative pain, and inflammatory pain, or surgical pain) by administering an effective amount of a Compound of the Invention to a mammal in need of such treatment. In a certain embodiment, the invention provides a method for preemptive or palliative treatment of pain by administering an effective amount of a Compound of the Invention to a mammal in need of such treatment.

A further aspect of the invention is to provide a method for treating stroke, neuronal damage resulting from head trauma, epilepsy, seizures, general epilepsy with febrile seizures, severe myoclonic epilepsy in infancy, neuronal loss following global and focal ischemia, migraine, familial primary erythromelalgia, paroxysmal extreme pain disorder, cerebellar atrophy, ataxia, dystonia, tremor, mental retardation, autism, a neurodegenerative disorder (e.g., Alzheimer's disease, amyotrophic lateral sclerosis (ALS), or Parkinson's disease), manic depression, tinnitus, myotonia, a movement disorder, or cardiac arrhythmia, or providing local anesthesia, by administering an effective amount of a Compound of the Invention to a mammal in need of such treatment.

A further aspect of the invention provides a pharmaceutical composition useful for treating a disorder responsive to blockade of sodium ion channels, said pharmaceutical composition containing an effective amount of a Compound of the Invention in a mixture with one or more pharmaceutically acceptable diluent and/or carriers.

Also, an aspect of the invention provides a method of modulating sodium channels in a mammal, wherein said method comprises administering to the mammal an effective amount of at least one Compound of the Invention.

In another aspect, the invention relates to the use of the compounds of the formulae provided infra. and their pharmaceutically acceptable salts, diastereomers, hydrates, and solvates, as blockers of sodium channels.

A further aspect of the invention provides a Compound of the Invention for use in treating pain in a mammal, e.g., acute pain, chronic pain, which includes but is not limited to, neuropathic pain, postoperative pain, and inflammatory pain, or surgical pain.

Yet another aspect of the invention provides a Compound of the Invention for use in treating stroke, neuronal damage resulting from head trauma, epilepsy, seizures, general epilepsy with febrile seizures, severe myoclonic epilepsy in infancy, neuronal loss following global and focal ischemia, migraine, familial primary erythromelalgia, paroxysmal extreme pain disorder, cerebellar atrophy, ataxia, dystonia, tremor, mental retardation, autism, a neurodegenerative disorder (e.g., Alzheimer's disease, amyotrophic lateral sclerosis (ALS), or Parkinson's disease), manic depression, tinnitus, myotonia, a movement disorder, or cardiac arrhythmia, or providing local anesthesia, in a mammal.

Still another aspect of the invention provides radiolabeled Compounds of the Invention and the use of such compounds as radioligands in any appropriately selected competitive binding assays and screening methodologies. Thus, the invention further provides a method for screening a candidate compound for its ability to bind to a sodium channel or sodium channel subunit using a radiolabeled Compound of the Invention.

In certain embodiments, the compound is radiolabeled with $^3H$, $^{11}C$, or $^{14}C$. This competitive binding assay can be conducted using any appropriately selected methodology. In one embodiment, the screening method comprises: i) introducing a fixed concentration of the radiolabeled compound to an in vitro preparation comprising a soluble or membrane-associated sodium channel, subunit or fragment under conditions that permit the radiolabeled compound to bind to the channel, subunit or fragment, respectively, to form a conjugate; ii) titrating the conjugate with a candidate compound; and iii) determining the ability of the candidate compound to displace the radiolabeled compound from said channel, subunit or fragment.

A further aspect of the invention provides the use of a Compound of the Invention in the manufacture of a medicament for treating pain in a mammal. In one embodiment, the invention provides the use of a Compound of the Invention in the manufacture of a medicament for palliative or preemptive treatment of pain, such as acute pain, chronic pain, or surgical pain.

In another aspect, the invention provides the use of a Compound of the Invention in the manufacture of a medicament for treating stroke, neuronal damage resulting from head trauma, epilepsy, seizures, general epilepsy with febrile seizures, severe myoclonic epilepsy in infancy, neuronal loss following global and focal ischemia, migraine, familial primary erythromelalgia, paroxysmal extreme pain disorder, cerebellar atrophy, ataxia, dystonia, tremor, mental retardation, autism, a neurodegenerative disorder (e.g., Alzheimer's disease, amyotrophic lateral sclerosis (ALS), or Parkinson's disease), manic depression, tinnitus, myotonia, a movement disorder, or cardiac arrhythmia, or providing local anesthesia, in a mammal.

Additional embodiments and advantages of the invention will be set forth in part in the description that follows, and will flow from the description, or can be learned by practice of the invention. The embodiments and advantages of the invention will be realized and attained by means of the elements and combinations particularly pointed out in the appended claims.

It is to be understood that both the foregoing summary and the following detailed description are exemplary and explanatory only and are not restrictive of the invention as claimed.

DETAILED DESCRIPTION OF THE INVENTION

Definitions

Before a further description of the invention, and in order that the invention may be more readily understood, certain terms are first defined and collected herein for convenience.

As used herein, the term "alkyl" by itself or as part of another group refers to a straight- or branched-chain aliphatic hydrocarbon containing one to twelve (i.e. 1, 2, 3, 4, 5, 6, 7, 8, 9, 10, 11, or 12) carbon atoms (i.e., $C_{1-12}$ alkyl) or the number of carbon atoms designated (i.e., a $C_1$ alkyl such as methyl, a $C_2$ alkyl such as ethyl, a $C_3$ alkyl such as propyl or isopropyl, etc.). For convenience, the term "alkyl" as used herein also includes an alkanediyl functional group, for example, an alkyl group that has two points of connection, such as, —CH$_2$— and —CH$_2$CH$_2$—. Nevertheless, the term "alkyl" as used in the present disclosure does not expressly include unsaturated aliphatic hydrocarbon chains (e.g., alkenyl and alkynyl groups). In addition, the term "$C_0$ alkyl" as used herein refers to a bond (i.e., absent) or H.

In one embodiment, the alkyl group is chosen from a straight chain $C_{1-10}$ alkyl group. In another embodiment, the alkyl group is chosen from a branched chain $C_{1-10}$ alkyl group. In another embodiment, the alkyl group is chosen from a straight chain $C_{1-6}$ alkyl group. In another embodiment, the alkyl group is chosen from a branched chain $C_{3-6}$ alkyl group. In another embodiment, the alkyl group is chosen from a straight chain $C_{1-4}$ alkyl group. In another embodiment, the alkyl group is chosen from a straight chain $C_{2-4}$ alkyl group. In another embodiment, the alkyl group is chosen from a branched chain $C_{3-4}$ alkyl group. Non-limiting exemplary alkyl groups include methyl, ethyl, propyl, butyl, pentyl, hexyl, heptyl, octyl, nonyl, decyl, -iso-propyl, -sec-butyl, -iso-butyl, -tert-butyl, -iso-pentyl, -neopentyl, 1-methylbutyl, 2-methylbutyl, 3-methylbutyl, 1,1-dimethylpropyl, 1,2-dimethylpropyl, 1-methylpentyl, 2-methylpentyl, 3-methylpentyl, 4-methylpentyl, 1-ethylbutyl, 2-ethylbutyl, 3-ethylbutyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-methylhexyl, 2-methylhexyl, 3-methylhexyl, 4-methylhexyl, 5-methylhexyl, 1,2-dimethylpentyl, 1,3-dimethylpentyl, 1,2-dimethylhexyl, 1,3-dimethylhexyl, 3,3-dimethylhexyl, 1,2-dimethylheptyl, 1,3-dimethylheptyl, and 3,3-dimethylheptyl and the like. Non-limiting exemplary $C_{1-4}$ alkyl groups include methyl, ethyl, propyl, isopropyl, butyl, sec-butyl, tert-butyl, and iso-butyl.

For the purpose of the disclosure, the term "optionally substituted alkyl" as used by itself or as part of another group means that the alkyl as defined above is either unsubstituted or substituted with one or more substituents independently chosen from amide, (amido)alkyl, hydroxyl, carboxy, alkoxy, ureido, nitro, halogen, alkyl, alkylcarbonyl, alkylsulfonyl, arylsulfonyl, sulfonamide, guanidino, carboxyalkyl, cycloalkyl, heterocyclyl, heteroaryl, haloalkoxy, aryloxy, aralkyloxy, alkylthio, arylcarbonyl, and the like. In one embodiment, the optionally substituted alkyl is substituted with two substituents. In another embodiment, the optionally substituted alkyl is substituted with one substituent. Non-limiting exemplary optionally substituted alkyl groups include —CH$_2$CH$_2$NO$_2$, —CH$_2$CH$_2$CO$_2$H, —CH$_2$CH$_2$SO$_2$CH$_3$, —CH$_2$CH$_2$COPh, and the like.

As used herein, the term "cycloalkyl" by itself or as part of another group refers to saturated, partially unsaturated (e.g. cycloalkenyl that contains one or two double bonds), and partially-oxidized (e.g., containing a carbon atom out of a carbonyl group as a ring building block) cyclic aliphatic hydrocarbons containing one to three rings with or without the number of carbons designated. In certain embodiments, the term "cycloalkyl" as used herein has from three to twelve carbon atoms (i.e., $C_{3-12}$ cycloalkyl). In one embodiment, the cycloalkyl group is saturated. In another embodiment, the cycloalkyl group is unsaturated. In still another embodiment, the cycloalkyl group is oxidized (e.g., a cyclohexanone group).

In one embodiment, the cycloalkyl group has two-fused rings. In one embodiment, the cycloalkyl group has one ring. In another embodiment, the cycloalkyl group is chosen from a $C_{3-8}$ cycloalkyl group. In another embodiment, the cycloalkyl group is chosen from a $C_{4-8}$ cycloalkyl group. In another embodiment, the cycloalkyl group is chosen from a $C_{3-6}$ cycloalkyl group. Non-limiting exemplary cycloalkyl groups include cyclopropyl, cyclobutyl, cyclopentyl, cyclohexyl, cycloheptyl, cyclooctyl, norbornyl, decalin, adamantyl, cyclohexenyl, cycloheptenyl, cyclooctenyl, cyclooctadienyl, cyclooctatrienyl, and the like.

The term "optionally substituted cycloalkyl" as used by itself or as part of another group means that the cycloalkyl as defined above is either unsubstituted or substituted with or more substituents independently chosen from halo, nitro, cyano, hydroxy, amino, alkylamino, dialkylamino, haloalkyl, hydroxyalkyl, dihydroxyalkyl, alkoxy, haloalkoxy, aryloxy, aralkyloxy, alkylthio, carboxamido, sulfonamido, alkylcarbonyl, arylcarbonyl, alkylsulfonyl, arylsulfonyl, ureido, guanidino, carboxy, carboxyalkyl, alkyl, cycloalkyl, alkenyl, alkynyl, aryl, heteroaryl, heterocyclyl, alkoxyalkyl, (amino)alkyl, hydroxyalkylamino, (alkylamino)alkyl, (dialkylamino)alkyl, (cyano)alkyl, (carboxamido)alkyl, mercaptoalkyl, (heterocyclyl)alkyl, (heteroaryl)alkyl, and the like.

In certain embodiments, the optionally substituted cycloalkyl is substituted with one to three substituents. As illustration, non-limiting exemplary optionally substituted cycloalkyl groups include:

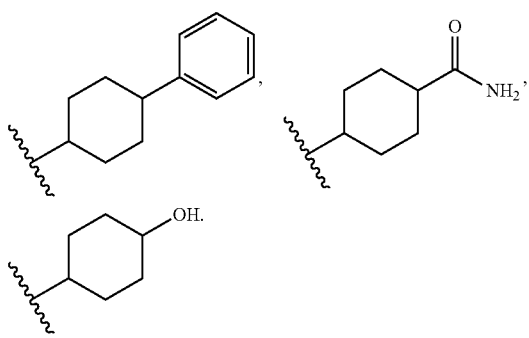

The term "cycloalkenyl" as used by itself or part of another group refers to a cycloalkyl group as defined above containing one, two, or three carbon-to-carbon double bonds. In one embodiment, the cycloalkenyl has one carbon-to-carbon double bond. In another embodiment, the cycloalkenyl group is chosen from a $C_{4-8}$ cycloalkenyl group. Exemplary cycloalkenyl groups include cyclopentenyl, cyclohexenyl, cycloheptenyl, cyclooctenyl, cyclooctenyl, cyclooctadienyl, cyclooctatrienyl, and the like.

The term "alkenyl" as used by itself or as part of another group refers to an alkyl group as defined above containing one, two or three carbon-to-carbon double bonds. In one embodiment, the alkenyl group is chosen from a $C_{2-6}$ alkenyl group. In another embodiment, the alkenyl group is chosen from a $C_{2-4}$ alkenyl group. Non-limiting exemplary alkenyl groups include ethenyl, propenyl, isopropenyl, butenyl, sec-butenyl, -iso-butylenyl, -1-pentenyl, -2-pentenyl, -3-methyl-1-butenyl, -2-methyl-2-butenyl, -2,3-dimethyl-2-butenyl, -1-hexenyl, -2-hexenyl, -3-hexenyl, -1-heptenyl, -2-heptenyl, -3-heptenyl, -1-octenyl, -2-octenyl, -3-octenyl, -1-nonenyl, -2-nonenyl, -3-nonenyl, -1-decenyl, -2-decenyl, -3-decenyl, and the like.

The term "alkynyl" as used by itself or as part of another group refers to an alkyl group as defined above containing one to three carbon-to-carbon triple bonds. In one embodiment, the alkynyl has one carbon-to-carbon triple bond. In one embodiment, the alkynyl group is chosen from a $C_{2-6}$ alkynyl group. In another embodiment, the alkynyl group is chosen from a $C_{2-4}$ alkynyl group. Non-limiting exemplary alkynyl groups include ethynyl, propynyl, butynyl, 2-butynyl, -1-pentynyl, -2-pentynyl, -3-methyl-1-butynyl, -4-pentynyl, -1-hexynyl, -2-hexynyl, 3-hexynyl, -5-hexynyl, -1-heptynyl, -2-heptynyl, -6-heptynyl, -1-octynyl, -2-octynyl, -7-octynyl, -1-nonynyl, -2-nonynyl, -8-nonynyl, -1-decynyl, -2-decynyl, -9-decynyl, and the like.

The term "haloalkyl" as used by itself or as part of another group refers to an alkyl group as defined above substituted by one or more fluorine, chlorine, bromine and/or iodine atoms. In one embodiment, the alkyl group is substituted by one, two, or three fluorine and/or chlorine atoms. In another embodiment, the haloalkyl group is chosen from a $C_{1-4}$ haloalkyl group. Non-limiting exemplary haloalkyl groups include fluoromethyl, difluoromethyl, trifluoromethyl, pentafluoroethyl, 1,1-difluoroethyl, 2,2-difluoroethyl, 2,2,2-trifluoroethyl, 3,3,3-trifluoropropyl, 4,4,4-trifluorobutyl, and trichloromethyl groups.

The term "hydroxyalkyl" as used by itself or as part of another group refers to an alkyl group as defined above substituted with a hydroxyl group (i.e., —OH).

As used herein, the term "alkoxy" by itself or as part of another group refers to an optionally substituted alkyl as above defined, an optionally substituted cycloalkyl as above defined, an optionally substituted heterocyclyl (defined infra.), an optionally substituted aryl (defined infra.), or an optionally substituted heteroaryl (defined infra.) that is attached to an oxygen atom, i.e., —OR$^c$ (wherein R$^c$ is alkyl, cycloalkyl, heterocyclyl, aryl or heteroaryl, each of which is optionally substituted). Exemplified alkoxy groups include methoxy, ethoxy, tert-butoxy, cyclohexanoxy, and the like.

For the purpose of this disclosure, the term "—S-alkyl" or "alkylthio" as used by itself or as part of another group refers to a sulfur atom substituted by an optionally substituted alkyl group as above defined. Non-limiting exemplary —S-alkyl or alkylthio groups include —SCH$_3$, and —SCH$_2$CH$_3$.

The term "alkoxyalkyl" as used herein by itself or as part of another group refers to any of the above-mentioned alkyl groups substituted with any of the above-mentioned alkoxy groups. Non-limiting exemplary alkoxyalkyl groups include, but are not limited to, methoxymethyl, methoxyethyl, methoxypropyl, methoxybutyl, ethoxymethyl, ethoxyethyl, ethoxypropyl, ethoxybutyl, propoxymethyl, iso-propoxymethyl, propoxyethyl, propoxypropyl, butoxymethyl, tert-butoxymethyl, isobutoxymethyl, sec-butoxymethyl, and pentyloxymethyl.

The term "haloalkoxy" as used herein by itself or as part of another group refers to an alkoxy group as above defined that is substituted by one or more same or different halogen atoms (i.e., fluorine, chlorine, bromine and iodine atoms). Non-limiting exemplary haloalkoxy groups include fluoromethoxy, difluoromethoxy, trifluoromethoxy, and 2,2,2-trifluoroethoxy.

As used herein, the term "aryl" by itself or as part of another group refers to a monocyclic or bicyclic aromatic ring system having from six to fourteen carbon atoms (i.e., $C_6$-$C_{14}$ aryl). Non-limiting exemplary aryl groups include phenyl (abbreviated as "Ph"), naphthyl, phenanthryl, anthracyl, indenyl, azulenyl, biphenyl, biphenylenyl, and fluorenyl groups.

The term "optionally substituted aryl" as used herein by itself or as part of another group means that the aryl as defined above is either unsubstituted or substituted with one to five substituents independently chosen from halo, nitro, cyano, hydroxy, amino, alkylamino, dialkylamino, haloalkyl, hydroxyalkyl, dihydroxyalkyl, alkoxy, haloalkoxy, aryloxy, aralkyloxy, alkylthio, carboxamido, sulfonamido, alkylcarbonyl, arylcarbonyl, alkylsulfonyl, arylsulfonyl, ureido, guanidino, carboxy, carboxyalkyl, alkyl, cycloalkyl, alkenyl, alkynyl, aryl, heteroaryl, heterocyclyl, alkoxyalkyl, (amino)alkyl, hydroxyalkylamino, (alkylamino)alkyl, (dialkylamino)alkyl, (cyano)alkyl, (carboxamido)alkyl, mercaptoalkyl, (heterocyclyl)alkyl, (heteroaryl)alkyl, and the like.

In certain embodiments, the optionally substituted aryl is an optionally substituted phenyl that has one to five substituents. Non-limiting exemplary substituted aryl groups include 2-methylphenyl, 2-methoxyphenyl, 2-fluorophenyl, 2-chlorophenyl, 2-bromophenyl, 3-methylphenyl, 3-methoxyphenyl, 3-fluorophenyl, 3-chlorophenyl, 4-methylphenyl, 4-ethylphenyl, 4-methoxyphenyl, 4-fluorophenyl, 4-chlorophenyl, 2,6-di-fluorophenyl, 2,6-di-chlorophenyl, 2-methyl, 3-methoxyphenyl, 2-ethyl, 3-methoxyphenyl, 3,4-di-methoxyphenyl, 3,5-di-fluorophenyl 3,5-di-methylphenyl and 3,5-dimethoxy, 4-methylphenyl, 2-fluoro-3-chlorophenyl, 2-cyano-3-trifluoromethylphenyl, 2-trifluoromethyl-3-cyanophenyl, 4-cyanophenyl, 4-trifluoromethylphenyl, and 3-chloro-4-fluorophenyl. The term optionally substituted aryl is meant to include groups having fused optionally substituted cycloalkyl and fused optionally substituted heterocyclyl rings. Examples include

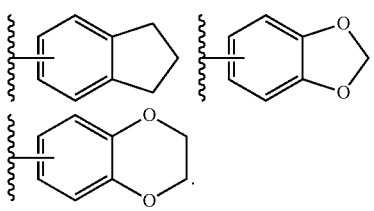

The term "aryloxy" as used by itself or as part of another group refers to an optionally substituted aryl attached to a terminal oxygen atom. A non-limiting exemplary aryloxy group is PhO—.

The term "aralkyloxy" as used by itself or as part of another group refers to an aralkyl group attached to a terminal oxygen atom. A non-limiting exemplary aralkyloxy group is PhCH$_2$O—.

The term "heteroaryl" or "heteroaromatic" refers to monocyclic and bicyclic aromatic ring systems having 1, 2, 3, or 4 heteroatoms. In certain embodiments, the heteroatoms are independently selected from the group consisting of oxygen, nitrogen, and sulfur. In others embodiments, the heteroaryl is a 5-membered or 6-membered heteroaryl. Non-limiting exemplary heteroaryl groups include thienyl, benzo[b]thienyl, naphthol[2,3-b]thienyl, thianthrenyl, furyl, benzofuryl, pyranyl, isobenzofuranyl, benzooxazonyl, chromenyl, xanthenyl, 2H-pyrrolyl, pyrrolyl, imidazolyl, pyrazolyl, pyridyl, pyrazinyl, pyrimidinyl, pyridazinyl, isoindolyl, 3H-indolyl, indolyl, indazolyl, purinyl, isoquinolyl, quinolyl, phthalazinyl, naphthyridinyl, cinnolinyl, quinazolinyl, pteridinyl, 4aH-carbazolyl, carbazolyl, β-carbolinyl, phenanthridinyl, acridinyl, pyrimidinyl, phenanthrolinyl, phenazinyl, thiazolyl, isothiazolyl, phenothiazolyl, isoxazolyl, furazanyl, benzimidazolyl, and phenoxazinyl. In one embodiment, the heteroaryl is chosen from thienyl (e.g., thien-2-yl and thien-3-yl), furyl (e.g., 2-furyl and 3-furyl), pyrrolyl (e.g., 1H-pyrrol-2-yl and 1H-pyrrol-3-yl), imidazolyl (e.g., 2H-imidazol-2-yl and 2H-imidazol-4-yl), pyrazolyl (e.g., 1H-pyrazol-3-yl, 1H-pyrazol-4-yl, and 1H-pyrazol-5-yl), pyridyl (e.g., pyridin-2-yl, pyridin-3-yl, and pyridin-4-yl), pyrimidinyl (e.g., pyrimidin-2-yl, pyrimidin-4-yl, pyrimidin-5-yl, and pyrimidin-5-yl), thiazolyl (e.g., thiazol-2-yl, thiazol-4-yl, and thiazol-5-yl), isothiazolyl (e.g., isothiazol-3-yl, isothiazol-4-yl, and isothiazol-5-yl), oxazolyl (e.g., oxazol-2-yl, oxazol-4-yl, and oxazol-5-yl) and isoxazolyl (e.g., isoxazol-3-yl, isoxazol-4-yl, and isoxazol-5-yl). The term "heteroaryl" is also meant to include possible N-oxides. Exemplary N-oxides include pyridyl N-oxide and the like.

The term "optionally substituted heteroaryl" as used by itself or as part of another group means that the heteroaryl as defined above is either unsubstituted or substituted with one to four substituents, e.g., one or two substituents, independently chosen from halo, nitro, cyano, hydroxy, amino, alkylamino, dialkylamino, haloalkyl, monohydroxyalkyl, dihydroxyalkyl, alkoxy, haloalkoxy, aryloxy, aralkyloxy, alkylthio, carboxamido, sulfonamido, alkylcarbonyl, arylcarbonyl, alkylsulfonyl, arylsulfonyl, ureido, guanidino, carboxy, carboxyalkyl, alkyl, cycloalkyl, alkenyl, alkynyl, aryl, heteroaryl, heterocyclyl, alkoxyalkyl, (amino)alkyl, hydroxyalkylamino, (alkylamino)alkyl, (dialkylamino)alkyl, (cyano)alkyl, (carboxamido)alkyl, mercaptoalkyl, (heterocyclyl)alkyl, and (heteroaryl)alkyl. In one embodiment, the optionally substituted heteroaryl has one substituent. In one embodiment, the optionally substituted is an optionally substituted pyridyl, i.e., 2-, 3-, or 4-pyridyl. Any available carbon or nitrogen atom can be substituted. In another embodiment, the optionally substituted heteroaryl is an optionally substituted indole.

The term "heterocyclyl", "heterocycle", or "heterocyclic" as used by itself or as part of another group refers to saturated and partially unsaturated (e.g., containing one or two double bonds) cyclic groups containing one, two, or three rings having from 3 to 14 ring members and at least one heteroatom. Further, the term "heterocyclyl" or "heterocycle" as used herein is meant to include cyclic groups that are partially oxidized, for example, 2-imidazolidinone, and pyrrolidin-2-one, etc.

A 3-membered heterocyclyl can contain up to 1 heteroatom, a 4-membered heterocyclyl can contain up to 2 heteroatoms, a 5-membered heterocyclyl can contain up to 4 heteroatoms, and a 6-membered heterocyclyl can contain up to 4 heteroatoms, and a 7-membered heterocyclyl can contain up to 5 heteroatoms. Each heteroatom is independently selected from the group consisting of oxygen, sulfur (including sulfoxide and sulfone), and/or nitrogen atoms that can be quaternized. In certain embodiments, the heterocyclyl or heterocycle group is chosen from a 5- or 6-membered cyclic group containing one ring and one or two oxygen and/or nitrogen atoms. In another embodiment, the heterocyclyl or heterocycle group is chosen from a 4- to 8-membered heterocycle. In another embodiment, the heterocyclyl or heterocycle group is chosen from a 4- to 12-membered heterocycle. In another embodiment, the heterocyclyl or heterocycle group is chosen from a 3- to 8-membered heterocycle. The heterocyclyl or heterocycle can be optionally linked to the rest of the molecule through a carbon or hetero atom. Non-limiting exemplary heterocyclyl or heterocycle groups include 2-imidazolidinone, piperidinyl, morpholinyl, piperazinyl, and pyrrolidinyl.

The term "optionally substituted heterocyclyl" or "optionally substituted heterocycle" as used herein by itself or part of another group means the heterocyclyl or heterocycle as defined above is either unsubstituted or substituted with one to five substituents independently selected from halo, nitro, cyano, hydroxy, amino, alkylamino, dialkylamino, haloalkyl, monohydroxyalkyl, dihydroxyalkyl, alkoxy, haloalkoxy, aryloxy, aralkyloxy, alkylthio, carboxamido, sulfonamido, alkylcarbonyl, arylcarbonyl, alkylsulfonyl, arylsulfonyl, ureido, guanidino, carboxy, carboxyalkyl, alkyl, cycloalkyl, alkenyl, alkynyl, aryl, heteroaryl, heterocyclyl, alkoxyalkyl, (amino)alkyl, hydroxyalkylamino, (alkylamino)alkyl, (dialkylamino)alkyl, (cyano)alkyl, (carboxamido)alkyl, mercaptoalkyl, (heterocyclyl)alkyl, (heteroaryl)alkyl, and the like. Substitution may occur on any available carbon or nitrogen atom. An optionally substituted heterocyclyl or heterocycle can be fused to an aryl group to provide an optionally substituted aryl as described above. Non-limiting exemplary optionally substituted heterocyclyl or heterocycle groups include:

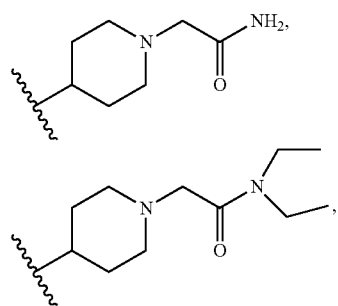

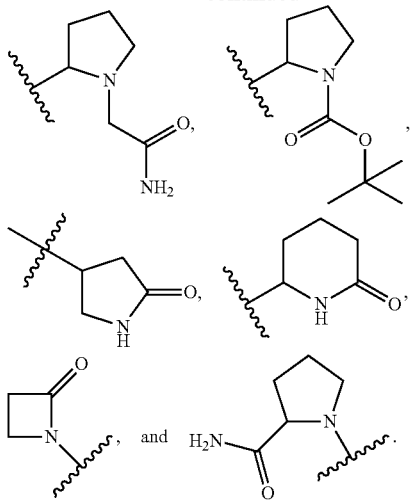

The term "amino" as used herein by itself or as part of another group refers to —NH$_2$.

The phrase "optionally substituted amino" by itself or as part of another group means that the amino as defined above is either unsubstituted or substituted with one or two substituents independently selected from (amido)alkyl, carboxy, carboxamido, alkyl, alkylcarbonyl, alkylsulfonyl, arylsulfonyl, carboxyalkyl, cycloalkyl, heterocyclyl, heteroaryl, arylcarbonyl, (cycloalkyl)carbonyl, and the like. Each of the above amino substituents can be further optionally substituted.

The term "(amino)alkyl" or "aminoalkyl" as used herein by itself or as part of another group refers to any of the above-mentioned alkyl groups substituted with an amino group. Non-limiting exemplary amino alkyl groups include —CH$_2$NH$_2$, —CH$_2$CH$_2$NH$_2$, —CH$_2$CH$_2$CH$_2$NH$_2$, —CH$_2$CH$_2$CH$_2$CH$_2$NH$_2$ and the like.

The term "alkylamino" or "(alkyl)amino" as used herein by itself or as part of another group refers to an amino group substituted by an alkyl group as above mentioned. Non-limiting exemplary alkylamino or (alkyl)amino groups include —NHCH$_3$, —NHCH$_2$CH$_3$, and the like.

The term "dialkylamino" or "(dialkyl)amino" as used herein by itself or as part of another group refers to an amino group substituted by two alkyl groups as above mentioned, which can be the same or different. Non-limiting exemplary dialkylamino groups include —N(CH$_3$)$_2$, —N(CH$_3$)(CH$_2$CH$_3$), and the like.

The "arylamino" as used herein by itself or as part of another group refers to an amino group substituted by an aryl group as above mentioned. Non-limiting exemplary dialkylamino groups include —NHPh and the like.

For the purpose of the present disclosure, the term "cycloalkylamino" as used by itself or as part of another group refers to an amino group substituted by a cycloalkyl group as above mentioned. Non-limiting exemplary cycloalkylamino groups include

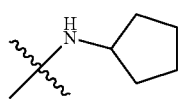 [SMILES: *NC1CCCC1]

and the like.

The term "cyano" by itself or as part of another group stands for a —CN group.

As used herein, the term "amide" or "amido" by itself or as part of another group refers to a radical having the formula of —C(=O)NR$^a$R$^b$ (i.e., —C(O)NR$^a$R$^b$) or —N(R$^a$)C(O)—, wherein R$^a$ and R$^b$ are each independently hydrogen, optionally substituted alkyl, optionally substituted aryl, or optionally substituted heteroaryl; or R$^a$ and R$^b$ taken together with the nitrogen to which they are attached form a 3- to 8-membered heterocycle group. Non-limiting exemplary amide or amido groups include —C(O)NH$_2$, —NHC(O)CH$_3$, and the like.

The term "carboxamido" by itself or as part of another group refers to a radical of formula —C(=O)NR$^a$R$^b$, wherein R$^a$ and R$^b$ are each independently hydrogen, optionally substituted alkyl, optionally substituted aryl, or optionally substituted heteroaryl; or R$^a$ and R$^b$ taken together with the nitrogen to which they are attached form a 3- to 8-membered heterocycle group. Non-limiting exemplary carboxamido groups include —C(O)NH$_2$, —C(O)N(H)CH$_3$, —C(O)N(CH$_3$)$_2$, and —C(O)N(H)Ph.

The term "(amido)alkyl" by itself or as part of another group refers to an alkyl group that is substituted by an amido group as above defined. Non-limiting exemplary (amido)alkyl groups include —CH$_2$CONH$_2$,

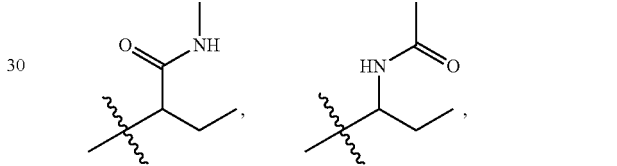

and the like.

The term "sulfonamide" or "sulfonamido" as used herein by itself or as part of another group refers to a radical of the formula —SO$_2$N(R$^{2a}$R$^{2b}$), wherein R$^{2a}$ and R$^{2b}$ are each independently hydrogen, optionally substituted alkyl, optionally substituted cycloalkyl, optionally substituted aryl, or optionally substituted heteroaryl; or R$^{2a}$ and R$^{2b}$ taken together with the nitrogen to which they are attached form a 3- to 8-membered heterocyclyl group. Non-limiting exemplary sulfonamido groups include —SO$_2$NH$_2$, —SO$_2$N(H)CH$_3$, —SO$_2$N(H)Ph, and the like.

The term "carbonyl" as used by itself or as part of another group refers to —C(=O)— (i.e, —C(O)—).

The term "alkylsulfonyl" as used herein by itself or as part of another group refers to a sulfonyl group, i.e., —SO$_2$—, substituted by any of the above-mentioned optionally substituted alkyl groups. A non-limiting exemplary alkylsulfonyl group is —SO$_2$CH$_3$.

The term "arylsulfonyl" by itself or as part of another group refers to a sulfonyl group, i.e., —SO$_2$—, substituted by any of the above-mentioned optionally substituted aryl groups. A non-limiting exemplary arylsulfonyl group is —SO$_2$Ph.

The term "mercaptoalkyl" as used by itself or as part of another group refers to any of the above-mentioned alkyl groups substituted by a —SH group.

The term "sulfinyl" as used by itself or as part of another group refers to a —S(=O)-group substituted by any of the above-mentioned optionally substituted alkyl groups. A non-limiting exemplary alkylsulfinyl group is —S(=O)CH$_3$.

The term "carboxy" as used by itself or as part of another group refers to a radical of the formula —COOH.

The term "nitro" as used herein by itself or as part of another group refers to a radical of the formula —NO$_2$.

The term "hydroxy" or "hydroxyl" as used herein by itself or as part of another group refers to a radical of the formula —OH.

As used herein, the term "aralkyl" by itself or as part of another group refers to any of the above-mentioned alkyl groups substituted with one, two, or three optionally substituted aryl groups. In one embodiment, the aralkyl group is a $C_{1-4}$ alkyl substituted with one optionally substituted aryl group. Non-limiting exemplary aralkyl groups include benzyl, trityl, and phenethyl.

The term "ureido" as used by itself or as part of another group refers to a radical of the formula —NR$^{3a}$—C(O)—NR$^{3b}$R$^{3d}$, wherein R$^{3a}$, R$^{3b}$ and R$^{3d}$, each independently, are hydrogen, optionally substituted alkyl, optionally substituted cycloalkyl, optionally substituted aryl, or optionally substituted heteroaryl; or R$^{3b}$ and R$^{3d}$ taken together with the nitrogen to which they are attached form a 4- to 8-membered heterocyclyl group. Non-limiting exemplary ureido groups include —NH—C(=O)—NH$_2$ and NH—C(=O)—NHCH$_3$.

The term "guanidino" as used by itself or as part of another group refers to a radical of the formula —NR$^{4a}$—C(=NR$^{4b}$)—NR$^{4c}$R$^{4d}$, wherein R$^{4a}$, R$^{4c}$, and R$^{4d}$ are each independently hydrogen, optionally substituted alkyl, optionally substituted cycloalkyl, optionally substituted aryl, or optionally substituted heteroaryl; and R$^{4b}$ is hydrogen, alkyl, cyano, alkylsulfonyl, alkylcarbonyl, carboxamido, or sulfonamido. Non-limiting exemplary guanidino groups include —NH—C(C=NH)—NH$_2$, —NH—C(C=NCN)—NH$_2$, —NH—C(C=NH)—NHCH$_3$ and the like.

The term "chiral" refers to molecules which have the property of non-superimposability of their mirror image partner, which the term "achiral" refers to molecules which are superimposable on their mirror image partner.

The term "diastereomer" refers to stereoisomers with two or more centers of dissymmetry and whose structures are not mirror images of each other.

The terms "enantiomer" and "enantiomeric" refer to a molecule that cannot be superimposed on its mirror image and hence is optically active wherein the enantiomer rotates the plane of polarized light in one direction and its mirror image compound rotates the plane of polarized light in the opposite direction. An equimolar mixture of two enantiomers is called a "racemic mixture" or a "racemate".

The term "modulate" refers to increasing or decreasing in a test parameter in response to exposure to a Compound of the Invention.

As used herein, the term "stereoisomers" is a general term for all isomers of individual molecules that differ only in the orientation of their atoms in space. It includes enantiomers and isomers of compounds with more than one chiral center that are not mirror images of one another (diastereomers).

The term "chiral center" refers to a carbon atom to which four different groups are attached.

The term "resolution" refers to the separation or concentration or depletion of one of the two enantiomeric forms of a molecule.

The terms "a" and "an" refer to one or more.

The term "treat," "treating" or "treatment" is meant to encompass administering to a subject a Compound of the Invention for the purposes of amelioration or cure, including preemptive and palliative treatment.

The term "about," as used herein in connection with a measured quantity, refers to the normal variations in that measured quantity, as expected by the skilled artisan making the measurement and exercising a level of care commensurate with the objective of measurement and the precision of the measuring equipment.

LIST OF ABBREVIATIONS

AcOH acetic acid
aq. aqueous
° C. degrees Celcius
DCM dichloromethane
DIPEA diisopropylethylamine
DMF dimethylformamide
DMSO dimethylsulfoxide
EDCI 1-ethyl-3-(3-dimethylaminopropyl)carbodiimide)
EtOAc ethyl acetate
EtOH ethanol
h hour(s)
HOBt hydroxybenzotriazole
MeOH methanol
Pd/C palladium on carbon
RT room temperature
satd. saturated Compounds of the Invention The invention provides compounds as delineated infra. In one embodiment, the Compounds of the Invention act as blockers of Na$^+$ channels. Accordingly, these compounds are useful for treating disorders responsive to blockade of sodium ion channels.

In one aspect, the invention provides a compound of Formula I, or a pharmaceutically acceptable salt, solvate, hydrate, or diastereomer thereof:

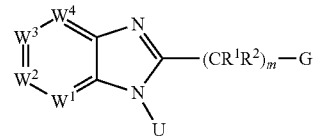

Formula I

Wherein
m is 0, 1, 2, 3, 4, 5, or 6;
n is 0, 1, 2, 3, or 4;
Each of W$^1$, W$^2$, W$^3$, and W$^4$, independently, is C(R$^3$) or N, provided that at least one of W$^1$, W$^2$, W$^3$, and W$^4$ is C(R$^3$);
G is H, alkyl, alkoxy, amino, amide, aryl, cycloalkyl, R$^6$OC(O)—, R$^6$C(O)O—, (R$^6$)$_2$NC(O)O—, heterocyclyl, heteroaryl, or sulfonamide, wherein each of the alkyl, alkoxy, amino, amide, aryl, cycloalkyl, heterocyclyl, heteroaryl, R$^6$OC(O)—, R$^6$C(O)O—, (R$^6$)$_2$NC(O)O—, and sulfonamide is optionally substituted;
U is optionally-substituted naphthyl or

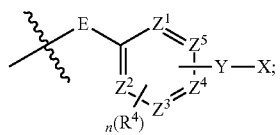

Each of Z$^1$, Z$^2$, Z$^3$, Z$^4$, and Z$^5$, independently, is CH or N, provided that at most three of Z$^1$, Z$^2$, Z$^3$, Z$^4$, and Z$^5$ can be N at the same time;

—Y—X is selected from the group consisting of
a) —O—($C_{0-3}$)alkyl-X, which is optionally substituted;
b) —($C_{0-3}$)alkyl-S—X, which is optionally substituted;
c) —S—($C_{1-3}$)alkyl-X, which is optionally substituted;
d) —($C_{0-3}$)alkyl-S(O)—X, which is optionally substituted;
e) —S(O)—($C_{1-3}$)alkyl-X, which is optionally substituted;
f) —($C_{0-3}$)alkyl-S(O)$_2$—X, which is optionally substituted;
g) —S(O)$_2$—($C_{1-3}$)alkyl-X, which is optionally substituted;
h) —($C_{1-3}$)alkyl-N($R^5$)—X, which is optionally substituted;
i) —($C_{1-3}$)alkyl-N($R^5$)C(O)—X, which is optionally substituted;
j) —($C_{1-3}$)alkyl-C(O)N($R^5$)—X, which is optionally substituted; and
l) —($C_{1-6}$)alkyl-X, which is optionally substituted;
X is optionally-substituted aryl or optionally-substituted heteroaryl;
E is a bond (i.e., absent) or carbonyl;
$R^1$ and $R^2$, each independently, are H, alkyl, amide, amino, cyano, alkoxy, hydroxyl, halogen, cycloalkyl, aryl, heteroaryl, or heterocyclyl, wherein each of the alkyl, alkoxy, amide, amino, cycloalkyl, aryl, heteroaryl, and heterocyclyl is optionally substituted;
$R^3$ and $R^4$, each independently, are H, alkyl, alkoxy, amide, amino, $R^6$OC(O)—, $R^6$C(O)O—, ($R^6$)$_2$NC(O)O—, cyano, cycloalkyl, heterocyclyl, hydroxyl, halogen, sulfonamide, or nitro, wherein each of said alkyl, alkoxy, amide, amino, $R^6$OC(O)—, $R^6$C(O)O—, ($R^6$)$_2$NC(O)O—, cycloalkyl, heterocyclyl, and sulfonamide groups is optionally substituted;
$R^5$, on each occurrence, independently is H, alkyl, cycloalkyl, heterocyclyl, (alkyl)carbonyl, or (amino)carbonyl, wherein each of the alkyl, cycloalkyl, heterocyclyl, (alkyl)carbonyl, and (amino)carbonyl is optionally substituted; and
$R^6$, on each occurrence, independently is H, alkyl, aryl, cycloalkyl, heteroaryl, or heterocyclyl, wherein each of said alkyl, aryl, cycloalkyl, heteroaryl, and heterocyclyl is optionally substituted;
Provided that
i) when U is

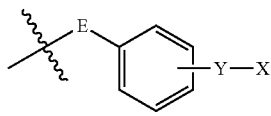

and —Y—X is —O—CH$_2$—X, then X is further substituted by a group other than H;
ii) when U is

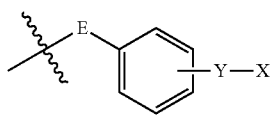

and —Y—X is —O—X, then G is alkoxy, amino, amide, aryl, cycloalkyl, $R^6$OC(O)—, $R^6$C(O)O—, ($R^6$)$_2$NC(O)O—, heterocyclyl, heteroaryl, or sulfonamide, wherein each of said alkoxy, amino, amide, aryl, cycloalkyl, heterocyclyl, heteroaryl, $R^6$OC(O)—, $R^6$C(O)O—, ($R^6$)$_2$NC(O)O—, and sulfonamide is optionally substituted; and
iii) when U is

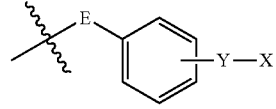

and —Y—X is —($C_{1-6}$)alkyl-X and X is aryl, then said ($C_{1-6}$)alkyl in —Y—X is further optionally substituted by ($C_{1-3}$)alkyl, hydroxyl, halogen, ($C_{1-3}$)alkoxy, amide, amino, (($C_{1-3}$)alkyl)amino, halo ($C_{1-3}$)alkyl, or halo ($C_{1-3}$)alkoxy.

"Optionally-substituted —O—($C_{0-3}$)alkyl-X" as used herein means that the alkyl group therein is optionally substituted by one or more (e.g., one to six) same or different substituents as provided in the definition section. Likewise, optionally-substituted "—($C_{0-3}$)alkyl-S—X", optionally-substituted "—S—($C_{1-3}$)alkyl-X", optionally-substituted "—($C_{0-3}$)alkyl-S(O)—X", optionally-substituted "—S(O)—($C_{1-3}$)alkyl-X", optionally-substituted "($C_{0-3}$)alkyl-S(O)$_2$—X", optionally-substituted "—S(O)$_2$—($C_{1-3}$)alkyl-X", optionally-substituted "—($C_{1-3}$)alkyl-N($R^5$)—X", optionally-substituted "—($C_{1-3}$)alkyl-N($R^5$)C(O)—X", optionally-substituted "—($C_{1-3}$)alkyl-C(O)N($R^5$)—X", and optionally-substituted "—($C_{1-6}$)alkyl-X" mean that the alkyl groups in these moieties are optionally substituted by one or more (e.g., one to six) same or different substituents as provided in the definition section.

In one embodiment, U is

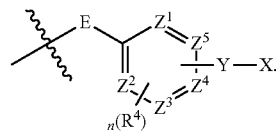

In certain embodiments, the compounds of Formula I have at least three of $Z^1$, $Z^2$, $Z^3$, $Z^4$, and $Z^5$ being CH. One embodiment provides that each of $Z^1$, $Z^2$, $Z^3$, $Z^4$, and $Z^5$ is CH.

In one embodiment of Formula I, at least three of $W^1$, $W^2$, $W^3$, and $W^4$, independently, are C($R^3$). In another embodiment, each of $W^1$, $W^2$, $W^3$, and $W^4$, independently, is C($R^3$). In one embodiment, each of $W^1$, $W^2$, $W^3$, and $W^4$ is CH.

In certain embodiments of the compounds of Formula I, G is alkyl, alkoxy, amino, amide, aryl, cycloalkyl, $R^6$OC(O)—, $R^6$C(O)O—, ($R^6$)$_2$NC(O)O—, heterocyclyl, heteroaryl, or sulfonamide, which is further optionally substituted by one or more (e.g., one to three) substituents independently (when applicable) selected from the group consisting of halogen, hydroxyl, alkoxy, nitro, cyano, haloalkoxy, alkyl, (amino)alkyl, haloalkyl, hydroxyalkyl, (dihydroxy)alkyl (also referred to as "diolalkyl"), (alkyl)carbonyl, (alkyl)sulfonyl, (aryl)sulfonyl, carboxamido, (carboxamido)alkyl, (carboxy)alkyl, (alkoxy)carbonyl, ureido, guanidino, carboxy, carboxyalkyl, cycloalkyl, alkenyl, alkynyl, aryloxy, aralkyloxy, alkylthio, sulfonamido, arylcarbonyl, and the like. In certain embodiments, all of the above optional substituents for G are further optionally substituted by one or more (e.g., one to three) moieties independently selected from halogen, (hydroxyl)alkyl, alkoxy, (carboxy)alkyl, (sulfonamido)alkyl, (carboxamido)alkyl, and the like.

For example, non-limiting exemplary G groups include those delineated infra. and those provided as follows:

1) an amino group substituted by (carboxamido)alkyl, which is further optionally substituted by one or more (e.g., one to three) substitutents selected from the group consisting of alkyl, hydroxyalkyl, (carboxy)alkyl, and (carboxamido)($C_{1-3}$)alkyl; for example, G is

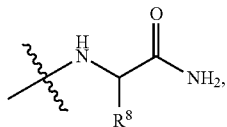

wherein $R^8$ is H, ($C_{1-3}$)alkyl, —($C_{1-3}$)alkyl-OH, —($C_{1-3}$)alkyl-C(O)OH, or —($C_{1-3}$)alkyl-C(O)N($R^7$)$_2$ (definitions for $R^7$ are provided infra.);

2) a 5- or 6-membered heterocyclyl group optionally substituted by carboxamido, (carboxamido)alkyl, alkyl, (alkyl)sulfonyl, (alkyl)carbonyl, carboxy, (alkoxy)carbonyl, or halogen; for example, G is

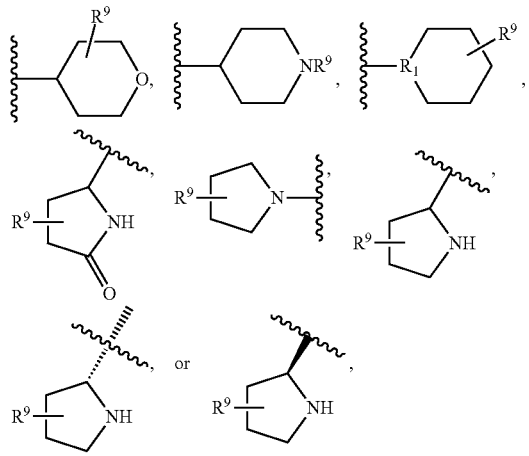

wherein $R^9$ is H, —($C_{1-3}$)alkyl-C(O)NH$_2$, —C($_{1-3}$)alkyl-C(O)N(($C_{1-3}$)alkyl)$_2$, —C(O)OH, —C(O)NH$_2$, —C(O)($C_{1-3}$)alkyl, C(O)O($C_{1-4}$)alkyl, —S(O)$_2$($C_{1-3}$)alkyl, ($C_{1-3}$)alkyl, or halogen;

3) a 5- or 6-membered heteroaryl group optionally substituted by one or two substituents independently selected from carboxamido, (carboxamido)alkyl, haloalkoxy, haloalkyl, halo, and alkyl; for example, G is

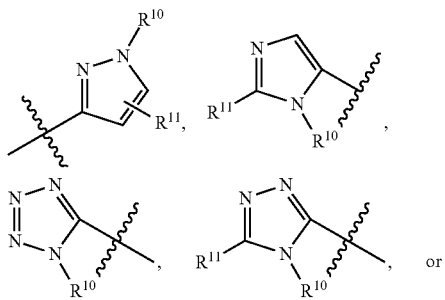

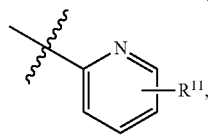

wherein $R^{10}$ is H, ($C_{1-3}$)alkyl, (carboxamido)($C_{1-3}$)alkyl (e.g., —($C_{1-3}$)alkyl-C(O)NH$_2$), or —C(O)NH$_2$; and $R^{11}$ is H, halogen, ($C_{1-3}$)alkyl, halo($C_{1-3}$)alkoxy, or halo($C_{1-3}$)alkyl.

In a separate embodiment of Formula I, X is an aryl group optionally substituted by one or more (e.g., one to three) substituents as above defined. The substituents are also referred to as "M" groups infra. In another embodiment, X is a heteroaryl group optionally substituted by one or more (e.g., one to three) substituents (also referred to as "M" groups herein) as above defined.

In another embodiment, the invention provides a compound of Formula II, or a pharmaceutically acceptable salt, solvate, hydrate, or diastereomer thereof:

Formula II

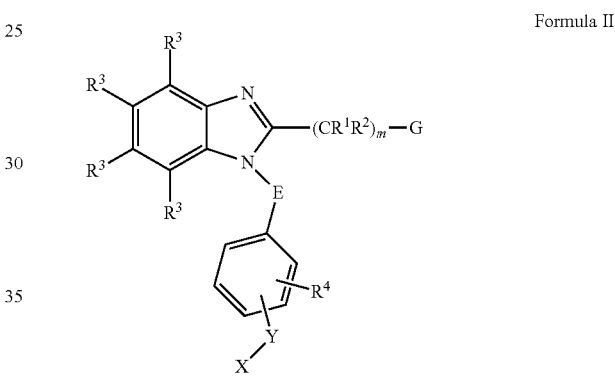

Wherein
m is 0, 1, 2, 3, 4, 5, or 6;
—Y—X is selected from the group consisting of
a) —O—($C_{0-3}$)alkyl-X, which is optionally substituted;
b) —($C_{0-3}$)alkyl-S—X, which is optionally substituted;
c) —S—($C_{1-3}$)alkyl-X, which is optionally substituted; and
d) —($C_{1-6}$)alkyl-X, which is optionally substituted;
X is optionally-substituted aryl or optionally-substituted heteroaryl;
E is a bond or carbonyl;
G is alkoxy, amino, amide, aryl, cycloalkyl, $R^6$OC(O)—, $R^6$C(O)O—, ($R^6$)$_2$NC(O)O—, heterocyclyl, heteroaryl, or sulfonamide, wherein each of the alkoxy, amino, amide, aryl, cycloalkyl, heterocyclyl, heteroaryl, $R^6$OC(O)—, $R^6$C(O)O—, ($R^6$)$_2$NC(O)O—, and sulfonamide is optionally substituted;
$R^1$ and $R^2$, each independently, are H, alkyl, amide, amino, cyano, alkoxy, hydroxyl, halogen, cycloalkyl, aryl, heteroaryl, or heterocyclyl, wherein each of the alkyl, alkoxy, amide, amino, cycloalkyl, aryl, heteroaryl, and heterocyclyl is optionally substituted;
$R^3$ and $R^4$, each independently, are H, alkyl, alkoxy, amide, amino, $R^6$OC(O)—, $R^6$C(O)O—, cyano, cycloalkyl, heterocyclyl, hydroxyl, halogen, sulfonamide, or nitro, wherein each of said alkyl, alkoxy, amide, amino, $R^6$OC(O)—, $R^6$C(O)O—, cycloalkyl, heterocyclyl, and sulfonamide groups is optionally substituted; and $R^6$, on each occurrence, independently is H, alkyl, aryl, cycloalkyl, heteroaryl, or heterocyclyl, wherein each of said alkyl, aryl, cycloalkyl, heteroaryl, and heterocyclyl is optionally substituted;

Provided that when —Y—X is —O—CH$_2$—X, then X is further substituted (i.e., by a group other than H); and when —Y—X is —(C$_{1-6}$)alkyl-X and X is aryl, then said (C$_{1-6}$)alkyl in —Y—X is further optionally substituted by (C$_{1-3}$)alkyl, hydroxyl, halogen, (C$_{1-3}$)alkoxy, amide, amino, ((C$_{1-3}$)alkyl)amino, halo(C$_{1-3}$)alkyl, or (C$_{1-3}$)alkoxy.

In certain embodiments, the Compounds of the Invention are compounds of any one of Formulae I and II, wherein E is a bond, and pharmaceutically acceptable salts, solvates, hydrates, or diastereomers thereof.

In one embodiment of Formula I or II, all $R^3$s are hydrogen.

In a separate embodiment of Formula I or II, $R^4$ is H.

In another embodiment, the invention provides a compound of Formula III, or a pharmaceutically acceptable salt, solvate, hydrate, or diastereomer thereof:

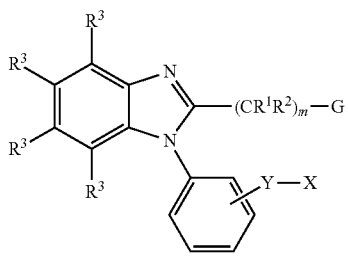

Formula III

Wherein
m is 0, 1, 2, 3, or 4;
—Y—X is selected from the group consisting of
a) —O—(C$_{0-3}$)alkyl-X, which is optionally substituted;
b) —(C$_{0-3}$)alkyl-S—X, which is optionally substituted; and
c) —S—(C$_{1-3}$)alkyl-X, which is optionally substituted;

X is optionally-substituted aryl or optionally-substituted heteroaryl;

G is alkoxy, amino, amide, aryl, cycloalkyl, $R^6$OC(O)—, $R^6$C(O)O—, (R$^6$)$_2$NC(O)O—, heterocyclyl, heteroaryl, or sulfonamide, wherein each of the alkoxy, amino, amide, aryl, cycloalkyl, heterocyclyl, heteroaryl, $R^6$OC(O)—, $R^6$C(O)O—, (R$^6$)$_2$NC(O)O—, and sulfonamide is optionally substituted;

$R^1$ and $R^2$, each independently, are H, alkyl, amide, amino, cyano, alkoxy, hydroxyl, halogen, cycloalkyl, aryl, heteroaryl, or heterocyclyl, wherein each of the alkyl, alkoxy, amide, amino, cycloalkyl, aryl, heteroaryl, and heterocyclyl is optionally substituted;

$R^3$ each independently is H, alkyl, alkoxy, amide, amino, $R^6$OC(O)—, $R^6$C(O)O—, cyano, cycloalkyl, heterocyclyl, hydroxyl, halogen, sulfonamide, or nitro, wherein each of said alkyl, alkoxy, amide, amino, $R^6$OC(O)—, $R^6$C(O)O—, cycloalkyl, heterocyclyl, and sulfonamide groups is optionally substituted; and $R^6$, on each occurrence, independently is H, alkyl, aryl, cycloalkyl, heteroaryl, or heterocyclyl, wherein each of said alkyl, aryl, cycloalkyl, heteroaryl, and heterocyclyl is optionally substituted;

Provided that when —Y—X is —O—CH$_2$—X, then X is further substituted by a group other than H.

In one embodiment of the compounds of any one of Formulae I to III, at least three of $R^3$s are hydrogen.

In another embodiment, the Compounds of the Invention are compounds of Formula IV, and pharmaceutically acceptable salts, solvates, hydrates, and diastereomers thereof:

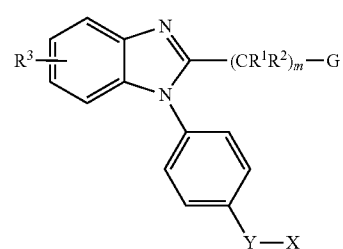

Formula IV

Wherein
m is 0, 1, 2, or 3;
—Y—X is —O—(C$_{0-3}$)alkyl-X;
X is optionally-substituted aryl or optionally-substituted heteroaryl;
$R^1$ and $R^2$, each independently, are H, optionally-substituted 3 to 7-membered heterocyclyl, or optionally-substituted (C$_{1-6}$)alkyl;
G is selected from the group consisting of alkoxy, amino, cycloalkyl, heterocyclyl, and heteroaryl, and
i) when G is alkoxy, cycloalkyl, heterocyclyl, or heteroaryl, then each of the alkoxy, cycloalkyl, heterocyclyl, and heteroaryl is further optionally substituted by one or more (e.g., one to three) substituents independently selected from the group consisting of:
a) —(C$_{0-6}$)alkyl-C(O)N(R$^7$)$_2$ optionally substituted by one or more (e.g., one to three) substituents independently selected from the group consisting of —(C$_{1-3}$)alkyl, —(C$_{0-3}$)alkyl-OH, (C$_{1-3}$)alkoxy, —(C$_{0-3}$)alkyl-C(O)OH, —(C$_{0-3}$)alkyl-S(O)$_2$NH$_2$, and —(C$_{0-3}$)alkyl-C(O)N(R$^7$)$_2$;
b) (C$_{1-6}$)alkyl optionally substituted by one or more (e.g., one to three) substituents independently selected from the group consisting of hydroxyl, —NH$_2$, —(C$_{0-3}$)alkyl-OH, halogen, —(C$_{0-3}$)alkyl-C(O)OH, and —(C$_{0-3}$)alkyl-C(O)N(R$^7$)$_2$;
c) (C$_{1-6}$)alkoxy optionally substituted by one or more (e.g., one to three) same or different halogens;
d) —OH;
e) ureido;
f) halogen;
g) —C(O)(C$_{1-6}$)alkyl;
h) —C(O)O(C$_{1-6}$)alkyl;
i) —S(O)$_2$(C$_{1-6}$)alkyl; and
j) —S(O)$_2$N(R$^7$)$_2$;
ii) when G is amino, said amino is further optionally substituted by one or two substituents independently selected from the group consisting of:
1) —(C$_{0-6}$)alkyl-C(O)N(R$^7$)$_2$ optionally substituted by one or more (e.g., one to three) substituents independently selected from the group consisting of (C$_{1-3}$)alkyl, —(C$_{0-3}$)alkyl-OH, (C$_{1-3}$)alkoxy, —(C$_{0-3}$)alkyl-C(O)OH, —(C$_{0-3}$)alkyl-S(O)$_2$NH$_2$, and —(C$_{0-3}$)alkyl-C(O)NH$_2$;
2) (C$_{1-6}$)alkyl optionally substituted by one or more (e.g., one to three) substituents selected from the group consisting of $(C_{1-3})$alkyl, hydroxyl, —NH$_2$, —$(C_{0-3})$alkyl-OH, halogen, —$(C_{0-3})$alkyl-C(O)OH, and —$(C_{0-3})$alkyl-C(O)N(R$^7$)$_2$;

3) —C(O)(C$_{1-6}$)alkyl;
4) —C(O)O(C$_{1-6}$)alkyl; and
5) —S(O)$_2$(C$_{1-6}$)alkyl;

R$^7$, each independently, is H or (C$_{1-6}$)alkyl;

R$^3$ is H, (C$_{1-6}$)alkyl, (C$_{1-6}$)alkoxy, amide, amino, R$^6$OC(O)—, R$^6$C(O)O—, cyano, (C$_{3-7}$)cycloalkyl, 4- to 8-membered heterocyclyl, hydroxyl, halogen, sulfonamide, or nitro, wherein each of said (C$_{1-6}$)alkyl, (C$_{1-6}$)alkoxy, amide, amino, R$^6$OC(O)—, R$^6$C(O)O—, (C$_{3-7}$)cycloalkyl, 4- to 8-membered heterocyclyl, and sulfonamide groups is optionally substituted; and R$^6$, on each occurrence, independently is H, (C$_{1-6}$)alkyl, 6- to 10-membered aryl, (C$_{3-7}$)cycloalkyl, 5- to 6-membered heteroaryl, or 4- to 8-membered heterocyclyl, wherein each of said (C$_{1-6}$)alkyl, said 6- to 10-membered aryl, said (C$_{3-7}$)cycloalkyl, said 5- to 6-membered heteroaryl, and said 4- to 8-membered heterocyclyl is optionally substituted;

Provided that when —Y—X is —O—CH$_2$—X, then X is further substituted (i.e., by a group other than H).

One embodiment of the compounds in accordance with any one of Formulae I to IV provides that —Y—X is —O—X. In another embodiment, —Y—X is —O—(C$_{1-3}$)alkyl-X.

In one embodiment of Formulae I to IV, one of R$^1$ and R$^2$ is H, and the other is H, optionally-substituted 3- to 7-membered heterocyclyl (e.g.,

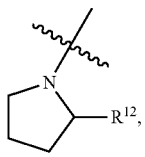

wherein R$^{12}$ is H, (C$_{1-3}$)alkyl, or carboxamido), or (C$_{1-3}$)alkyl (e.g., methyl and ethyl).

In a separate embodiment, the invention provides the compounds of any one of Formulae I to IV, and pharmaceutically acceptable salts, solvates, hydrates, and diastereomers thereof, wherein X is phenyl or 6-membered heteroaryl, with each of said phenyl and said 6-membered heteroaryl being optionally substituted. For example, X can be phenyl, pyridyl, or pyrimidyl, wherein each of said phenyl, pyridyl, and pyrimidyl is optionally substituted.

In one instance, X is phenyl that is optionally substituted by one to three same or different substituents. The substituents include any aryl substituents as above discussed. In one embodiment, the substituents are selected from the group consisting of halogen, haloalkyl, haloalkoxy, (alkyl)amino, amino, and (dialkyl)amino.

In another embodiment, the Compounds of the Invention are compounds of Formula V, and pharmaceutically acceptable salts, solvates, hydrates, and diastereomers thereof:

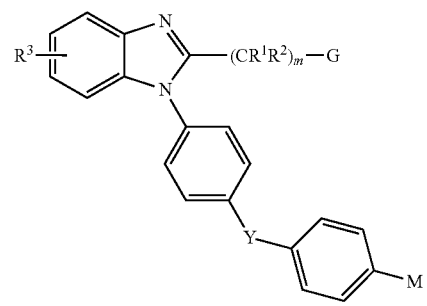

Formula V

Wherein
Y is —O— or —O—CH$_2$—;
m is 0, 1, or 2;
M is halogen, haloalkyl, haloalkoxy, (alkyl)amino, amino, or (dialkyl)amino;
R$^1$ and R$^2$, each independently, are H or (C$_{1-3}$)alkyl;
R$^3$ is H, (C$_{1-3}$)alkyl, (C$_{1-3}$)alkoxy, amino, hydroxyl, or halogen;
G is selected from the group consisting of
i) amino optionally substituted by
  1) —(C$_{0-3}$)alkyl-C(O)N(R$^7$)$_2$ further optionally substituted by one or more (e.g., one to three) substituents independently selected from the group consisting of (C$_{1-3}$)alkyl, —(C$_{0-3}$)alkyl-OH, —(C$_{1-3}$)alkoxy, —(C$_{0-3}$)alkyl-C(O)OH, —(C$_{0-3}$)alkyl-S(O)$_2$NH$_2$, and —(C$_{0-3}$)alkyl-C(O)NH$_2$;
  2) (C$_{1-3}$)alkyl optionally substituted by one or more (e.g., one to three) substituents independently selected from the group consisting of (C$_{1-3}$)alkyl, hydroxyl, —NH$_2$, —(C$_{0-3}$)alkyl-OH, halogen, —(C$_{0-3}$)alkyl-C(O)OH, and —(C$_{0-3}$)alkyl-C(O)N(R$^7$)$_2$;
  3) —C(O)O(C$_{1-3}$)alkyl; or
  4) —C(O)(C$_{1-3}$)alkyl;
ii) 3 to 7-membered heterocyclyl optionally substituted by one or more substituents independently selected from the group consisting of
  a) —(C$_{0-3}$)alkyl-C(O)N(R$^7$)$_2$ further optionally substituted by one or more substituents independently selected from the group consisting of (C$_{1-3}$)alkyl, —(C$_{0-3}$)alkyl-OH, —(C$_{1-3}$)alkoxy, —(C$_{0-3}$)alkyl-C(O)OH, —(C$_{0-3}$)alkyl-S(O)$_2$NH$_2$, and —(C$_{0-3}$)alkyl-C(O)NH$_2$;
  b) (C$_{1-3}$)alkyl optionally substituted by one or more (e.g., one to three) substituents independently selected from the group consisting of (C$_{1-3}$)alkyl, hydroxyl, —NH$_2$, —(C$_{0-3}$)alkyl-OH, halogen, —(C$_{0-3}$)alkyl-C(O)OH, and —(C$_{0-3}$)alkyl-C(O)N(R$^7$)$_2$;
  c) (C$_{1-3}$)alkoxy optionally substituted by one or more (e.g., one to three) same or different halogens;
  d) halogen;
  e) —S(O)$_2$(C$_{1-3}$)alkyl;
  f) —C(O)O(C$_{1-3}$)alkyl; and
  g) —C(O)(C$_{1-3}$)alkyl;
and iii) 5- to 6-membered heteroaryl optionally substituted by one or more (e.g., one to three) substituents independently selected from the group consisting of the a)-g) moieties as above defined; and
R$^7$ independently is H or (C$_{1-3}$)alkyl.

In one embodiment, the Compounds of the Invention are compounds of any one of Formula I to V, and pharmaceutically acceptable salts, solvates, hydrates, and diastereomers thereof, wherein Y is —O—.

In one embodiment, the compounds of Formula V have M as halogen (e.g., F). In another embodiment of Formula V, M is haloalkyl (such as, —CF$_3$).

Certain embodiments in accordance with any one of the above formulae provide that one of R$^1$ and R$^2$ is H, and the other is (C$_{1-3}$)alkyl.

In one embodiment, the Compounds of the Invention are compounds of any one of the above formulae, and pharmaceutically acceptable salts, solvates, hydrates, and diastereomers thereof, wherein G is optionally-substituted 3- to 7-membered heterocyclyl (including those discussed supra.).

Further, non-limiting exemplary 3- to 7-membered heterocyclyl groups that can be used herein as a G group include oxiranyl, aziridinyl, azetidinyl, oxo-azetidinyl, tetrahydrofuranyl, tetrahydro-pyranyl, pyrrolidinyl, oxo-pyrrolidinyl, piperidyl, oxo-piperidyl, and the like.

Moreover, G can be a 3- to 7-membered heterocyclyl moiety that is optionally substituted by one or more (e.g., one, two, or three) substituents independently selected from the group consisting of halogen, optionally-substituted (C$_{1-3}$)alkyl, —C(O)O(C$_{1-3}$) alkyl, —C(O)C$_{(1-3)}$alkyl, —S(O)$_2$(C$_{1-3}$)alkyl, and optionally-substituted —(C$_{0-3}$)alkyl-C(O)N(R$^7$)$_2$.

In one embodiment, G is a 3- to 7-membered heterocyclyl moiety selected from the group consisting of:

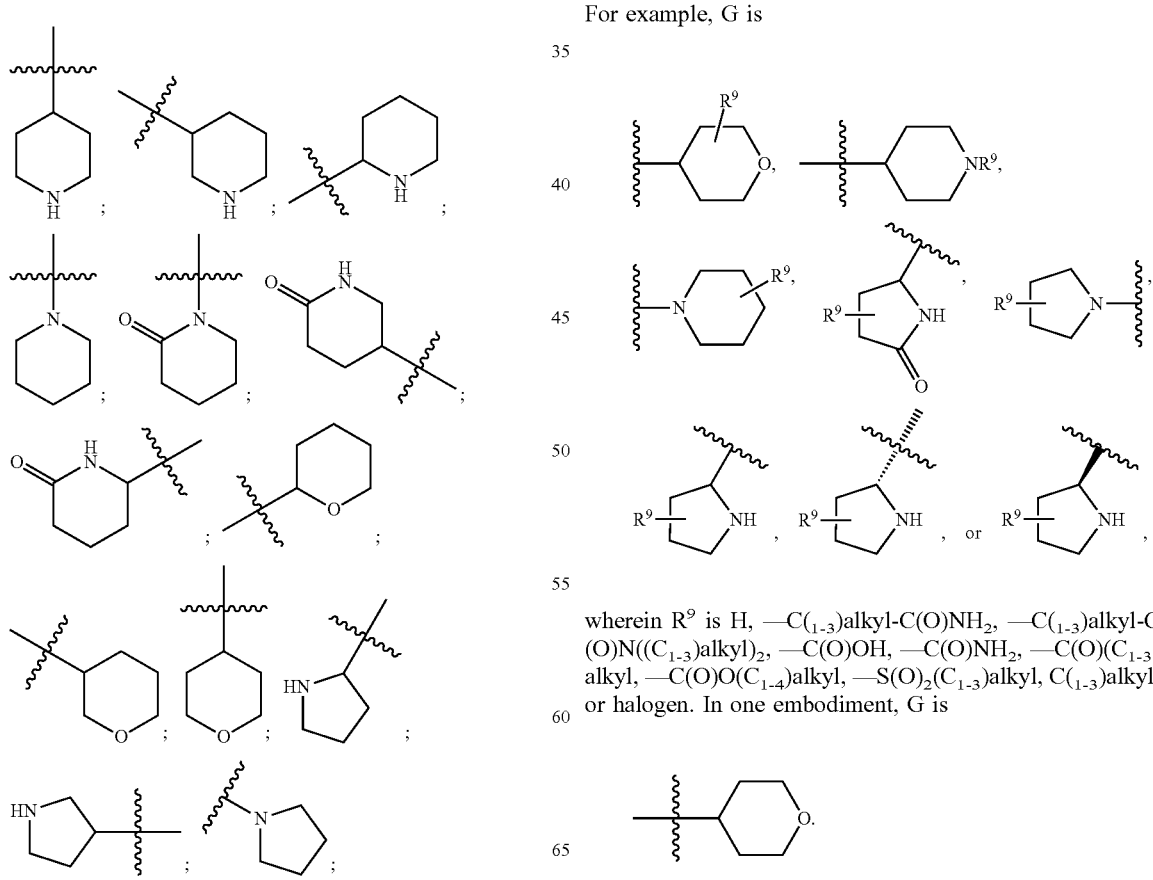

wherein any one of the above 3- to 7-membered heterocyclyl moieties is further optionally substituted by one or two same or different substituents selected from the group consisting of halogen, —(C$_{0-3}$)alkyl-C(O)N(R$^7$)$_2$, —C(O)O(C$_{1-3}$) alkyl, —C(O)(C$_{1-3}$)alkyl, —SO$_2$(C$_{1-3}$)alkyl, and (C$_{1-3}$) alkyl. In certain embodiments, R$^7$, each independently, is H or (C$_{1-3}$)alkyl.

In an embodiment, G is a 5- or 6-membered heterocyclyl group optionally substituted by carboxamido, (carboxamido)alkyl, alkyl, (alkyl)sulfonyl, (alkyl)carbonyl, or halogen. For example, G is

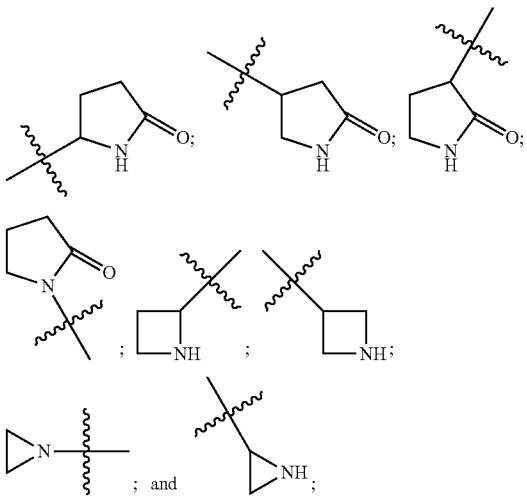

wherein R$^9$ is H, —C$_{(1-3)}$alkyl-C(O)NH$_2$, —C$_{(1-3)}$alkyl-C(O)N((C$_{1-3}$)alkyl)$_2$, —C(O)OH, —C(O)NH$_2$, —C(O)(C$_{1-3}$) alkyl, —C(O)O(C$_{1-4}$)alkyl, —S(O)$_2$(C$_{1-3}$)alkyl, C$_{(1-3)}$alkyl, or halogen. In one embodiment, G is In another embodiment, G is

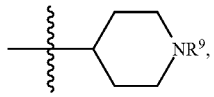

wherein R⁹ is H, —C₍₁₋₃₎alkyl-C(O)NH₂, —C₍₁₋₃₎alkyl-C(O)N((C₁₋₃)alkyl)₂, or —C(O)O(C₁₋₄)alkyl. In still another embodiment, G is

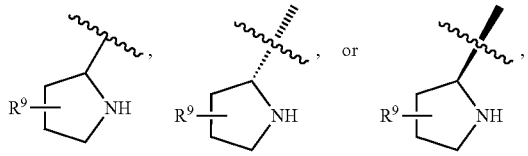

wherein R⁹ is H, —C₍₁₋₃₎alkyl-C(O)NH₂, —C(O)NH₂, or —C(O)O(C₁₋₄)alkyl. In another embodiment, G is

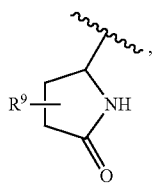

wherein R⁹ is H, —C(O)NH₂, or —C(O)OH.

In another embodiment, the Compounds of the Invention are compounds of any one of the above formulae, and pharmaceutically acceptable salts, solvates, hydrates, and diastereomers thereof, wherein G is a heteroaryl group including those discussed supra.

Further, as a separate embodiment, G is an optionally-substituted 5- to 6-membered heteroaryl moiety selected from the group consisting of furanyl, thiophenyl, imidazyl, triazolyl, triazinyl, tetrazolyl, pyrazolyl, pyridinyl, and pyrimidyl, each of which is further optionally substituted by one or more (e.g., one to three) substituents independently selected from the group consisting of halogen, optionally-substituted (C₁₋₃)alkyl, halo(C₁₋₃)alkoxy, and optionally-substituted —(C₀₋₃)alkyl-C(O)N(R⁷)₂. In one embodiment, R⁷ as used herein, each independently, is H or (C₁₋₃)alkyl.

Non-limiting exemplary 5- to 6-membered heteroaryl groups that can be used as G include those provided as follows:

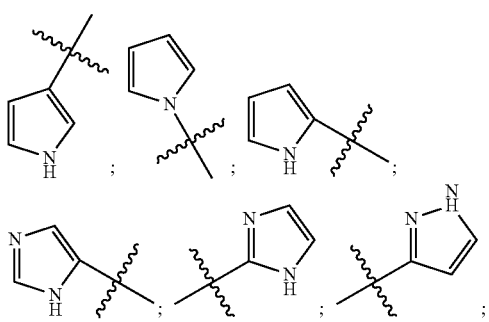

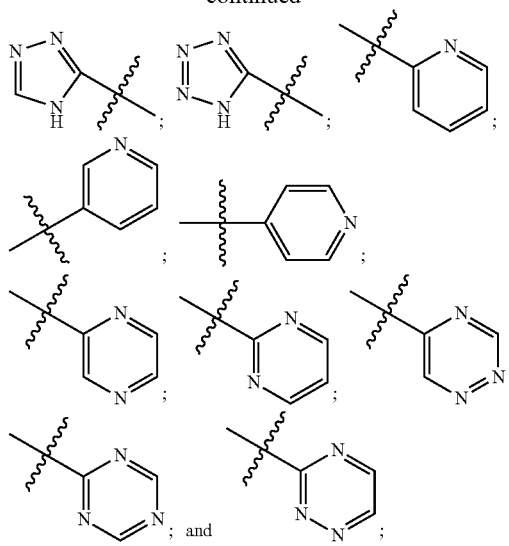

wherein each of the above exemplified 5- to 6-membered heteroaryl groups is further optionally substituted by one or more (e.g., one to three) substituents independently selected from the group consisting of halogen, (C₁₋₃)alkyl, —(C₀₋₃)alkyl-C(O)N(R⁷)₂, halo(C₁₋₃)alkyl, and halo(C₁₋₃)alkoxy. In one embodiment, R⁷ as used herein, each independently, is H or (C₁₋₃)alkyl.

In another embodiment, G is a 5- or 6-membered heteroaryl group optionally substituted by one or two substituents independently selected from the group consisting of carboxamido, (carboxamido)alkyl, haloalkoxy, haloalkyl, halo, and alkyl.

For example, G is

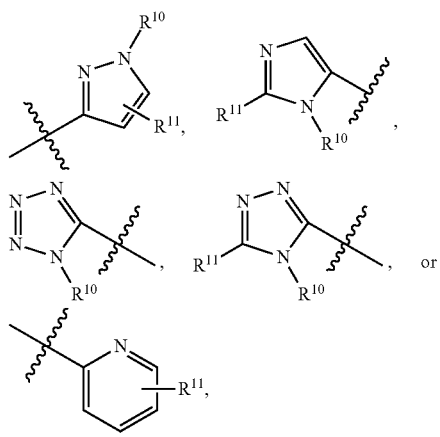

wherein R¹⁰ is H, (C₁₋₃)alkyl, —(C₁₋₃)alkyl-C(O)NH₂, or —C(O)NH₂; and R^H is H, halogen, (C₁₋₃)alkyl, halo(C₁₋₃)alkoxy, or halo(C₁₋₃)alkyl.

In still another embodiment, the Compounds of the Invention are compounds of any one of the above formulae, and pharmaceutically acceptable salts, solvates, hydrates, and diastereomers thereof, wherein G is optionally-substituted amino (including those above delineated). As a further example, G is —NH(C₁₋₃)alkyl that may be further optionally substituted by one or more (e.g., one to three) substituents, which can be the same or different. Non-limiting exemplary substituents include $(C_{1-3})$alkyl, $—C(O)N(R^7)_2$, —OH, and —C(O)OH. In one embodiment, $R^7$ as used herein, each independently, is H or $(C_{1-3})$alkyl.

In other embodiments, G is an amino group substituted by (carboxamido)alkyl, which is further optionally substituted by one or more (e.g., one to three) substituents selected from the group consisting of $(C_{1-3})$alkyl, $—(C_{1-3})$alkyl-OH, $—(C_{0-3})$alkyl-C(O)OH, and $—(C_{0-3})$alkyl-C(O)N(R^7)_2$.

For example, G is

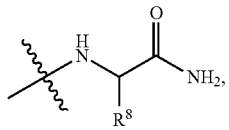

wherein $R^8$ is H, $(C_{1-3})$alkyl, $—(C_{1-3})$alkyl-OH, $—(C_{1-3})$alkyl-C(O)OH, or $—(C_{1-3})$alkyl-C(O)N(R^7)_2$. One embodiment provides that $R^7$ is H.

Further, non-limiting exemplary optionally-substituted amino groups that can be used as G include, for example, the following moieties:

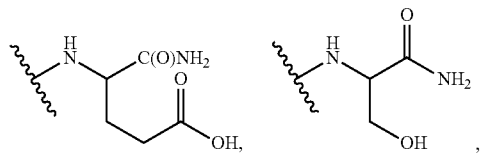

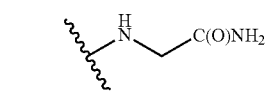

In one embodiment, the Compounds of the Invention are compounds having any one of the above formulae, wherein $R^3$ is H, and the pharmaceutically acceptable salts, solvates, hydrates, and diastereomers thereof.

In certain embodiments, the Compounds of the Invention include exemplary compounds provided in TABLE 2 as follows:

TABLE 2

| Compd No. | Structure | Chemical Name |
|---|---|---|
| 9 | 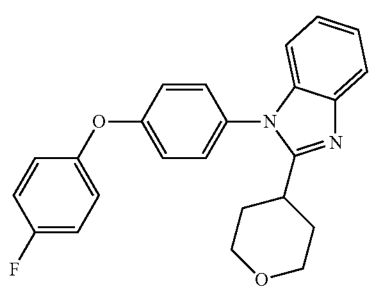 [SMILES: Fc1ccc(Oc2ccc(-n3c(C4CCOCC4)nc4ccccc43)cc2)cc1] | 1-(4-(4-fluorophenoxy)phenyl)-2-(tetrahydro-2H-pyran-4-yl)-1H-benzo[d]imidazole |
| 10 | 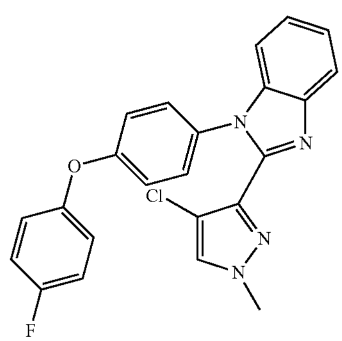 [SMILES: Cn1cc(Cl)c(-c2nc3ccccc3n2-c2ccc(Oc3ccc(F)cc3)cc2)n1] | 2-(4-chloro-1-methyl-1H-pyrazol-3-yl)-1-(4-(4-fluorophenoxy)phenyl)-1H-benzo[d]imidazole |

TABLE 2-continued
| Compd No. | Structure | Chemical Name |
|---|---|---|
| 11 | 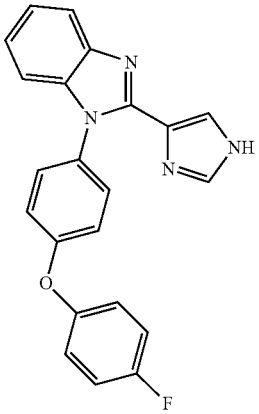 [SMILES: Fc1ccc(Oc2ccc(-n3c(-c4c[nH]cn4)nc4ccccc43)cc2)cc1] | 1-(4-(4-fluorophenoxy)phenyl)-2-(1H-imidazol-4-yl)-1H-benzo[d]imidazole |
| 14 | 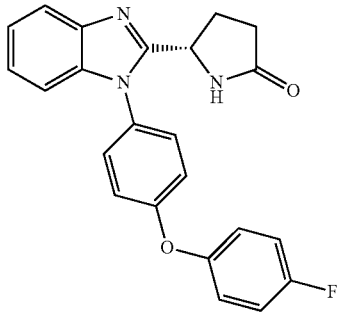 [SMILES: O=C1CC[C@@H](c2nc3ccccc3n2-c2ccc(Oc3ccc(F)cc3)cc2)N1] | (S)-5-(1-(4-(4-fluorophenoxy)-phenyl)-1H-benzo[d]imidazol-2-yl)pyrrolidin-2-one |
| 15 | 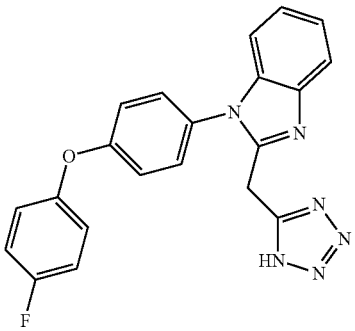 [SMILES: Fc1ccc(Oc2ccc(-n3c(Cc4nnn[nH]4)nc4ccccc43)cc2)cc1] | 2-((1H-tetrazol-5-yl)methyl)-1-(4-(4-fluorophenoxy)phenyl)-1H-benzo[d]imidazole |
| 16 | 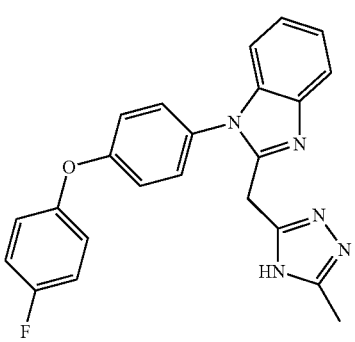 [SMILES: Cc1nnc(Cc2nc3ccccc3n2-c2ccc(Oc3ccc(F)cc3)cc2)[nH]1] | 1-(4-(4-fluorophenoxy)phenyl)-2-((5-methyl-4H-1,2,4-triazol-3-yl)methyl)-1H-benzo[d]imidazole |

TABLE 2-continued

| Compd No. | Structure | Chemical Name |
|---|---|---|
| 17 | 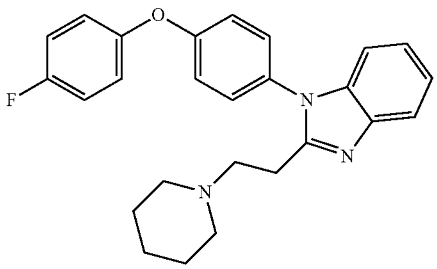 [SMILES: Fc1ccc(Oc2ccc(-n3c(CCN4CCCCC4)nc4ccccc43)cc2)cc1] | 1-(4-(4-fluorophenoxy)phenyl)-2-(2-(piperidin-1-yl)ethyl)-1H-benzo[d]imidazole |
| 18 | 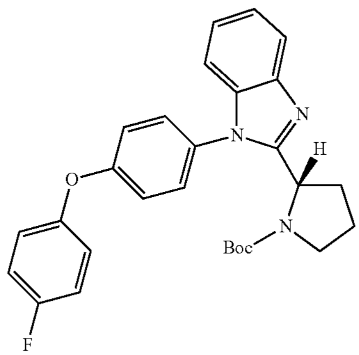 [SMILES: CC(C)(C)OC(=O)N1CCC[C@H]1c1nc2ccccc2n1-c1ccc(Oc2ccc(F)cc2)cc1] | tert-butyl (S)-2-(1-(4-(4-fluorophenoxy)phenyl)-1H-benzo[d]imidazol-2-yl)pyrrolidine-1-carboxylate |
| 19 | 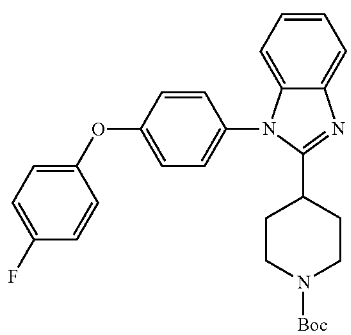 [SMILES: CC(C)(C)OC(=O)N1CCC(c2nc3ccccc3n2-c2ccc(Oc3ccc(F)cc3)cc2)CC1] | tert-butyl 4-(1-(4-(4-fluorophenoxy)phenyl)-1H-benzo[d]imidazol-2-yl)piperidine-1-carboxylate |
| 20 | 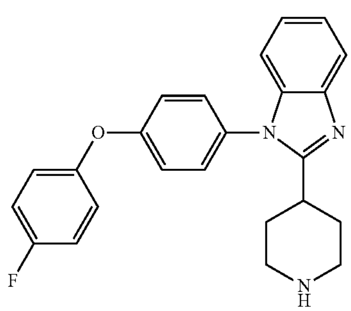 [SMILES: Fc1ccc(Oc2ccc(-n3c(C4CCNCC4)nc4ccccc43)cc2)cc1] | 1-(4-(4-fluorophenoxy)phenyl)-2-(piperidin-4-yl)-1H-benzo[d]imidazole |
| 21 | 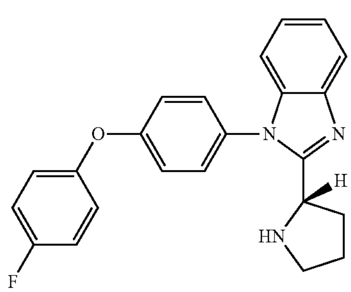 [SMILES: Fc1ccc(Oc2ccc(-n3c([C@@H]4CCCN4)nc4ccccc43)cc2)cc1] | (S)-1-(4-(4-fluorophenoxy)phenyl)-2-(pyrrolidin-2-yl)-1H-benzo[d]imidazole |

TABLE 2-continued

| Compd No. | Structure | Chemical Name |
|---|---|---|
| 23 | 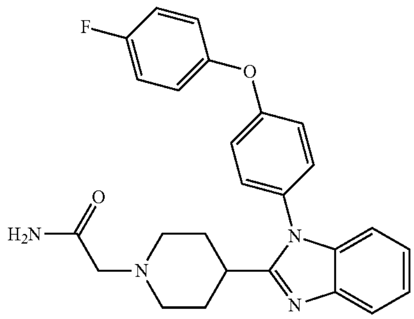 [SMILES: NC(=O)CN1CCC(c2nc3ccccc3n2-c2ccc(Oc3ccc(F)cc3)cc2)CC1] | 2-(4-(1-(4-(4-fluorophenoxy)phenyl)-1H-benzo[d]imidazol-2-yl)piperidin-1-yl)acetamide |
| 24 | 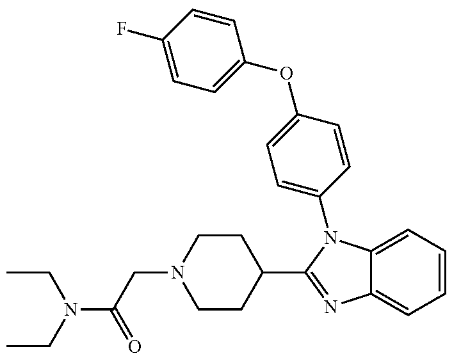 [SMILES: CCN(CC)C(=O)CN1CCC(c2nc3ccccc3n2-c2ccc(Oc3ccc(F)cc3)cc2)CC1] | N,N-diethyl-2-(4-(1-(4-(4-fluorophenoxy)phenyl)-1H-benzo[d]imidazol-2-yl)piperidin-1-yl)acetamide |
| 25 | 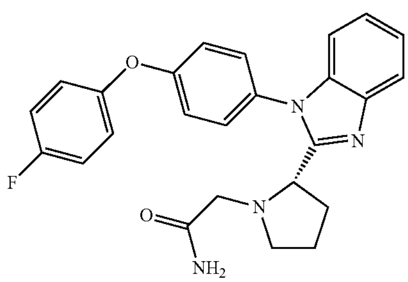 [SMILES: NC(=O)CN1CCC[C@H]1c1nc2ccccc2n1-c1ccc(Oc2ccc(F)cc2)cc1] | (S)-2-(2-(1-(4-(4-fluorophenoxy)phenyl)-1H-benzo[d]imidazol-2-yl)pyrrolidin-1-yl)acetamide |
| 26 | 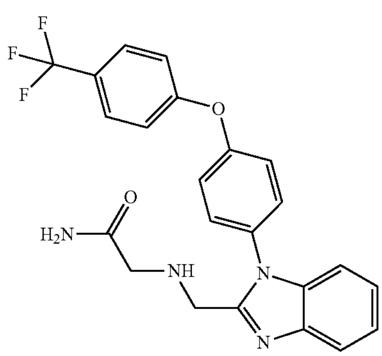 [SMILES: NC(=O)CNCc1nc2ccccc2n1-c1ccc(Oc2ccc(C(F)(F)F)cc2)cc1] | 2-(((1-(4-(4-(trifluoromethyl)phenoxy)phenyl)-1H-benzo[d]imidazol-2-yl)methyl)amino)-acetamide |

TABLE 2-continued

| Compd No. | Structure | Chemical Name |
|---|---|---|
| 27 | 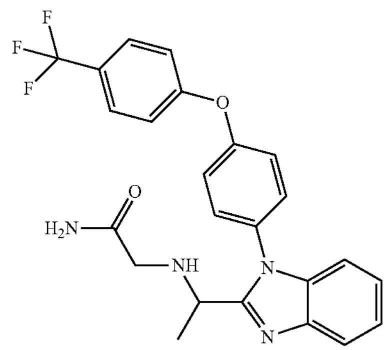 [SMILES: CC(NCC(N)=O)c1nc2ccccc2n1-c1ccc(Oc2ccc(C(F)(F)F)cc2)cc1] | 2-((1-(1-(4-(4-(trifluoromethyl)phenoxy)phenyl)-1H-benzo[d]imidazol-2-yl)ethyl)amino)acetamide |
| 28 | 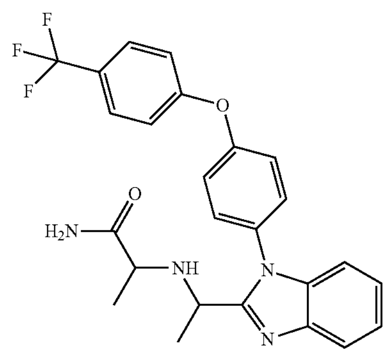 [SMILES: CC(NC(C)c1nc2ccccc2n1-c1ccc(Oc2ccc(C(F)(F)F)cc2)cc1)C(N)=O] | 2-((1-(1-(4-(4-(trifluoromethyl)phenoxy)phenyl)-1H-benzo[d]imidazol-2-yl)ethyl)amino)propanamide |
| 29 | 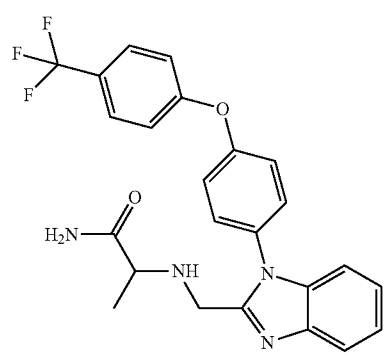 [SMILES: CC(NCc1nc2ccccc2n1-c1ccc(Oc2ccc(C(F)(F)F)cc2)cc1)C(N)=O] | 2-(((1-(4-(4-(trifluoromethyl)phenoxy)phenyl)-1H-benzo[d]imidazol-2-yl)methyl)amino)propanamide |
| 30 | 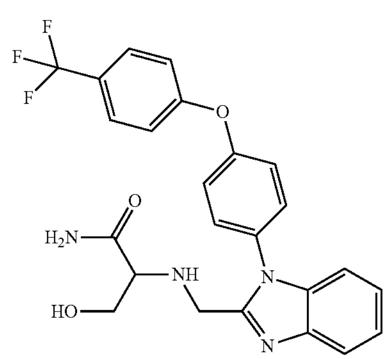 [SMILES: NC(=O)C(CO)NCc1nc2ccccc2n1-c1ccc(Oc2ccc(C(F)(F)F)cc2)cc1] | 3-hydroxy-2-(((1-(4-(4-(trifluoromethyl)phenoxy)phenyl)-1H-benzo[d]imidazol-2-yl)methyl)-amino)propanamide |

TABLE 2-continued

| Compd No. | Structure | Chemical Name |
|---|---|---|
| 31 | 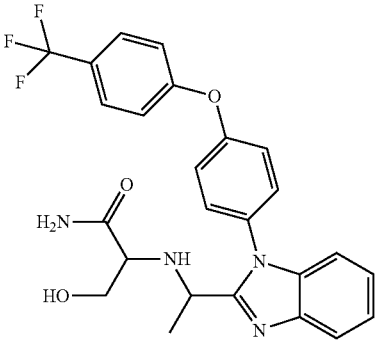 [SMILES: CC(NC(CO)C(N)=O)c1nc2ccccc2n1-c1ccc(Oc2ccc(C(F)(F)F)cc2)cc1] | 3-hydroxy-2-((1-(1-(4-(4-(trifluoromethyl)phenoxy)phenyl)-1H-benzo[d]imidazol-2-yl)ethyl)amino)propanamide |
| 32 | 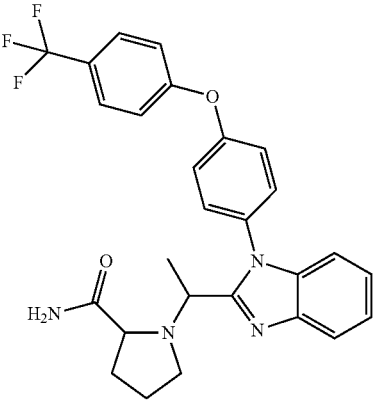 [SMILES: CC(c1nc2ccccc2n1-c1ccc(Oc2ccc(C(F)(F)F)cc2)cc1)N1CCCC1C(N)=O] | 1-(1-(1-(4-(4-(trifluoromethyl)phenoxy)phenyl)-1H-benzo[d]imidazol-2-yl)ethyl)pyrrolidine-2-carboxamide |
| 33 | 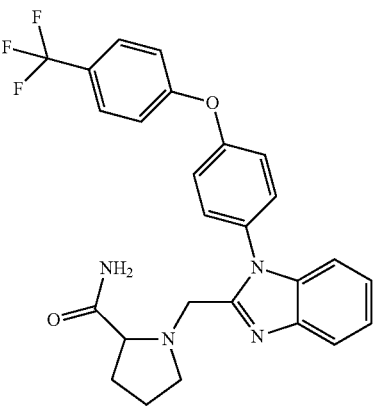 [SMILES: NC(=O)C1CCCN1Cc1nc2ccccc2n1-c1ccc(Oc2ccc(C(F)(F)F)cc2)cc1] | 1-((1-(4-(4-(trifluoromethyl)phenoxy)phenyl)-1H-benzo[d]imidazol-2-yl)methyl)pyrrolidine-2-carboxamide |
| 34 | 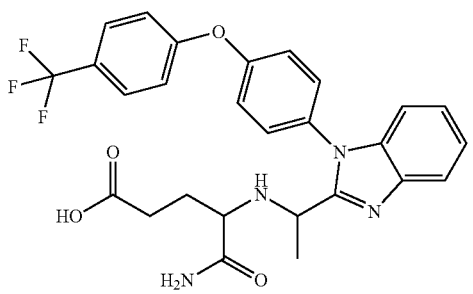 [SMILES: CC(NC(CCC(=O)O)C(N)=O)c1nc2ccccc2n1-c1ccc(Oc2ccc(C(F)(F)F)cc2)cc1] | 5-amino-5-oxo-4-((1-(1-(4-(4-(trifluoromethyl)phenoxy)phenyl)-1H-benzo[d]imidazol-2-yl)ethyl)-amino)pentanoic acid |

TABLE 2-continued

| Compd No. | Structure | Chemical Name |
|---|---|---|
| 35 | 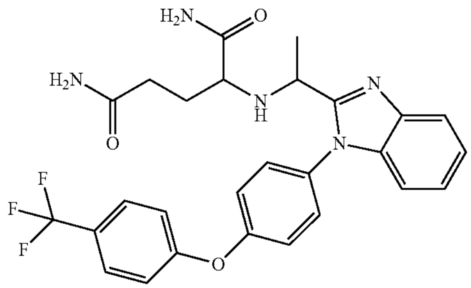 [SMILES: CC(NC(CCC(N)=O)C(N)=O)c1nc2ccccc2n1-c1ccc(Oc2ccc(C(F)(F)F)cc2)cc1] | 2-((1-(1-(4-(4-(trifluoromethyl)phenoxy)phenyl)-1H-benzo[d]imidazol-2-yl)ethyl)amino)pentanediamide |
| 36 | 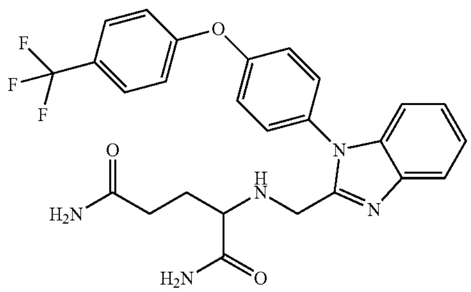 [SMILES: NC(=O)CCC(NCc1nc2ccccc2n1-c1ccc(Oc2ccc(C(F)(F)F)cc2)cc1)C(N)=O] | 2-(((1-(4-(4-(trifluoromethyl)phenoxy)phenyl)-1H-benzo[d]imidazol-2-yl)methyl)amino)pentanediamide |
| 37 | 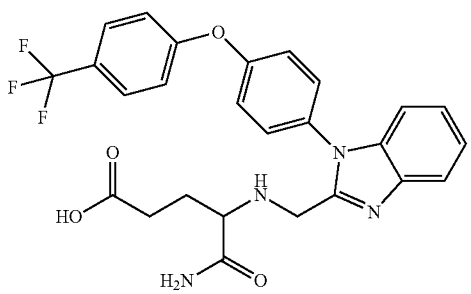 [SMILES: NC(=O)C(CCC(=O)O)NCc1nc2ccccc2n1-c1ccc(Oc2ccc(C(F)(F)F)cc2)cc1] | 5-amino-5-oxo-4-(((1-(4-(4-(trifluoromethyl)phenoxy)phenyl)-1H-benzo[d]imidazol-2-yl)methyl)amino)pentanoic acid |
| 38 | 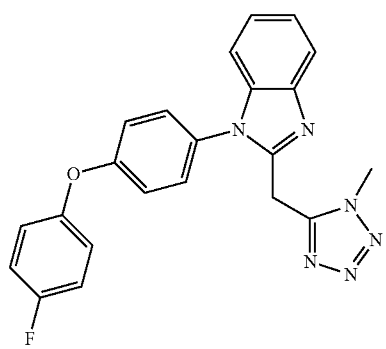 [SMILES: Cn1nnnc1Cc1nc2ccccc2n1-c1ccc(Oc2ccc(F)cc2)cc1] | 1-(4-(4-fluorophenoxy)phenyl)-2-((1-methyl-1H-tetrazol-5-yl)methyl)-1H-benzo[d]imidazole |
| 39 | 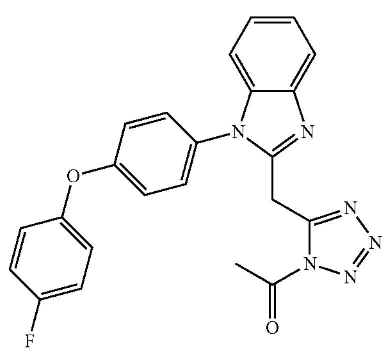 [SMILES: CC(=O)n1nnnc1Cc1nc2ccccc2n1-c1ccc(Oc2ccc(F)cc2)cc1] | 1-(5-((1-(4-(4-fluorophenoxy)phenyl)-1H-benzo[d]imidazol-2-yl)methyl)-1H-tetrazol-1-yl)ethan-1-one |

TABLE 2-continued

| Compd No. | Structure | Chemical Name |
|---|---|---|
| 40 | 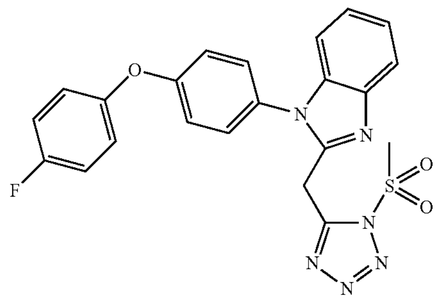 [SMILES: CS(=O)(=O)n1nnnc1Cc1nc2ccccc2n1-c1ccc(Oc2ccc(F)cc2)cc1] | 1-(4-(4-fluorophenoxy)phenyl)-2-((1-(methylsulfonyl)-1H-tetrazol-5-yl)methyl)-1H-benzo[d]imidazole |
| 41 | 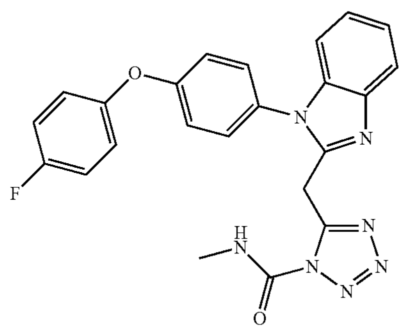 [SMILES: CNC(=O)n1nnnc1Cc1nc2ccccc2n1-c1ccc(Oc2ccc(F)cc2)cc1] | 5-((1-(4-(4-fluorophenoxy)phenyl)-1H-benzo[d]imidazol-2-yl)methyl)-N-methyl-1H-tetrazole-1-carboxamide |
| 42 | 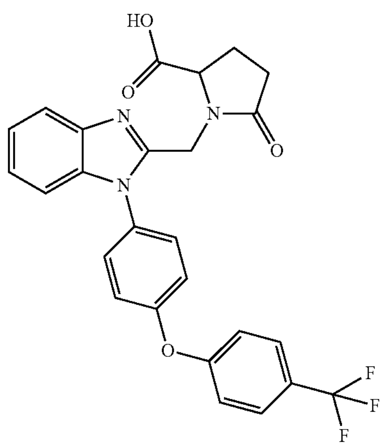 [SMILES: O=C(O)C1CCC(=O)N1Cc1nc2ccccc2n1-c1ccc(Oc2ccc(C(F)(F)F)cc2)cc1] | 5-oxo-1-((1-(4-(4-(trifluoromethyl)-phenoxy)phenyl)-1H-benzo[d]imidazol-2-yl)methyl)pyrrolidine-2-carboxylic acid |
| 43 | 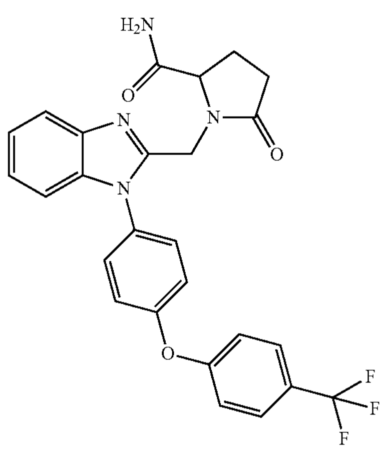 [SMILES: NC(=O)C1CCC(=O)N1Cc1nc2ccccc2n1-c1ccc(Oc2ccc(C(F)(F)F)cc2)cc1] | 5-oxo-1-((1-(4-(4-(trifluoromethyl)-phenoxy)phenyl)-1H-benzo[d]imidazol-2-yl)methyl)pyrrolidine-2-carboxamide |

In a certain embodiment, the Compounds of the Invention include the following compounds:
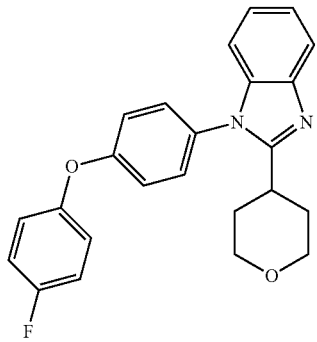
9
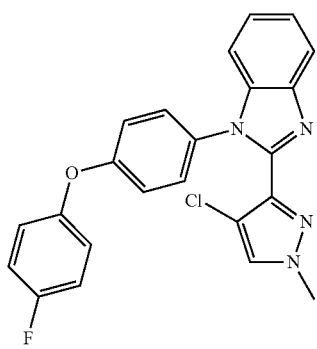
10
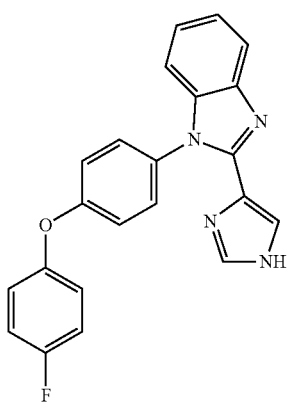
11
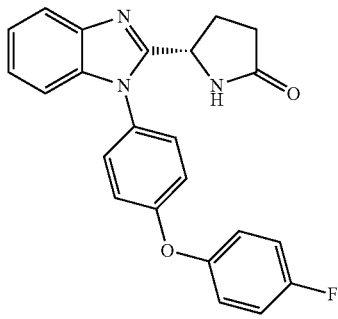
14
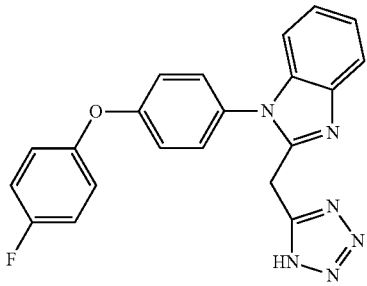
15
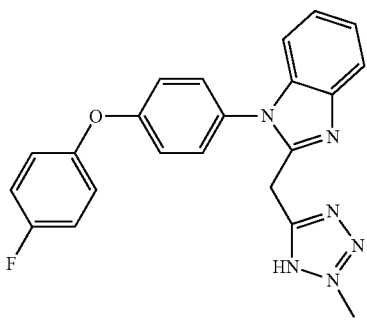
16
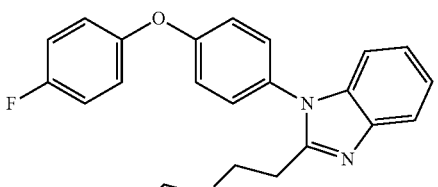
17
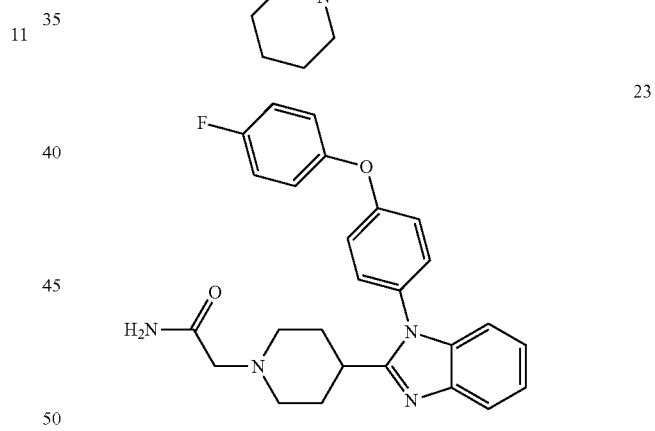
23
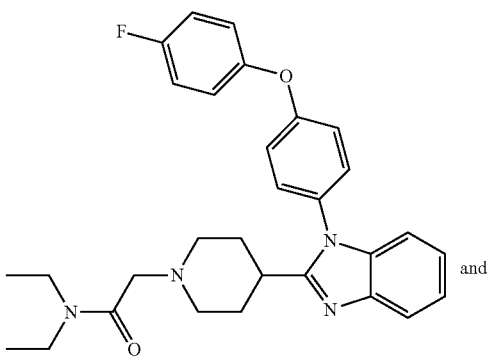
24
and

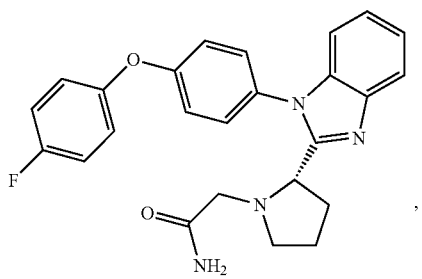
and the pharmaceutically acceptable salts, solvates, hydrates, and diastereomers thereof.
In another embodiment, the Compounds of the Invention include the following compounds:
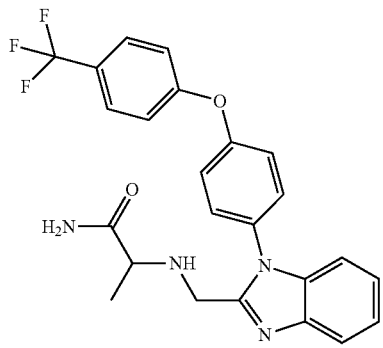
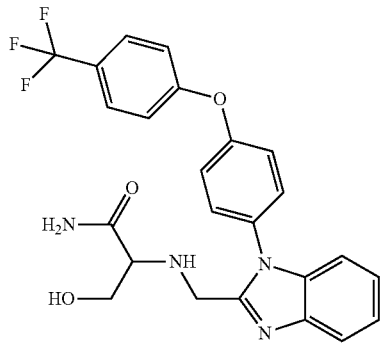
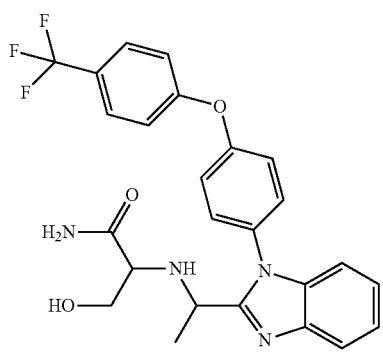
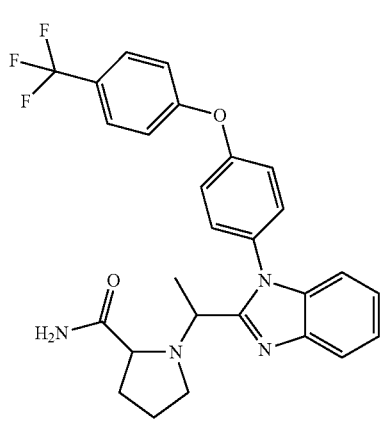

-continued

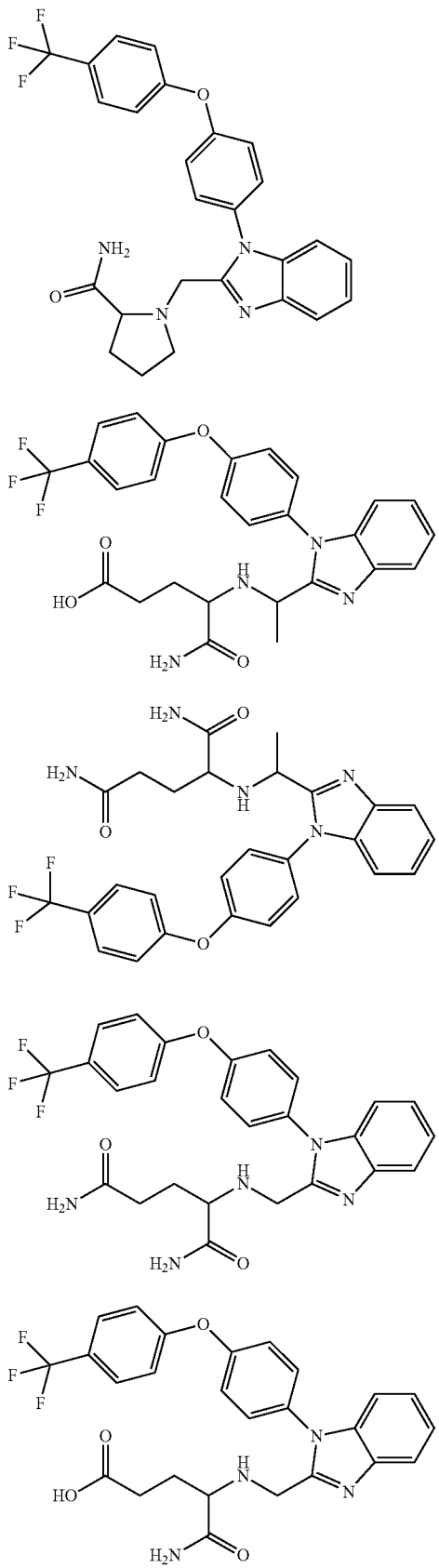

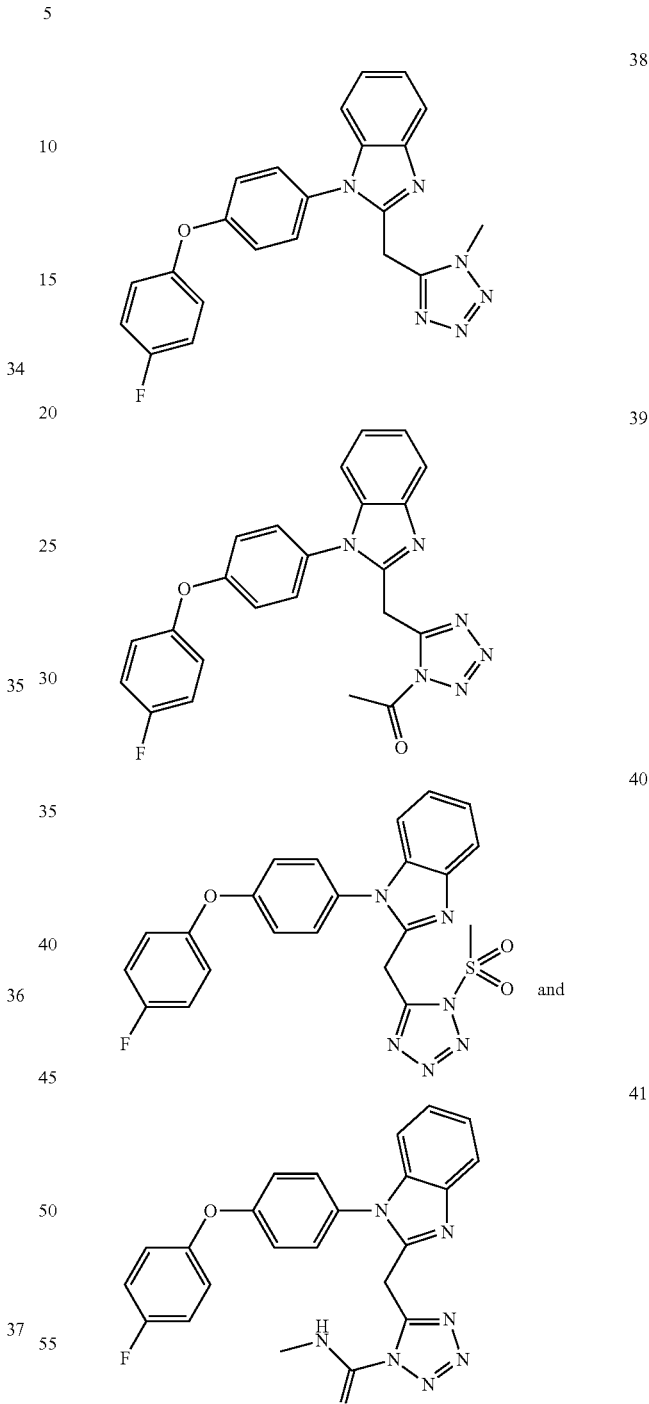

and the pharmaceutically acceptable salts, solvates, hydrates, and diastereomers thereof.

In yet another embodiment, the invention provides the following compounds:

and the pharmaceutically acceptable salts, solvates, hydrates, and diastereomers thereof.

Some of the compounds disclosed herein may contain one or more asymmetric centers and may thus give rise to enantiomers, diastereomers, and other stereoisomeric forms. The invention is meant to encompass the use of all such possible forms, as well as their racemic and resolved forms and mixtures thereof. The individual enantiomers can be separated according to methods well known in the art in view of the present disclosure. When the compounds described herein contain olefinic double bonds or other centers of geometric asymmetry, and unless specified otherwise, it is intended that they include both E and Z geometric isomers. All tautomers are intended to be encompassed by the present invention as well.

The invention also encompasses any of the disclosed compounds being isotopically-labelled (i.e., radiolabeled) by having one or more atoms replaced by an atom having a different atomic mass or mass number. Examples of isotopes that can be incorporated into the disclosed compounds include isotopes of hydrogen, carbon, nitrogen, oxygen, phosphorous, fluorine and chlorine, such as $^{2}H$, $^{3}H$, $^{11}C$, $^{13}C$, $^{14}C$, $^{15}N$, $^{18}O$, $^{17}O$, $^{31}P$, $^{32}P$, $^{35}S$, $^{18}F$, and $^{36}Cl$, respectively, and preferably $^{3}H$, $^{11}C$, and $^{14}C$. Isotopically-labeled compounds of the present invention can be prepared by methods known in the art.

The invention is also directed to $^{3}H$, $^{11}C$, or $^{14}C$ radiolabeled compounds of any of the above formulae, as well as their pharmaceutically acceptable salts, solvates, hydrates, diastereomers, and prodrugs thereof, and the use of any such compounds as radioligands for their ability to bind to the sodium channel. For example, one use of the labeled Compounds of the Invention is the characterization of specific receptor binding. Another use of a labeled Compound of the Invention is an alternative to animal testing for the evaluation of structure-activity relationships. For example, the receptor assay can be performed at a fixed concentration of a labeled Compound of the Invention and at increasing concentrations of a test compound in a competition assay. For example, a tritiated compound of any of Formulae I to V can be prepared by introducing tritium into the particular compound, for example, by catalytic dehalogenation with tritium. This method may include reacting a suitably halogen-substituted precursor of the compound with tritium gas in the presence of a suitable catalyst, for example, Pd/C, in the presence or absence of a base. Other suitable methods for preparing tritiated compounds can be found in Filer, *Isotopes in the Physical and Biomedical Sciences, Vol. 1, Labeled Compounds (Part A)*, Chapter 6 (1987). $^{14}C$-labeled compounds can be prepared by employing starting materials having a $^{14}C$ carbon.

The invention also encompasses the use of salts of the disclosed compounds, including all non-toxic pharmaceutically acceptable salts thereof of the disclosed compounds. Examples of pharmaceutically acceptable addition salts include inorganic and organic acid addition salts and basic salts.

The pharmaceutically acceptable salts include, but are not limited to, metal salts such as sodium salt, potassium salt, cesium salt and the like; alkaline earth metals such as calcium salt, magnesium salt and the like; organic amine salts such as triethylamine salt, pyridine salt, picoline salt, ethanolamine salt, triethanolamine salt, dicyclohexylamine salt, N,N'-dibenzylethylenediamine salt and the like; inorganic acid salts such as hydrochloride, hydrobromide, phosphate, sulphate and the like; organic acid salts such as citrate, lactate, tartrate, maleate, fumarate, mandelate, acetate, dichloroacetate, trifluoroacetate, oxalate, formate and the like; sulfonates such as methanesulfonate, benzenesulfonate, p-toluenesulfonate and the like; and amino acid salts such as arginate, aspartginate, glutamate and the like.

Acid addition salts can be formed by mixing a solution of the particular Compound of the Invention with a solution of a pharmaceutically acceptable non-toxic acid such as hydrochloric acid, fumaric acid, maleic acid, succinic acid, acetic acid, citric acid, tartaric acid, carbonic acid, phosphoric acid, oxalic acid, dichloroacetic acid, or the like. Basic salts can be formed by mixing a solution of the Compound of the Invention with a solution of a pharmaceutically acceptable non-toxic base such as sodium hydroxide, potassium hydroxide, choline hydroxide, sodium carbonate and the like.

The invention also encompasses solvates of any of the disclosed compounds. Solvates typically do not significantly alter the physiological activity or toxicity of the compounds, and as such may function as pharmacological equivalents. The term "solvate" as used herein is a combination, physical association and/or solvation of a Compound of the Invention with a solvent molecule such as, e.g. a disolvate, monosolvate or hemisolvate, where the ratio of solvent molecule to a Compound of the Invention is 2:1, 1:1 or 1:2, respectively. This physical association involves varying degrees of ionic and covalent bonding, including hydrogen bonding. In certain instances, the solvate can be isolated, such as when one or more solvent molecules are incorporated into the crystal lattice of a crystalline solid. Thus, "solvate" encompasses both solution-phase and isolatable solvates. Compounds of any of Formulae I to V can be present as solvated forms with a pharmaceutically acceptable solvent, such as water, methanol, ethanol, and the like, and it is intended that the invention includes both solvated and unsolvated forms of compounds of any of Formulae I to V.

Further, the invention encompasses hydrates of any of the disclosed compounds. It is appreciated that a hydrate may be considered as a specific type of solvate. In other words, it may be appreciated in the art that a "hydrate" is a particular subgroup of solvates where the solvent molecule is water.

Solvates typically can function as pharmacological equivalents. Preparation of solvates is known in the art. See, for example, M. Caira et a.l, *J. Pharmaceut. Sci.*, 93(3):601-611 (2004), which describes the preparation of solvates of fluconazole with ethyl acetate and with water. Similar preparation of solvates, hemisolvates, hydrates, and the like are described by E. C. van Tonder et al., *AAPS Pharm. Sci. Tech.*, 5(1): Article 12 (2004), and A. L. Bingham et al., *Chem. Commun.*: 603-604 (2001). A typical, non-limiting, process of preparing a solvate would involve dissolving a compound of any of the formulae discussed above in a desired solvent (organic, water, or a mixture thereof) at temperatures above 20° C. to about 25° C., then cooling the solution at a rate sufficient to form crystals, and isolating the crystals by known methods, e.g., filtration. Analytical techniques such as infrared spectroscopy can be used to confirm the presence of the solvent in a crystal of the solvate.

The invention is also meant to encompass prodrugs of any of the disclosed compounds. As used herein, prodrugs are considered to be compounds with moieties that can be metabolized in vivo. In general, such prodrugs will be functional derivatives of compounds of any of the formulae delineated herein, which will be readily convertible in vivo, e.g., by being metabolized, into the required compound of any of the formulae. Conventional procedures for the selection and preparation of suitable prodrug derivatives are described in, for example, *Design of Prodrugs*, H. Bundgaard ed., Elsevier (1985); "Drug and Enzyme Targeting, Part A," K. Widder et al. eds., Vol. 112 in *Methods in Enzymology*, Academic Press (1985); Bundgaard, "Design and Application of Prodrugs," Chapter 5 (pp. 113-191) in *A Textbook of Drug Design and Development*, P. Krogsgaard-Larsen and H. Bundgaard eds., Harwood Academic Publishers (1991); Bundgaard et al., *Adv. Drug Delivery Revs.*

8:1-38 (1992); Bundgaard et al., *J. Pharmaceut. Sci.* 77:285 (1988); and Kakeya et al., *Chem. Pharm. Bull.* 32:692 (1984).

Examples of prodrugs and their use are well known in the art (e.g., Berge et al. (1997) "Pharmaceutical Salts", *J. Pharm. Sci.* 66:1-19). Non-limiting examples of prodrugs include esters or amides of Compounds of the Invention having carboxy, hydroxy or amino groups as a substituent, and these can be prepared by reacting such parent compounds with anhydrides such as succinic anhydride.

Methods and Use of the Compounds of the Invention

In certain embodiments, the Compounds of the Invention act as blockers of one or more sodium ($Na^+$) channels. Consequently, a number of diseases and conditions mediated by sodium ion influx can be treated by employing the Compounds of the Invention. The invention thus provides generally a method for treating a disorder responsive to blockade of one or more sodium channels in an animal (e.g., a human) suffering from, or at risk of suffering from, said disorder. In one embodiment, the method of the invention comprises a step of administering to the animal an effective amount of a Compound of the Invention.

The invention further provides a method of modulating one or more sodium channels in an animal identified as in need thereof, said method comprising administering to the animal a modulating-effective amount of at least one Compound of the Invention.

In one embodiment, the invention provides a method of treating stroke, neuronal damage resulting from head trauma, epilepsy, neuronal loss following global and focal ischemia, pain (e.g., acute pain, chronic pain, which includes but is not limited to neuropathic pain, postoperative pain, and inflammatory pain, or surgical pain), a neurodegenerative disorder (e.g., Alzheimer's disease, amyotrophic lateral sclerosis (ALS), or Parkinson's disease), migraine, manic depression, tinnitus, myotonia, a movement disorder, or cardiac arrhythmia, or providing local anesthesia. In one embodiment, the invention provides a method of treating pain.

In another embodiment, the type of pain is chronic pain. In another embodiment, the type of pain is neuropathic pain. In another embodiment, the type of pain is postoperative pain. In another embodiment, the type of pain is inflammatory pain. In another embodiment, the type of pain is surgical pain. In another embodiment, the type of pain is acute pain.

In another embodiment, the treatment of pain (e.g., chronic pain, such as neuropathic pain, postoperative pain, or inflammatory pain, acute pain or surgical pain) is preemptive. In another embodiment, the treatment of pain is palliative. In each instance, such method of treatment requires administering to an animal in need of such treatment an amount of a Compound of the Invention that is therapeutically effective in achieving said treatment. In one embodiment, the amount of such compound is the amount that is effective to block sodium channels in vivo.

Chronic pain includes, but is not limited to, inflammatory pain, postoperative pain, cancer pain, osteoarthritis pain associated with metastatic cancer, trigeminal neuralgia, acute herpetic and postherpetic neuralgia, diabetic neuropathy, causalgia, brachial plexus avulsion, occipital neuralgia, reflex sympathetic dystrophy, fibromyalgia, gout, phantom limb pain, burn pain, and other forms of neuralgia, neuropathic, and idiopathic pain syndromes.

Chronic somatic pain generally results from inflammatory responses to tissue injury such as nerve entrapment, surgical procedures, cancer or arthritis (Brower, *Nature Biotechnology* 2000; 18: 387-391).

The inflammatory process is a complex series of biochemical and cellular events activated in response to tissue injury or the presence of foreign substances (Levine, *Inflammatory Pain, In: Textbook of Pain*, Wall and Melzack eds., $3^{rd}$ e.d., 1994). Inflammation often occurs at the site of injured tissue, or foreign material, and contributes to the process of tissue repair and healing. The cardinal signs of inflammation include erythema (redness), heat, edema (swelling), pain and loss of function (ibid.). The majority of patients with inflammatory pain do not experience pain continually, but rather experience enhanced pain when the inflamed site is moved or touched. Inflammatory pain includes, but is not limited to, that associated with osteoarthritis and rheumatoid arthritis.

Chronic neuropathic pain is a heterogenous disease state with an unclear etiology. In chronic neuropathic pain, the pain can be mediated by multiple mechanisms. This type of pain generally arises from injury to the peripheral or central nervous tissue. The syndromes include pain associated with spinal cord injury, multiple sclerosis, post-herpetic neuralgia, trigeminal neuralgia, phantom pain, causalgia, and reflex sympathetic dystrophy and lower back pain. Chronic pain is different from acute pain in that patients suffer the abnormal pain sensations that can be described as spontaneous pain, continuous superficial burning and/or deep aching pain. The pain can be evoked by heat-, cold-, and mechano-hyperalgesia or by heat-, cold-, or mechano-allodynia.

Neuropathic pain can be caused by injury or infection of peripheral sensory nerves. It includes, but is not limited to, pain from peripheral nerve trauma, herpes virus infection, diabetes mellitus, causalgia, plexus avulsion, neuroma, limb amputation, and vasculitis. Neuropathic pain is also caused by nerve damage from chronic alcoholism, human immunodeficiency virus infection, hypothyroidism, uremia, or vitamin deficiencies. Stroke (spinal or brain) and spinal cord injury can also induce neuropathic pain. Cancer-related neuropathic pain results from tumor growth compression of adjacent nerves, brain, or spinal cord. In addition, cancer treatments, including chemotherapy and radiation therapy, can also cause nerve injury. Neuropathic pain includes but is not limited to pain caused by nerve injury such as, for example, the pain from which diabetics suffer.

The invention is also directed to the use of a compound represented by any one of the above formulae, or a pharmaceutically acceptable salt, hydrate, solvate, or diastereomer thereof, in the manufacture of a medicament for treating a disorder responsive to the blockade of one or more sodium channels (e.g., any of the disorders listed above) in an animal suffering from said disorder.

Further, the invention relates to the use of a compound represented by any one of the above formulae, or a pharmaceutically acceptable salt, hydrate, solvate, or diastereomer thereof, in the manufacture of a medicament, in particular a medicament for modulating one or more sodium channels, in an animal in need thereof.

General Synthetic Schemes

The Compounds of the Invention can be readily prepared using methods known to those skilled in the art in view of this disclosure.

For example, the compounds of Formula I can be made using conventional organic synthesis in view of this disclosure, or by the illustrative methods shown in the Schemes below.

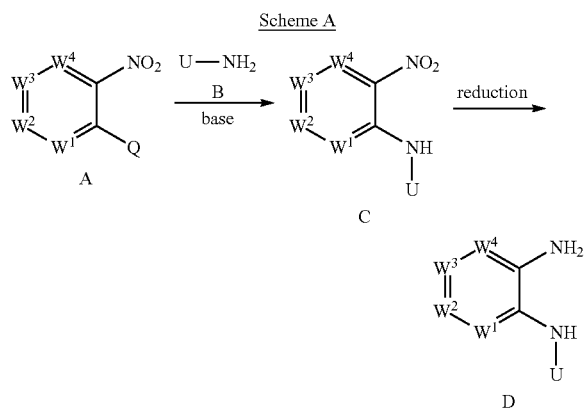

Compound A, where Q is a suitable leaving group, such as, halogen, tosylate, mesylate or triflate, is converted to Compound C by reaction with a suitable amine (such as, Compound B) in the presence of a suitable base (such as, DIPEA) in a suitable solvent, such as, DMSO. The nitro group in Compound C is converted to an amine, such as, the amine group in Compound D, by suitable reducing conditions (such as, hydrogenation) in a suitable solvent (such as, MeOH) in the presence of a suitable catalyst (such as, Pd/C).

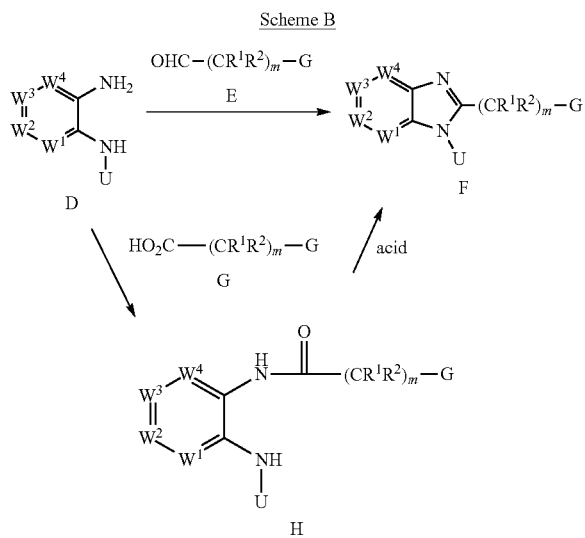

Compound D is converted to Compound F by reaction with a suitable aldehyde (such as, Compound E) in a suitable solvent (such as, aq. EtOH) in the presence of a suitable additive (such as, NaHSO$_3$). An alternate approach is by the reaction of Compound D with a suitable acid (such as, Compound G) in the presence of a suitable coupling reagent (such as, EDCI) in a suitable solvent (such as, DCM) to give Compound H. Compound H is then converted to Compound F by heating in a suitable solvent (such as, toluene) in the presence of a suitable acid catalyst (such as, HOAc).

Subsequent side chain modifications can be accomplished via appropriate functional group manipulations known to one skilled in the art.

Testing of Compounds

Representative Compounds of the Invention were assessed by sodium mobilization and/or electrophysiological assays for sodium channel blocker activity. One aspect of the invention is based on the use of the compounds herein described as sodium channel blockers. Based upon this property, the Compounds of the Invention are considered useful in treating a condition or disorder responsive to the blockade of one or more sodium ion channels, e.g., stroke, neuronal damage resulting from head trauma, epilepsy, seizures, general epilepsy with febrile seizures, severe myoclonic epilepsy in infancy, neuronal loss following global and focal ischemia, migraine, familial primary erythromelalgia, paroxysmal extreme pain disorder, cerebellar atrophy, ataxia, dystonia, tremor, mental retardation, autism, a neurodegenerative disorder (e.g., Alzheimer's disease, amyotrophic lateral sclerosis (ALS), or Parkinson's disease), manic depression, tinnitus, myotonia, a movement disorder, cardiac arrhythmia, or providing local anesthesia.

In one embodiment, the Compounds of the Invention are effective in treating pain, e.g., acute pain, chronic pain, which includes but is not limited to, neuropathic pain, postoperative pain, and inflammatory pain, or surgical pain.

In certain embodiments, the invention provides compounds of Formulae I to V and pharmaceutically acceptable salts, solvates, hydrates, and diastereomers thereof that are useful as blockers of one or more sodium channels. According to the invention, those compounds having useful sodium channel blocking properties exhibit an IC$_{50}$ for Na$_v$1.1, Na$_v$1.2, Na$_v$1.3, Na$_v$1.4, Na$_v$1.5, Na$_v$1.6, Na$_v$1.7, Na$_v$1.8, and/or Na$_v$1.9 of about 100 µM or less, e.g., about 50 µM or less, about 10 µM or less, about 5 µM or less, or about 1 µM or less, in sodium mobilization and/or electrophysiological assays. In certain embodiments, Compounds of the Invention exhibit an IC$_{50}$ for Na$_v$1.7 of 100 µM or less, about 50 µM or less, about 10 µM or less, about 5 µM or less, about 1 µM or less, about 0.5 µM or less, or about 0.1 µM or less. Compounds of the Invention can be tested for their Na$^+$ channel blocking activity using methods known in the art and by the following fluorescence imaging and electrophysiological in vitro assays and/or in vivo assays.

In one embodiment, the Compounds of the Invention demonstrate substantially no penetration across the CNS blood-brain barrier in a mammal. Such compounds are referred to as "peripherally restricted" as a means to designate their PNS versus CNS tissue selectivity.

In one embodiment, the PNS:CNS concentration ratio of a peripherally restricted Compound of the Invention is about 5:1, about 10:1, about 20:1, about 30:1; about 50:1; about 100:1, about 250:1, about 500:1, about 1000:1, about 5,000:1, about 10,000:1, or more. Compounds of the Invention can be tested for their ability to penetrate the central nervous system using in vitro and in vivo methods known in the art.

In Vitro Assay Protocols

FLIPR® Assays

Recombinant Na$_v$1.7 Cell Line: In vitro assays were performed in a recombinant cell line expressing cDNA encoding the alpha subunit (Na$_v$1.7, SCN9a, PN1, NE) of human Na$_v$1.7 (Accession No. NM_002977). The cell line was provided by investigators at Yale University (Cummins et al, *J. Neurosci.* 18(23): 9607-9619 (1998)). For dominant selection of the Na$_v$1.7-expressing clones, the expression plasmid co-expressed the neomycin resistance gene. The cell line was constructed in the human embryonic kidney cell line, HEK293, under the influence of the CMV major late promoter, and stable clones were selected using limiting dilution cloning and antibiotic selection using the neomycin analogue, G418. Recombinant beta and gamma subunits were not introduced into this cell line. Additional cell lines expressing recombinant $Na_v1.7$ cloned from other species can also be used, alone or in combination with various beta subunits, gamma subunits or chaperones.

Non-Recombinant Cell Lines Expressing Native $Na_v1.7$: Alternatively, in vitro assays can be performed in a cell line expressing native, non-recombinant $Na_v1.7$, such as the ND7 mouse neuroblastoma X rat dorsal root ganglion (DRG) hybrid cell line ND7/23, available from the European Cell Culture Collection (Cat. No. 92090903, Salisbury, Wiltshire, United Kingdom). The assays can also be performed in other cell lines expressing native, non-recombinant $Na_v1.7$, from various species, or in cultures of fresh or preserved sensory neurons, such as dorsal root ganglion (DRG) cells, isolated from various species. Primary screens or counter-screens of other voltage-gated sodium channels can also be performed, and the cell lines can be constructed using methods known in the art, purchased from collaborators or commercial establishments, and they can express either recombinant or native channels. The primary counter-screen is for one of the central neuronal sodium channels, $Na_v1.2$ (rBIIa), expressed in HEK293 host cells (Ilyin et al., *Br. J. Pharmacol.* 144:801-812 (2005)). Pharmacological profiling for these counter-screens is carried out under conditions similar to the primary or alternative $Na_v1.7$ assays described below.

Cell Maintenance: Unless otherwise noted, cell culture reagents were purchased from Mediatech of Herndon, Va. The recombinant $Na_v1.7$/HEK293 cells were routinely cultured in growth medium consisting of Dulbecco's minimum essential medium containing 10% fetal bovine serum (FBS, Hyclone, Thermo Fisher Scientific, Logan, Utah), 100 Um/L penicillin, 100 µg/mL streptomycin, 2-4 mM L-glutamine, and 500 mg/mL G418. For natural, non-recombinant cell lines, the selective antibiotic was omitted, and additional media formulations can be applied as needed.

Assay Buffer: The assay buffer was formulated by removing 120 mL from a 1 L bottle of fresh, sterile $dH_2O$ (Mediatech, Herndon, Va.) and adding 100 mL of 10×HBSS that does not contain $Ca^{++}$ or $Mg^{++}$ (Gibco, Invitrogen, Grand Island, N.Y.) followed by 20 mL of 1.0 M Hepes, pH 7.3 (Fisher Scientific, BP299-100). The final buffer consisted of 20 mM Hepes, pH 7.3, 1.261 mM $CaCl_2$, 0.493 mM $MgCl_2$, 0.407 mM $Mg(SO)_4$, 5.33 mM KCl, 0.441 mM $KH_2PO_4$, 137 mM NaCl, 0.336 mM $Na_2HPO_4$ and 0.556 mM D-glucose (Hanks et al., *Proc. Soc. Exp. Biol. Med.* 71:196 (1949)), and the simple formulation was typically the basic buffer throughout the assay (i.e., all wash and addition steps).

CoroNa™ Green AM $Na^+$ Dye for Primary Fluorescence Assay: The fluorescence indicator used in the primary fluorescence assay was the cell permeant version of CoroNa™ Green (Invitrogen, Molecular Probes, Eugene, Oreg.), a dye that emits light in the fluorescence range (Harootunian et al., *J. Biol. Chem.* 264(32):19458-19467 (1989)). The intensity of this emission, but not the wavelength range, is increased when the dye is exposed to $Na^+$ ions, which it can bind with partial selectivity. Cells expressing $Na_v1.7$ or other sodium channels were loaded with the CoroNa™ Green dye immediately in advance of the fluorescence assay, and then, after agonist stimulation, the mobilization of $Na^+$ ions was detected as the $Na^+$ ions flowed from the extracellular fluid into the cytoplasm through the activated sodium channel pores. The dye was stored in the dark as a lyophilized powder, and then an aliquot was dissolved immediately before the cell loading procedure, according to the instructions of the manufacturer to a stock concentration of 10 mM in DMSO. It was then diluted in the assay buffer to a 4× concentrated working solution, so that the final concentration of dye in the cell loading buffer was 5 µM.

Membrane Potential Dye for Alternative Fluorescence Assays: A fluorescence indicator that can be used in alternative fluorescence assays is the blue version membrane potential dye (MDS, Molecular Devices, Sunnyvale, Calif.), a dye that detects changes in molecules following a change in membrane potential. An increase in fluorescence is expected if agonist stimulation provokes a change in membrane potential. Cells expressing $Na_v1.7$ or other sodium channels are incubated with the membrane potential dye 30-60 minutes before the fluorescence assay. In the case of the KCl pre-stimulation version of the assay, the dye and all other components are washed out immediately before the assay, and the dye is then replaced. In the version lacking KCl pre-stimulation, the dye remains on the cells and is not washed out or replaced. The dye is stored in the dark as a lyophilized powder, and then an aliquot dissolved in assay buffer to form a 20×-concentrated stock solution that can be used for several weeks.

Agonists: In the fluorescence assays, two agonists were used in combination, namely 1) veratridine; and 2) the venom from the yellow scorpion, *Leiurus quinquestriatus hebraeus*. Veratridine is an alkaloid small molecule that facilitates the capture of channel openings by inhibiting inactivation, and the scorpion venom is a natural preparation that includes peptide toxins selective for different subsets of voltage-gated sodium channels. These scorpion toxins inhibit the fast inactivation of their cognate target channels. Stock solutions of the agonists were prepared to 40 mM in DMSO (veratridine) and 1 mg/mL in $dH_2O$ (scorpion venom), and then diluted to make a 4× or 2× stock (depending on the particular assay) in assay buffer, the final concentration being 100 µM (veratridine) and 10 µg/mL (scorpion venom). Both of the agonists were purchased from Sigma Aldrich, St. Louis, Mo.

Test Compounds: Test compounds were dissolved in DMSO to yield 10 mM stock solutions. The stock solutions were further diluted using DMSO in 1:3 serial dilution steps with 10 points (10,000 µM, 3,333 µM, 1,111 µM, 370 µM, 123 µM, 41 µM, 14 µM, 4.6 µM, 1.5 µM and 0.5 µM). The stock solutions were further diluted in assay buffer (1:125) as 4× stock serial dilutions with a DMSO concentration of 0.8% (final [DMSO], in the assay, from the compounds component=0.2%), so that the compounds' final concentrations in the assay were 20 µM, 6.7 µM, 2.2 µM, 0.74 µM, 0.25 µM and 0.08 µM, 0.03 µM, 0.01 µM, 0.003 µM and 0.001 µM. If a particular test article appeared to be especially potent, then the concentration curve was adjusted, e.g., to 10-fold lower concentrations, in order to perform the dose-response in a more relevant concentration range. Compound dilutions were added during the dye-loading and pre-stimulation step, and then again during the fluorescence assay, early in the kinetic read. Compound dilutions were added in duplicate rows across the middle 80 wells of the 96-well plate, whereas the fully stimulated and the fully inhibited controls (positive and negative) were located in the top 4 side wells and the bottom 4 side wells, respectively, on the left and right sides of the assay plate.

Data Analysis: The data were analyzed according to methods known to those skilled in the art or using the GraphPad® Prism 4.0 Program (available from GraphPad Software, San Diego, Calif.) to determine the $IC_{50}$ value for the test article. At least one standard reference compound was evaluated during each experiment.

FLIPR® or FLIPR$^{TETRA}$® sodium dye assay with KCl and test article pre-incubation: Cells were prepared by plating the recombinant HEK293 cells or other host cells expressing either recombinant or non-recombinant, native, $Na_v1.7$ alpha subunit, alone or in combination with various beta and gamma subunits at a density of ~40,000 cells/well into a 96-well black, clear-bottom, PDL-coated plate. The assay can be adapted to 384-well or 1,536-well format, if desired, using proportionately fewer cells and less media. The plate was then incubated in growth media, with or without selective antibiotic, overnight at 37° C. at 5% $CO_2$, 95% humidity, in preparation for the assay. For counter-screens of other voltage-gated sodium channels, the procedure was very similar, though optimal densities of cells, media and subsequent assay components can be fine-tuned for the particular cell line or isoform.

The next day, at the start of the assay, the media was flicked from the cells and the wells were washed once with 50 μl/well assay buffer (1× Hank's balanced salt solution without sodium bicarbonate or phenol red, 20 mM Hepes, pH 7.3) and then pre-incubated with the test articles, CoroNa™ Green AM sodium dye (for cell loading) and KCl for re-polarization and synchronization of the channels in the entire population of cells. For this dye-loading and pre-stimulation step, the components were added as follows, immediately after the wash step: 1) first, the compound dilutions and controls were added as 4× concentrates in assay buffer at 50 μL/well; 2) CoroNa™ Green AM dye was diluted from the stock solution to 20 μM in assay buffer (4× concentrate) and added to the plate at 50 μL/well; and 3) finally, a solution of 180 mM KCl (2×) was prepared by diluting a 2M stock solution into assay buffer and the solution was added to the cells at 100 μl/well. The cells were incubated at 25° C. in the dark for 30 mM before their fluorescence was measured.

The plates containing dye-loaded cells were then flicked to remove the pre-incubation components and washed once with 100 μL/well assay buffer. A 100 μL/well aliquot of assay buffer was added back to the plate, and the real-time assay was commenced. The fluorescence of cells was measured using a fluorescence plate reader (FLIPR$^{TETRA}$® or FLIPR384®, MDS, Molecular Devices, Sunnyvale, Calif.) Samples were excited by either a laser or a PMT light source (Excitation wavelength=470-495 nM) and the emissions were filtered (Emission wavelength=515-575 nM). The additions of compound and the channel activators in this cell-based, medium-to-high throughput assay were performed on the fluorescence plate reader and the results (expressed as relative fluorescence units) were captured by means of camera shots every 1-3 sec., then displayed in real-time and stored. Generally, there was a 15 sec. base line, with camera shots taken every 1.5 sec., then the test compounds were added, then another 120 sec. baseline was conducted, with camera shots taken every 3 sec.; and finally, the agonist solution (containing veratridine and scorpion venom) was added. The amplitude of fluorescence increase, resulting from the binding of $Na^+$ ions to the CoroNa™ Green dye, was captured for ~180 sec. thereafter. Results were expressed in relative fluorescence units (RFU) and can be determined by using the maximum signal during the latter part of the stimulation; or the maximum minus the minimum during the whole agonist stimulation period; or by taking the area under the curve for the whole stimulation period.

The assay can be performed as a screening assay as well with the test articles present in standard amounts (e.g., 10 μM) in only one or two wells of a multi-well plate during the primary screen. Hits in this screen will typically be profiled more exhaustively (multiple times), subjected to dose-response or competition assays and tested in counter screens against other voltage-gate sodium channels or other biologically relevant target molecules.

FLIPR® or FLIPR$^{TETRA}$® membrane potential assay with KCl and test article pre-incubation: Cells are prepared by plating the recombinant HEK293 cells or other host cells expressing either recombinant or non-recombinant, native, $Na_v1.7$ alpha subunit, alone or in combination with various beta and gamma subunits at a density of ~40,000 cells/well into a 96-well black, clear-bottom, PDL-coated plate. The assay can be adapted to 384-well or 1,536-well format, if desired, using proportionately fewer cells and less media. The plate is then incubated in growth media, with or without selective antibiotic, overnight at 37° C. at 5% $CO_2$, 95% humidity, in preparation for the assay (see, e.g., Benjamin et. al., *J. Biomol. Screen* 10(4):365-373 (2005)). For screens and counter-screens of other voltage-gated sodium channels, the assay protocol is similar, though optimal densities of cells, media and subsequent assay components can be fine-tuned for the particular cell line or sodium channel isoform being tested.

The next day, at the start of the assay, the media is flicked from the cells and the wells are washed once with 50 μL/well assay buffer (1× Hank's balanced salt solution without sodium bicarbonate or phenol red, 20 mM Hepes, pH 7.3) and then pre-incubated with the test articles, the membrane potential dye (for cell loading), and the KCl for re-polarization and synchronization of the channels in the entire population of cells. For this dye-loading and pre-stimulation step, the components are added as follows, immediately after the wash step: 1) first, the compound dilutions and controls are added as 4× concentrates in assay buffer at 50 μL/well; 2) membrane potential dye is diluted from the stock solution in assay buffer (4× concentrate) and added to the plate at 50 μL/well; and 3) finally, a solution of 180 mM KCl (2×) is prepared by diluting a 2M stock solution into assay buffer and the solution added to the cells at 100 μL/well. The cells are incubated at 37° C. in the dark for 30-60 mM before their fluorescence is measured.

The plates containing dye-loaded cells are then flicked to remove the pre-incubation components and washed once with 50 μL/well assay buffer. A 50 μL/well aliquot of membrane potential dye is added back to the plate, and the real-time assay is commenced. The fluorescence of cells is measured using a fluorescence plate reader (FLIPR$^{TETRA}$® or FLIPR384®, MDS, Molecular Devices, Sunnyvale, Calif.). Samples are excited by either a laser or a PMT light source (Excitation wavelength=510–545 nM) and the emissions are filtered (Emission wavelength=565–625 nM). The additions of the compounds (first) and then the channel activators (later) in this are performed on the fluorescence plate reader and the results, expressed as relative fluorescence units (RFU), are captured by means of camera shots every 1-3 sec., then displayed in real-time and stored. Generally, there is a 15 sec. base line, with camera shots taken every 1.5 sec., then the test compounds are added, then another 120 sec. baseline is conducted, with camera shots taken every 3 sec.; and finally, the agonist solution (containing veratridine and scorpion venom) is added. The amplitude of fluorescence increase, resulting from the detection of membrane potential change, is captured for ~120 sec. thereafter. Results are expressed in relative fluorescence units (RFU) and can be determined by using the maximum signal during the latter part of the stimulation; or the maximum minus the minimum during the whole stimulation period; or by taking the area under the curve for the whole stimulation period.

The assay can be performed as a screening assay as well with the test articles present in standard amounts (e.g., 10 µM) in only one or two wells of a multi-well plate during the primary screen. Hits in this screen are typically profiled more exhaustively (multiple times), subjected to dose-response or competition assays and tested in counter screens against other voltage-gate sodium channels or other biologically relevant target molecules.

FLIPR® or FLIPR$^{TETRA}$® sodium dye assay without kcl and test article pre-incubation: Cells are prepared by plating the recombinant HEK293 cells or other host cells expressing either recombinant or non-recombinant, native, $Na_v1.7$ alpha subunit, alone or in combination with various beta and gamma subunits at a density of ~40,000 cells/well into a 96-well black, clear-bottom, PDL-coated plate. The assay can be adapted to 384-well or 1,536-well format, if desired, using proportionately fewer cells and less media. The plate is then incubated in growth media, with or without selective antibiotic, overnight at 37° C. at 5% $CO_2$, 95% humidity, in preparation for the assay. For counter-screens of other voltage-gated sodium channels, the procedure is very similar, though optimal densities of cells, media and subsequent assay components can be fine-tuned for the particular cell line or isoform.

The next day, at the start of the assay, the media is flicked from the cells and the wells washed once with 50 µL/well assay buffer (1× Hank's balanced salt solution without sodium bicarbonate or phenol red, 20 mM Hepes, pH 7.3). Membrane potential dye is then added to each well of the 96-well plate (50 µL/well), from a freshly diluted sample of the stock (now at 4× concentration) in the assay buffer. The cells are incubated at 37° C. in the dark for 30-60 mM before their fluorescence is measured.

In this standard membrane potential assay, the 96-well plate containing dye-loaded cells is then loaded directly onto the plate reader without aspirating the dye solution and without any further washing of the cells. The fluorescence of cells is measured using a fluorescence plate reader (FLIPR$^{TETRA}$® or FLIPR384®, MDS, Molecular Devices, Sunnyvale, Calif.). Samples are excited by either a laser or a PMT light source (Excitation wavelength=510-545 nM) and the emissions are filtered (Emission wavelength=565-625 nM). The additions of the compounds (first, 50 µL/well from a 4× stock plate) and then the channel activators (later, 100 µL/well from a 2× stock solution) in this kinetic assay are performed on the fluorescence plate reader and the results, expressed as relative fluorescence units (RFU), are captured by means of camera shots every 1-3 sec., then displayed in real-time and stored. Generally, there is a 15 sec. base line, with camera shots taken every 1.5 sec., then the test compounds are added, then another 120 sec. baseline is conducted, with camera shots taken every 3 sec.; and finally, the agonist solution (containing veratridine and scorpion venom) is added. The amplitude of fluorescence increase, resulting from the detection of membrane potential change, is captured for ~120 sec. thereafter. Results are expressed in relative fluorescence units (RFU) and can be determined by using the maximum signal during the latter part of the stimulation; or the maximum minus the minimum during the whole stimulation period; or by taking the area under the curve for the whole stimulation period.

The assay can be performed as a screening assay as well, with the test articles present in standard amounts (e.g. 10 µM) in only one or two wells of a multi-well plate during the primary screen. Hits in this screen are typically profiled more exhaustively (multiple times), subjected to dose-response or competition assays and tested in counter screens against other voltage-gate sodium channels or other biologically relevant target molecules.

Electrophysiology Assay

Cells: The $hNa_v1.7$ expressing HEK-293 cells are plated on 35 mm culture dishes pre-coated with poly-D-lysine in standard DMEM culture media (Mediatech, Inc., Herndon, Va.) and incubated in a 5% $CO_2$ incubator at 37° C. Cultured cells are used approximately 12-48 hours after plating.

Electrophysiology: On the day of experimentation, the 35 mm dish is placed on the stage of an inverted microscope equipped with a perfusion system that continuously perfuses the culture dish with fresh recording media. A gravity driven superfusion system is used to apply test solutions directly to the cell under evaluation. This system consists of an array of glass pipette connected to a motorized horizontal translator. The outlet of the shooter is positioned approximately 100 µm from the cell of interest.

Whole cell currents are recorded using the whole-cell patch clamp configuration using an Axopatch 200B amplifier (Axon Instruments, Foster City Calif.), 1322A A/D converter (Axon Instruments) and pClamp software (v. 8; Axon Instruments) and stored on a personal computer. Gigaseals are formed and the whole-cell configuration is established in voltage clamp mode, and membrane currents generated by $hNa_v1.7$ are recorded in gap-free mode. Borosilicate glass pipettes have resistance values between 1.5 and 2.0 MΩ when filled with pipette solution and series resistance (<5 MΩ) was compensated 75-80%. Signals are sampled at 50 kHz and low pass filtered at 3 kHz.

Voltage Protocols: After establishing the whole-cell configuration in voltage clamp mode, voltage protocols are run to establish the 1) test potential, 2) holding potential, and 3) the conditioning potential for each cell.

After establishing the whole-cell configuration in voltage clamp mode, a standard I-V protocol is run to determine the potential at which the maximal current ($I_{max}$) is elicited. This potential is the test potential ($V_t$). To determine a conditioning potential at which 100% of channels are in the inactivated state, a standard steady-state inactivation (SSIN) protocol is run using a series of fifteen 100 ms-long depolarizing prepulses, incrementing in 10 mV steps, immediately followed by a 5 ms testing pulse, $V_t$, to $V_{max}$. This protocol also permits determination of the holding potential at which all channels are in the resting state.

For compounds causing significant retardation of recovery from inactivation, an estimate of the affinity for the inactivated state of the channel ($K_i$) is generated using the following protocol. From the negative, no residual inactivation, holding potential, the cell is depolarized to the conditioning voltage for 2-5 seconds, returned to the negative holding potential for 10-20 ms to relieve fast inactivation and then depolarized to the test potential for ~15 ms. This voltage protocol is repeated every 10-15 seconds, first to establish a baseline in the absence of the test compound, then in the presence of the test compound.

After a stable baseline is established, the test compound is applied and block of the current elicited by the test pulse assessed. In some cases, multiple cumulative concentrations are applied to identify a concentration that blocked between 40-60% of this current. Washout of the compound is attempted by superfusing with control solution once steady-state block is observed. An estimate of the $K_i$ is calculated as follows:

$$K_i=[\text{drug}]*\{FR/(1-FR)\}, \qquad \text{Eq. 1}$$

where [drug] is the concentration of a drug, and $$FR=I(\text{after drug})/I(\text{control}), \qquad \text{Eq. 2}$$

where I is the peak current amplitude. If multiple concentrations were used, $K_i$ is determined from the fit of a logistic equation to FRs plotted against corresponding drug concentrations.

In the alternative, the voltage clamp protocol to examine $hNa_v1.7$ currents is as follows. First, the standard current-voltage relationship was tested by pulsing the cell from the holding voltage ($V_h$) of −120 mV by a series of 5 msec long square-shaped test pulses incrementing in +10 mV steps over the membrane voltage range of −90 mV to +60 mV at the pace of stimulation of 0.5 Hz. This procedure determines the voltage that elicits the maximal current ($V_{max}$). Second, $V_h$ is re-set to −120 mV and a steady-state inactivation (SSIN) curve is taken by the standard double-pulse protocol: 100 ms depolarizing pre-pulse was incremented in steps of +10 mV (voltage range from −90 mV to 0 mV) immediately followed by the 5 ms long test pulse to −10 mV at the pace of stimulation of 0.2 Hz. This procedure determines the voltage of full inactivation ($V_{full}$). Third, the cell is repeatedly stimulated with the following protocol, first in the absence of the test compound then in its presence. The protocol consists of depolarizing the cell from the holding potential of −120 mV to the $V_{full}$ value for 4.5 seconds then repolarizing the cell to the holding potential for 10 ms before applying the test pulse to the $V_{max}$ for 5 ms. The amount of inhibition produced by the test compound is determined by comparing the current amplitude elicited by the test pulse in the absence and presence of the compound.

In a further alternative, the voltage clamp protocol to examine $hNa_v1.7$ currents is as follows. After establishing the whole-cell configuration in voltage clamp mode, two voltage protocols were run to establish: 1) the holding potential; and 2) the test potential for each cell.

Resting block: To determine a membrane potential at which the majority of channels are in the resting state, a standard steady-state inactivation (SSIN) protocol is run using 100 ms prepulses×10 mV depolarizing steps. The holding potential for testing resting block ($Vh_1$) is typically 20 mV more hyperpolarized than the first potential where inactivation is observed with the inactivation protocol.

From this holding potential a standard I-V protocol is run to determine the potential at which the maximal current (Imax) is elicited. This potential is the test potential (Vt).

The compound testing protocol is a series of 10 ms depolarizations from the $Vh_1$ (determined from the SSIN) to the Vt (determined from the I-V protocol) repeated every 10-15 seconds. After a stable baseline is established, a high concentration of a test compound (highest concentration solubility permits or that which provides ~50% block) is applied and block of the current assessed. Washout of the compound is attempted by superfusing with control solution once steady-state block was observed.

The fractional response is calculated as follows:

$$K_r=[\text{drug}]*\{FR/(1-FR)\}, \qquad \text{Eq. 3}$$

where [drug] is the concentration of a drug, and $$FR=I(\text{after drug})/I(\text{control}), \qquad \text{Eq. 2}$$

where I is the peak current amplitude and was used for estimating resting block dissociation constant, $K_r$.

Block of inactivated channels: To assess the block of inactivated channels the holding potential is depolarized such that 20-50% of the current amplitude is reduced when pulsed to the same Vt as above. The magnitude of this depolarization depends upon the initial current amplitude and the rate of current loss due to slow inactivation. This is the second holding potential ($Vh_2$). The current reduction is recorded to determine the fraction of available channels at this potential (h).

$$h=I@Vh_2/I\text{max}. \qquad \text{Eq. 4}$$

At this membrane voltage a proportion of channels was in the inactivated state, and thus inhibition by a blocker includes interaction with both resting and inactivated channels.

To determine the potency of the test compound on inactivated channels, a series of currents are elicited by 10 ms voltage steps from $Vh_2$ to Vt every 10-15 seconds. After establishing a stable baseline, the low concentration of the compound is applied. In some cases, multiple cumulative concentrations will have to be applied to identify a concentration that blocks between 40-60% of the current. Washout is attempted to re-establish baseline. Fractional responses are measured with respect to a projected baseline to determine $K_{app}$.

$$K_{app}=[\text{drug}]*\{FR/(1-FR)\}, \qquad \text{Eq. 5}$$

where [drug] is the concentration of a drug.

This $K_{app}$ value, along with the calculated $K_r$ and h values, are used to calculate the affinity of the compound for the inactivated channels ($K_i$) using the following equation:

$$K_i=(1-h)/((1/K_{app})-(h/K_r)). \qquad \text{Eq. 6}$$

Solutions and chemicals: For electrophysiological recordings the external solution is either standard, DMEM supplemented with 10 mM HEPES (pH adjusted to 7.34 with NaOH and the osmolarity adjusted to 320) or Tyrodes salt solution (Sigma, USA) supplemented with 10 mM HEPES (pH adjusted to 7.4 with NaOH; osmolarity=320). The internal pipette solution contains (in mM): NaCl (10), CsF (140), $CaCl_2$ (1), $MgCl_2$ (5), EGTA (11), HEPES (10: pH 7.4, 305 mOsm). Compounds are prepared first as series of stock solutions in DMSO and then dissolved in external solution; DMSO content in final dilutions did not exceed 0.3%. At this concentration, DMSO does not affect sodium currents. Vehicle solution used to establish base line also contains 0.3% DMSO.

Data analysis: Data is analyzed off-line using Clampfit software (pClamp, v.8; Axon Instruments) and graphed using GraphPad Prizm (v. 4.0) software.

In Vivo Assay for Pain

The compounds can be tested for their antinociceptive activity in the formalin model as described in Hunskaar et al., *J. Neurosci. Methods* 14: 69-76 (1985). Male Swiss Webster NIH mice (20-30 g; Harlan, San Diego, Calif.) can be used in all experiments. Food is withdrawn on the day of experiment. Mice are placed in Plexiglass jars for at least 1 hour to acclimate to the environment. Following the acclimation period, mice are weighed and given either the compound of interest administered i.p. or p.o., or the appropriate volume of vehicle (for example, 10% Tween-80 or 0.9% saline, and other pharmaceutically acceptable vehicles) as control. Fifteen minutes after the i.p. dosing, and 30 minutes after the p.o. dosing mice are injected with formalin (20 μL it of 5% formaldehyde solution in saline)

into the dorsal surface of the right hind paw. Mice are transferred to the Plexiglass jars and monitored for the amount of time spent licking or biting the injected paw. Periods of licking and biting are recorded in 5-minute intervals for 1 hour after the formalin injection. All experiments are done in a blinded manner during the light cycle.

The early phase of the formalin response is measured as licking/biting between 0-5 minutes, and the late phase is measured from 15-50 minutes. Differences between vehicle and drug treated groups can be analyzed by one-way analysis of variance (ANOVA). A P value<0.05 is considered significant. Compounds are considered to be efficacious for treating acute and chronic pain if they have activity in blocking both the early and second phase of formalin-induced paw-licking activity.

In Vivo Assays for Inflammatory or Neuropathic Pain

Test Animals: Each experiment uses rats weighing between 200-260 g at the start of the experiment. The rats are group-housed and have free access to food and water at all times, except prior to oral administration of a test compound when food is removed for 16 hours before dosing. A control group acts as a comparison to rats treated with a Compound of the Invention. The control group is administered the carrier as used for the test compound. The volume of carrier administered to the control group is the same as the volume of carrier and test compound administered to the test group.

Inflammatory Pain: To assess the actions of the compounds of Formulae I-V on the treatment of inflammatory pain the Freund's complete adjuvant ("FCA") model of inflammatory pain is used. FCA-induced inflammation of the rat hind paw is associated with the development of persistent inflammatory mechanical and thermal hyperalgesia and provides reliable prediction of the anti-hyperalgesic action of clinically useful analgesic drugs (Bartho et al., Naunyn-Schmiedeberg's Archives of Pharmacol. 342:666-670 (1990)). The left hind paw of each animal is administered a 50 µL intraplantar injection of 50% FCA. 24 hour post injection, the animal is assessed for response to noxious mechanical stimuli by determining the paw withdrawal threshold (PWT), or to noxious thermal stimuli by determining the paw withdrawal latency (PWL), as described below. Rats are then administered a single injection of either a test compound or 30 mg/Kg of a positive control compound (indomethacin). Responses to noxious mechanical or thermal stimuli are then determined 1, 3, 5 and 24 hours post administration (admin).

Percentage reversal of hyperalgesia for each animal is defined as:

$$\% \text{ reversal} = \frac{\left[\begin{array}{l}(\text{post administration } PWT \text{ or } PWL) - \\ (\text{pre-administration } PWT \text{ or } PWL)\end{array}\right]}{\left[\begin{array}{l}(\text{baseline } PWT \text{ or } PWL) - \\ (\text{pre-administration } PWT \text{ or } PWL)\end{array}\right]} \times 100$$

Neuropathic Pain: To assess the actions of the test compounds for the treatment of neuropathic pain the Seltzer model or the Chung model can be used.

In the Seltzer model, the partial sciatic nerve ligation model of neuropathic pain is used to produce neuropathic hyperalgesia in rats (Seltzer et al., Pain 43:205-218 (1990)). Partial ligation of the left sciatic nerve is performed under isoflurane/$O_2$ inhalation anesthesia. Following induction of anesthesia, the left thigh of the rat is shaved and the sciatic nerve exposed at high thigh level through a small incision and is carefully cleared of surrounding connective tissues at a site near the trocanther just distal to the point at which the posterior biceps semitendinosus nerve branches off of the common sciatic nerve. A 7-0 silk suture is inserted into the nerve with a 38 curved, reversed-cutting mini-needle and tightly ligated so that the dorsal ⅓ to ½ of the nerve thickness is held within the ligature. The wound is closed with a single muscle suture (4-0 nylon (Vicryl)) and vetbond tissue glue. Following surgery, the wound area is dusted with antibiotic powder. Sham-treated rats undergo an identical surgical procedure except that the sciatic nerve is not manipulated. Following surgery, animals are weighed and placed on a warm pad until they recover from anesthesia. Animals are then returned to their home cages until behavioral testing begins.

The animals are assessed for response to noxious mechanical stimuli by determining PWT, as described below, prior to surgery (baseline), then immediately prior to and 1, 3, and 5 hours after drug administration for rear paw of the animal. Percentage reversal of neuropathic hyperalgesia is defined as:

$$\% \text{ reversal} = \frac{\left[\begin{array}{l}(\text{post administration } PWT) - \\ (\text{pre-administration } PWT)\end{array}\right]}{\left[\begin{array}{l}(\text{baseline } PWT) - \\ (\text{pre-administration } PWT)\end{array}\right]} \times 100$$

In the Chung model, the spinal nerve ligation model of neuropathic pain is used to produce mechanical hyperalgesia, thermal hyperalgesia and tactile allodynia in rats. Surgery is performed under isoflurane/$O_2$ inhalation anesthesia. Following induction of anesthesia a 3 cm incision is made and the left paraspinal muscles are separated from the spinous process at the $L_4$-$S_2$ levels. The $L_6$ transverse process is carefully removed with a pair of small rongeurs to identify visually the $L_4$-$L_6$ spinal nerves. The left $L_5$ (or $L_5$ and $L_6$) spinal nerve(s) is (are) isolated and tightly ligated with silk thread. A complete hemostasis is confirmed and the wound is sutured using non-absorbable sutures, such as nylon sutures or stainless steel staples. Sham-treated rats undergo an identical surgical procedure except that the spinal nerve(s) is (are) not manipulated. Following surgery animals are weighed, administered a subcutaneous (s.c.) injection of saline or ringers lactate, the wound area is dusted with antibiotic powder and they are kept on a warm pad until they recover from the anesthesia. Animals are then returned to their home cages until behavioral testing begins.

The animals are assessed for response to noxious mechanical stimuli by determining PWT, as described below, prior to surgery (baseline), then immediately prior to and 1, 3, and 5 hours after being administered a Compound of the Invention for the left rear paw of the animal. The animals can also be assessed for response to noxious thermal stimuli or for tactile allodynia, as described below. The Chung model for neuropathic pain is described in Kim et al., Pain 50(3):355-363 (1992).

Tactile Allodynia: Sensitivity to non-noxious mechanical stimuli can be measured in animals to assess tactile allodynia. Rats are transferred to an elevated testing cage with a wire mesh floor and allowed to acclimate for five to ten minutes. A series of von Frey monofilaments are applied to the plantar surface of the hindpaw to determine the animal's withdrawal threshold. The first filament used possesses a buckling weight of 9.1 gms (0.96 log value) and is applied up to five times to see if it elicits a withdrawal response. If the animal has a withdrawal response, then the next lightest filament in the series would be applied up to five times to determine if it also could elicit a response. This procedure is repeated with subsequent lesser filaments until there is no response and the identity of the lightest filament that elicits a response is recorded. If the animal does not have a withdrawal response from the initial 9.1 gms filament, then subsequent filaments of increased weight are applied until a filament elicits a response and the identity of this filament is recorded. For each animal, three measurements are made at every time point to produce an average withdrawal threshold determination. Tests can be performed prior to, and at 1, 2, 4 and 24 hours post drug administration.

Mechanical Hyperalgesia: Sensitivity to noxious mechanical stimuli can be measured in animals using the paw pressure test to assess mechanical hyperalgesia. In rats, hind paw withdrawal thresholds ("PWT"), measured in grams, in response to a noxious mechanical stimulus are determined using an analgesymeter (Model 7200, commercially available from Ugo Basile of Italy), as described in Stein (*Biochemistry & Behavior* 31: 451-455 (1988)). The rat's paw is placed on a small platform, and weight is applied in a graded manner up to a maximum of 250 grams. The endpoint is taken as the weight at which the paw is completely withdrawn. PWT is determined once for each rat at each time point. PWT can be measured only in the injured paw, or in both the injured and non-injured paw. In one non-limiting embodiment, mechanical hyperalgesia associated with nerve injury induced pain (neuropathic pain) can be assessed in rats. Rats are tested prior to surgery to determine a baseline, or normal, PWT. Rats are tested again 2 to 3 weeks post-surgery, prior to, and at different times after (e.g. 1, 3, 5 and 24 hr) drug administration. An increase in PWT following drug administration indicates that the test compound reduces mechanical hyperalgesia.

In Vivo Assay for Anticonvulsant Activity

Compounds of the Invention can be tested for in vivo anticonvulsant activity after i.v., p.o., or i.p. injection using any of a number of anticonvulsant tests in mice, including the maximum electroshock seizure test (MES). Maximum electroshock seizures are induced in male NSA mice weighing between 15-20 g and in male Sprague-Dawley rats weighing between 200-225 g by application of current (for mice: 50 mA, 60 pulses/sec, 0.8 msec pulse width, 1 sec duration, D.C.; for rats: 99 mA, 125 pulses/sec, 0.8 msec pulse width, 2 sec duration, D.C.) using a Ugo Basile ECT device (Model 7801). Mice are restrained by gripping the loose skin on their dorsal surface and saline-coated corneal electrodes are held lightly against the two corneae. Rats are allowed free movement on the bench top and ear-clip electrodes are used. Current is applied and animals are observed for a period of up to 30 seconds for the occurrence of a tonic hindlimb extensor response. A tonic seizure is defined as a hindlimb extension in excess of 90 degrees from the plane of the body. Results can be treated in a quantal manner.

Pharmaceutical Compositions

Although a Compound of the Invention can be administered to a mammal in the form of a raw chemical without any other components present, the compound is preferably administered as part of a pharmaceutical composition containing the compound combined with a suitable pharmaceutically acceptable carrier. Such a carrier can be selected from pharmaceutically acceptable excipients and auxiliaries.

Pharmaceutical compositions within the scope of the invention include all compositions where a Compound of the Invention is combined with a pharmaceutically acceptable carrier. In one embodiment, the compound is present in the composition in an amount that is effective to achieve its intended therapeutic purpose. While individual needs may vary, a determination of optimal ranges of effective amounts of each compound is within the skill of the art.

Typically, a compound can be administered to a mammal, e.g., a human, orally at a dose of from about 0.0025 to about 1500 mg per kg body weight of the mammal, or an equivalent amount of a pharmaceutically acceptable salt, hydrate, diastereomer, or solvate thereof, per day to treat the particular disorder. A useful oral dose of a Compound of the Invention administered to a mammal is from about 0.0025 to about 50 mg per kg body weight of the mammal, or an equivalent amount of the pharmaceutically acceptable salt, hydrate, diastereomer, or solvate thereof. For intramuscular injection, the dose is typically about one-half of the oral dose.

A unit oral dose may comprise from about 0.01 to about 50 mg, and preferably about 0.1 to about 10 mg, of the compound. The unit dose can be administered one or more times daily, e.g., as one or more tablets or capsules, each containing from about 0.01 to about 50 mg of the compound, or an equivalent amount of a pharmaceutically acceptable salt, hydrate, diastereomer, or solvate thereof.

A pharmaceutical composition of the invention can be administered to any animal that may experience the beneficial effects of a Compound of the Invention. Foremost among such animals are mammals, e.g., humans and companion animals, although the invention is not intended to be so limited.

A pharmaceutical composition of the invention can be administered by any means that achieves its intended purpose. For example, administration can be by the oral, parenteral, subcutaneous, intravenous, intramuscular, intraperitoneal, transdermal, intranasal, transmucosal, rectal, intravaginal or buccal route, or by inhalation. The dosage administered and route of administration will vary, depending upon the circumstances of the particular subject, and taking into account such factors as age, gender, health, and weight of the recipient, condition or disorder to be treated, kind of concurrent treatment, if any, frequency of treatment, and the nature of the effect desired.

In one embodiment, a pharmaceutical composition of the invention can be administered orally and is formulated into tablets, dragees, capsules or an oral liquid preparation. In one embodiment, the oral formulation comprises extruded multiparticulates comprising the Compound of the Invention.

Alternatively, a pharmaceutical composition of the invention can be administered rectally, and is formulated in suppositories.

Alternatively, a pharmaceutical composition of the invention can be administered by injection.

Alternatively, a pharmaceutical composition of the invention can be administered transdermally.

Alternatively, a pharmaceutical composition of the invention can be administered by inhalation or by intranasal or transmucosal administration.

Alternatively, a pharmaceutical composition of the invention can be administered by the intravaginal route.

A pharmaceutical composition of the invention can contain from about 0.01 to 99 percent by weight, and preferably from about 0.25 to 75 percent by weight, of active compound(s).

A method of the invention, such as, a method for treating a disorder responsive to the blockade of one or more sodium channels in an animal in need thereof, can further comprise administering a second therapeutic agent to the animal in combination with a Compound of the Invention. In one embodiment, the other therapeutic agent is administered in an effective amount.

Effective amounts of the other therapeutic agents are known to those skilled in the art. However, it is well within the skilled artisan's purview to determine the other therapeutic agent's optimal effective-amount range.

A Compound of the Invention (i.e., the first therapeutic agent) and the second therapeutic agent can act additively or, in one embodiment, synergistically. Alternatively, the second therapeutic agent can be used to treat a disorder or condition that is different from the disorder or condition for which the first therapeutic agent is being administered, and which disorder or condition may or may not be a condition or disorder as defined herein.

In one embodiment, a Compound of the Invention is administered concurrently with a second therapeutic agent; for example, a single composition comprising both an effective amount of a Compound of the Invention, and an effective amount of the second therapeutic agent can be administered.

Accordingly, the invention further provides a pharmaceutical composition comprising a combination of a Compound of the Invention, the second therapeutic agent, and a pharmaceutically acceptable diluent or carrier.

Alternatively, a first pharmaceutical composition comprising an effective amount of a Compound of the Invention and a second pharmaceutical composition comprising an effective amount of the second therapeutic agent can be concurrently administered.

In another embodiment, an effective amount of a Compound of the Invention is administered prior or subsequent to administration of an effective amount of the second therapeutic agent. In this embodiment, the Compound of the Invention is administered while the second therapeutic agent exerts its therapeutic effect, or the second therapeutic agent is administered while the Compound of the Invention exerts its therapeutic effect for treating a disorder or condition.

The second therapeutic agent can be an opioid agonist, a non-opioid analgesic, a non-steroidal anti-inflammatory agent, an antimigraine agent, a Cox-II inhibitor, a β-adrenergic blocker, an anticonvulsant, an antidepressant, an anticancer agent, an agent for treating addictive disorder, an agent for treating Parkinson's disease and parkinsonism, an agent for treating anxiety, an agent for treating epilepsy, an agent for treating a seizure, an agent for treating a stroke, an agent for treating a pruritic condition, an agent for treating psychosis, an agent for treating ALS, an agent for treating a cognitive disorder, an agent for treating a migraine, an agent for treating vomiting, an agent for treating dyskinesia, or an agent for treating depression, or a mixture thereof.

Examples of useful opioid agonists include, but are not limited to, alfentanil, allylprodine, alphaprodine, anileridine, benzylmorphine, bezitramide, buprenorphine, butorphanol, clonitazene, codeine, desomorphine, dextromoramide, dezocine, diampromide, diamorphone, dihydrocodeine, dihydromorphine, dimenoxadol, dimepheptanol, dimethylthiambutene, dioxaphetyl butyrate, dipipanone, eptazocine, ethoheptazine, ethylmethylthiambutene, ethylmorphine, etonitazene, fentanyl, heroin, hydrocodone, hydromorphone, hydroxypethidine, isomethadone, ketobemidone, levorphanol, levophenacylmorphan, lofentanil, meperidine, meptazinol, metazocine, methadone, metopon, morphine, myrophine, nalbuphine, narceine, nicomorphine, norlevorphanol, normethadone, nalorphine, normorphine, norpipanone, opium, oxycodone, oxymorphone, papavereturn, pentazocine, phenadoxone, phenomorphan, phenazocine, phenoperidine, piminodine, piritramide, proheptazine, promedol, properidine, propiram, propoxyphene, sufentanil, tilidine, tramadol, pharmaceutically acceptable salts thereof, and mixtures thereof.

In certain embodiments, the opioid agonist is selected from codeine, hydromorphone, hydrocodone, oxycodone, dihydrocodeine, dihydromorphine, morphine, tramadol, oxymorphone, pharmaceutically acceptable salts thereof, and mixtures thereof.

Examples of useful non-opioid analgesics include non-steroidal anti-inflammatory agents, such as aspirin, ibuprofen, diclofenac, naproxen, benoxaprofen, flurbiprofen, fenoprofen, flubufen, ketoprofen, indoprofen, piroprofen, carprofen, oxaprozin, pramoprofen, muroprofen, trioxaprofen, suprofen, aminoprofen, tiaprofenic acid, fluprofen, bucloxic acid, indomethacin, sulindac, tolmetin, zomepirac, tiopinac, zidometacin, acemetacin, fentiazac, clidanac, oxpinac, mefenamic acid, meclofenamic acid, flufenamic acid, niflumic acid, tolfenamic acid, diflurisal, flufenisal, piroxicam, sudoxicam, isoxicam, and pharmaceutically acceptable salts thereof, and mixtures thereof. Examples of other suitable non-opioid analgesics include the following, non limiting, chemical classes of analgesic, antipyretic, nonsteroidal antiinflammatory drugs: salicylic acid derivatives, including aspirin, sodium salicylate, choline magnesium trisalicylate, salsalate, diflunisal, salicylsalicylic acid, sulfasalazine, and olsalazin; para aminophennol derivatives including acetaminophen and phenacetin; indole and indene acetic acids, including indomethacin, sulindac, and etodolac; heteroaryl acetic acids, including tolmetin, diclofenac, and ketorolac; anthranilic acids (fenamates), including mefenamic acid, and meclofenamic acid; enolic acids, including oxicams (piroxicam, tenoxicam), and pyrazolidinediones (phenylbutazone, oxyphenthartazone); and alkanones, including nabumetone. For a more detailed description of the NSAIDs, see Paul A. Inset, *Analgesic Antipyretic and Antiinflammatory Agents and Drugs Employed in the Treatment of Gout*, in Goodman & Gilman's *The Pharmacological Basis of Therapeutics* 617-57 (Perry B. Molinhoff and Raymond W. Ruddon eds., 9th ed 1996) and Glen R. Hanson, *Analgesic, Antipyretic and Anti Inflammatory Drugs* in Remington: *The Science and Practice of Pharmacy* Vol. II 1196-1221 (A. R. Gennaro ed. 19th ed. 1995) which are hereby incorporated by reference in their entireties. Suitable Cox-II inhibitors and 5-lipoxygenase inhibitors, as well as combinations thereof, are described in U.S. Pat. No. 6,136,839, which is hereby incorporated by reference in its entirety. Examples of useful Cox II inhibitors include, but are not limited to, rofecoxib and celecoxib.

Examples of useful antimigraine agents include, but are not limited to, alpiropride, bromocriptine, dihydroergotamine, dolasetron, ergocornine, ergocorninine, ergocryptine, ergonovine, ergot, ergotamine, flumedroxone acetate, fonazine, ketanserin, lisuride, lomerizine, methylergonovine, methysergide, metoprolol, naratriptan, oxetorone, pizotyline, propranolol, risperidone, rizatriptan, sumatriptan, timolol, trazodone, zolmitriptan, and mixtures thereof.

Examples of useful β-adrenergic blockers include, but are not limited to, acebutolol, alprenolol, amosulabol, arotinolol, atenolol, befunolol, betaxolol, bevantolol, bisoprolol, bopindolol, bucumolol, bufetolol, bufuralol, bunitrolol, bupranolol, butidrine hydrochloride, butofilolol, carazolol, carteolol, carvedilol, celiprolol, cetamolol, cloranolol, dilevalol, epanolol, esmolol, indenolol, labetalol, levobunolol, mepindolol, metipranolol, metoprolol, moprolol, nadolol, nadoxolol, nebivalol, nifenalol, nipradilol, oxprenolol, penbutolol, pindolol, practolol, pronethalol, propranolol, sotalol, sulfinalol, talinolol, tertatolol, tilisolol, timolol, toliprolol, and xibenolol.

Examples of useful anticonvulsants include, but are not limited to, acetylpheneturide, albutoin, aloxidone, aminoglutethimide, 4-amino-3-hydroxybutyric acid, atrolactamide, beclamide, buramate, calcium bromide, carbamazepine, cinromide, clomethiazole, clonazepam, decimemide, diethadione, dimethadione, doxenitroin, eterobarb, ethadione, ethosuximide, ethotoin, felbamate, fluoresone, gabapentin, 5-hydroxytryptophan, lamotrigine, magnesium bromide, magnesium sulfate, mephenyloin, mephobarbital, metharbital, methetoin, methsuximide, 5-methyl-5-(3-phenanthryl)-hydantoin, 3-methyl-5-phenyl-hydantoin, narcobarbital, nimetazepam, nitrazepam, oxcarbazepine, paramethadione, phenacemide, phenetharbital, pheneturide, phenobarbital, phensuximide, phenylmethylbarbituric acid, phenyloin, phethenylate sodium, potassium bromide, pregabaline, primidone, progabide, sodium bromide, *solanum*, strontium bromide, suclofenide, sulthiame, tetrantoin, tiagabine, topiramate, trimethadione, valproic acid, valpromide, vigabatrin, and zonisamide.

Examples of useful antidepressants include, but are not limited to, binedaline, caroxazone, citalopram, (S)-citalopram, dimethazan, fencamine, indalpine, indeloxazine hydrocholoride, nefopam, nomifensine, oxitriptan, oxypertine, paroxetine, sertraline, thiazesim, trazodone, benmoxine, iproclozide, iproniazid, isocarboxazid, nialamide, octamoxin, phenelzine, cotinine, rolicyprine, rolipram, maprotiline, metralindole, mianserin, mirtazepine, adinazolam, amitriptyline, amitriptylinoxide, amoxapine, butriptyline, clomipramine, demexiptiline, desipramine, dibenzepin, dimetacrine, dothiepin, doxepin, fluacizine, imipramine, imipramine N-oxide, iprindole, lofepramine, melitracen, metapramine, nortriptyline, noxiptilin, opipramol, pizotyline, propizepine, protriptyline, quinupramine, tianeptine, trimipramine, adrafinil, benactyzine, bupropion, butacetin, dioxadrol, duloxetine, etoperidone, febarbamate, femoxetine, fenpentadiol, fluoxetine, fluvoxamine, hematoporphyrin, hypericin, levophacetoperane, medifoxamine, milnacipran, minaprine, moclobemide, nefazodone, oxaflozane, piberaline, prolintane, pyrisuccideanol, ritanserin, roxindole, rubidium chloride, sulpiride, tandospirone, thozalinone, tofenacin, toloxatone, tranylcypromine, L-tryptophan, venlafaxine, viloxazine, and zimeldine.

Examples of useful anticancer agents include, but are not limited to, acivicin, aclarubicin, acodazole hydrochloride, acronine, adozelesin, aldesleukin, altretamine, ambomycin, ametantrone acetate, aminoglutethimide, amsacrine, anastrozole, anthramycin, asparaginase, asperlin, azacitidine, azetepa, azotomycin, batimastat, benzodepa, bicalutamide, bisantrene hydrochloride, bisnafide dimesylate, bizelesin, bleomycin sulfate, brequinar sodium, bropirimine, busulfan, cactinomycin, calusterone, caracemide, carbetimer, carboplatin, carmustine, carubicin hydrochloride, carzelesin, cedefingol, chlorambucil, cirolemycin, and cisplatin.

Therapeutic agents useful for treating an addictive disorder include, but are not limited to, methadone, desipramine, amantadine, fluoxetine, buprenorphine, an opiate agonist, 3-phenoxypyridine, or a serotonin antagonist.

Examples of useful therapeutic agents for treating Parkinson's disease and parkinsonism include, but are not limited to, carbidopalevodopa, pergolide, bromocriptine, ropinirole, pramipexole, entacapone, tolcapone, selegiline, amantadine, and trihexyphenidyl hydrochloride.

Examples of useful therapeutic agents for treating anxiety include, but are not limited to, benzodiazepines, such as alprazolam, brotizolam, chlordiazepoxide, clobazam, clonazepam, clorazepate, demoxepam, diazepam, estazolam, flumazenil, flurazepam, halazepam, lorazepam, midazolam, nitrazepam, nordazepam, oxazepam, prazepam, quazepam, temazepam, and triazolam; non-benzodiazepine agents, such as buspirone, gepirone, ipsapirone, tiospirone, zolpicone, zolpidem, and zaleplon; tranquilizers, such as barbituates, e.g., amobarbital, aprobarbital, butabarbital, butalbital, mephobarbital, methohexital, pentobarbital, phenobarbital, secobarbital, and thiopental; and propanediol carbamates, such as meprobamate and tybamate.

Examples of useful therapeutic agents for treating epilepsy or seizure include, but are not limited to, carbamazepine, ethosuximide, gabapentin, lamotrigine, phenobarbital, phenyloin, primidone, valproic acid, trimethadione, benzodiazepines, gamma-vinyl GABA, acetazolamide, and felbamate.

Examples of useful therapeutic agents for treating stroke include, but are not limited to, anticoagulants such as heparin, agents that break up clots such as streptokinase or tissue plasminogen activator, agents that reduce swelling such as mannitol or corticosteroids, and acetylsalicylic acid.

Examples of useful therapeutic agents for treating a pruritic condition include, but are not limited to, naltrexone; nalmefene; danazol; tricyclics such as amitriptyline, imipramine, and doxepin; antidepressants such as those given below; menthol; camphor; phenol; pramoxine; capsaicin; tar; steroids; and antihistamines.

Examples of useful therapeutic agents for treating psychosis include, but are not limited to, phenothiazines such as chlorpromazine hydrochloride, mesoridazine besylate, and thoridazine hydrochloride; thioxanthenes such as chloroprothixene and thiothixene hydrochloride; clozapine; risperidone; olanzapine; quetiapine; quetiapine fumarate; haloperidol; haloperidol decanoate; loxapine succinate; molindone hydrochloride; pimozide; and ziprasidone.

Examples of useful therapeutic agents for treating ALS include, but are not limited to, baclofen, neurotrophic factors, riluzole, tizanidine, benzodiazepines such as clonazepan and dantrolene.

Examples of useful therapeutic agents for treating cognitive disorders include, but are not limited to, agents for treating dementia such as tacrine; donepezil; ibuprofen; antipsychotic drugs such as thioridazine and haloperidol; and antidepressant drugs such as those given below.

Examples of useful therapeutic agents for treating a migraine include, but are not limited to, sumatriptan; methysergide; ergotamine; caffeine; and beta-blockers such as propranolol, verapamil, and divalproex.

Examples of useful therapeutic agents for treating vomiting include, but are not limited to, 5-HT3 receptor antagonists such as ondansetron, dolasetron, granisetron, and tropisetron; dopamine receptor antagonists such as prochlorperazine, thiethylperazine, chlorpromazine, metoclopramide, and domperidone; glucocorticoids such as dexamethasone; and benzodiazepines such as lorazepam and alprazolam.

Examples of useful therapeutic agents for treating dyskinesia include, but are not limited to, reserpine and tetrabenazine.

Examples of useful therapeutic agents for treating depression include, but are not limited to, tricyclic antidepressants such as amitryptyline, amoxapine, bupropion, clomipramine, desipramine, doxepin, imipramine, maprotiline, nefazadone, nortriptyline, protriptyline, trazodone, trimipramine, and venlafaxine; selective serotonin reuptake inhibitors such as citalopram, (S)-citalopram, fluoxetine, fluvoxamine, paroxetine, and setraline; monoamine oxidase inhibitors such as isocarboxazid, pargyline, phenelzine, and tranylcypromine; and psychostimulants such as dextroamphetamine and methylphenidate.

A pharmaceutical composition of the invention is manufactured in a manner which itself will be known in view of the instant disclosure, for example, by means of conventional mixing, granulating, dragee-making, dissolving, extrusion, or lyophilizing processes. Thus, pharmaceutical compositions for oral use can be obtained by combining the active compound with solid excipients, optionally grinding the resulting mixture and processing the mixture of granules, after adding suitable auxiliaries, if desired or necessary, to obtain tablets or dragee cores.

In addition to a Compound (or Compounds) of the Invention, a pharmaceutical composition of the invention may contain inert diluents commonly used in the art, such as, water or other solvents, solubilizing agents and emulsifiers, such as, ethyl alcohol, isopropyl alcohol, 1,3-butylene glycol, oils (e.g., cottonseed, groundnut, corn, germ, olive, castor, and sesame oils), glycerol, tetrahydrofuryl alcohol, polyethylene glycols, and fatty acid esters of sorbitan, and mixtures thereof.

Suitable excipients include fillers such as saccharides (for example, lactose, sucrose, mannitol or sorbitol), cellulose preparations, calcium phosphates (for example, tricalcium phosphate or calcium hydrogen phosphate), as well as binders such as starch paste (using, for example, maize starch, wheat starch, rice starch, or potato starch), gelatin, tragacanth, methyl cellulose, hydroxypropylmethylcellulose, sodium carboxymethylcellulose, and/or polyvinyl pyrrolidone. If desired, one or more disintegrating agents can be added, such as the above-mentioned starches and also carboxymethyl-starch, cross-linked polyvinyl pyrrolidone, agar, or alginic acid or a salt thereof, such as sodium alginate.

Auxiliaries are typically flow-regulating agents and lubricants such as, for example, silica, talc, stearic acid or salts thereof (e.g., magnesium stearate or calcium stearate), and polyethylene glycol. Dragee cores are provided with suitable coatings that are resistant to gastric juices. For this purpose, concentrated saccharide solutions can be used, which may optionally contain gum arabic, talc, polyvinyl pyrrolidone, polyethylene glycol and/or titanium dioxide, lacquer solutions and suitable organic solvents or solvent mixtures. In order to produce coatings resistant to gastric juices, solutions of suitable cellulose preparations such as acetylcellulose phthalate or hydroxypropymethyl-cellulose phthalate can be used. Dye stuffs or pigments can be added to the tablets or dragee coatings, for example, for identification or in order to characterize combinations of active compound doses.

Examples of other pharmaceutical preparations that can be used orally include push-fit capsules made of gelatin, or soft, sealed capsules made of gelatin and a plasticizer such as glycerol or sorbitol. The push-fit capsules can contain a compound in the form of granules, which can be mixed with fillers such as lactose, binders such as starches, and/or lubricants such as talc or magnesium stearate and, optionally, stabilizers, or in the form of extruded multiparticulates. In soft capsules, the active compounds are preferably dissolved or suspended in suitable liquids, such as fatty oils or liquid paraffin. In addition, stabilizers can be added.

Possible pharmaceutical preparations for rectal administration include, for example, suppositories, which consist of a combination of one or more active compounds with a suppository base. Suitable suppository bases include natural and synthetic triglycerides, and paraffin hydrocarbons, among others. It is also possible to use gelatin rectal capsules consisting of a combination of active compound with a base material such as, for example, a liquid triglyceride, polyethylene glycol, or paraffin hydrocarbon.

Suitable formulations for parenteral administration include aqueous solutions of the active compound in a water-soluble form such as, for example, a water-soluble salt, alkaline solution, or acidic solution. Alternatively, a suspension of the active compound can be prepared as an oily suspension. Suitable lipophilic solvents or vehicles for such as suspension may include fatty oils (for example, sesame oil), synthetic fatty acid esters (for example, ethyl oleate), triglycerides, or a polyethylene glycol such as polyethylene glycol-400 (PEG-400). An aqueous suspension may contain one or more substances to increase the viscosity of the suspension, including, for example, sodium carboxymethyl cellulose, sorbitol, and/or dextran. The suspension may optionally contain stabilizers.

The following examples are illustrative, but not limiting, of the compounds, compositions and methods of the invention. Suitable modifications and adaptations of the variety of conditions and parameters normally encountered in clinical therapy and which are obvious to those skilled in the art in view of this disclosure are within the spirit and scope of the invention.

EXAMPLES

Example 1

Synthesis of $N^1$-(4-(4-fluorophenoxy)phenyl)benzene-1,2-diamine (Compound 7)

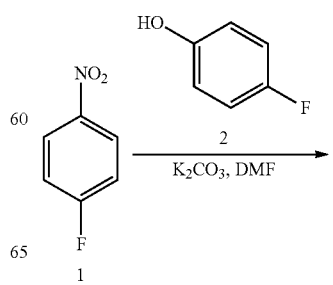

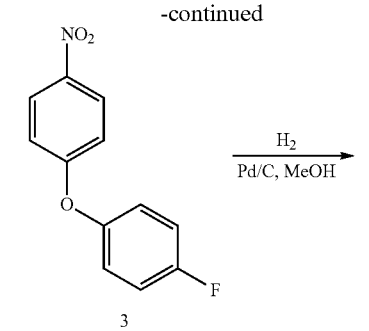

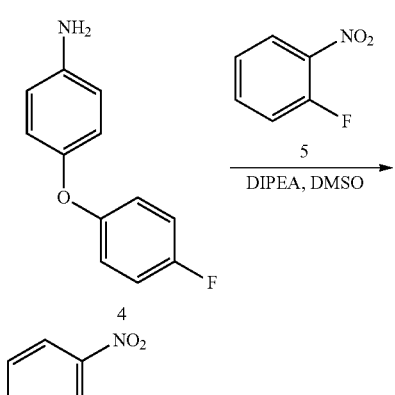

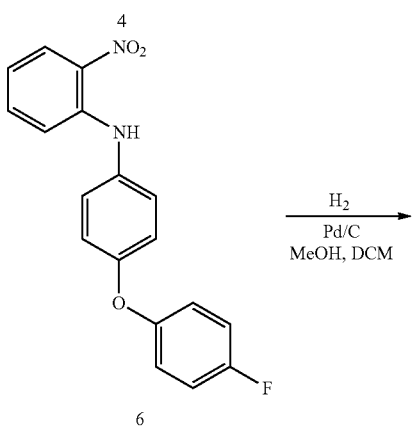

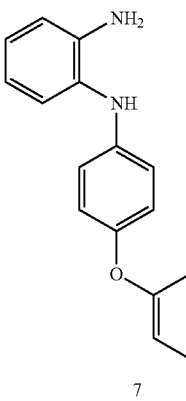

A mixture of 1-fluoro-4-nitrobenzene (Compound 1) (38 g, 0.27 mol), 4-fluorophenol (Compound 2) (30 g, 0.27 mol) and K$_2$CO$_3$ (37.8 g, 0.27 mol) in DMF (300 mL) was heated at 95° C. for 20 h. The reaction mixture was cooled to RT and diluted with EtOAc (150 mL). The organic layer was washed with water, dried over MgSO$_4$ and concentrated. The residue was purified by flash chromatography (SiO$_2$, 5% EtOA/chexanes) to give Compound 3 as brown crystals (44 g, 70% yield). $^1$H NMR (400 MHz, CDCl$_3$): δ 8.20 (d, J=9.4 Hz, 2H), 7.04-7.17 (m, 4H), 6.99 (d, J=9.4, 2H).

Compound 3 (23.3 g, 0.1 mol) was dissolved in MeOH (50 mL) and 5% Pd/C (50 mg) was added. The reaction mixture was hydrogenated at RT under a balloon of hydrogen for 16 h. The reaction mixture was filtered through Celite and the filtrate concentrated to give Compound 4 as an off-white solid (20.4 g, 100% yield). LC/MS: m/z=204.3 [M+H]$^+$ (Calc: 203.2).

A mixture of Compound 4 (1.02 g, 5.0 mmol), 1-fluoro-2-nitrobenzene (Compound 5) (0.71 g, 5.0 mmol) and DIPEA (1 mL) in DMSO (2 mL) was heated at 150° C. in a microwave reactor (Milestone MicroSYNTH) for 2 h. After cooling to RT the reaction mixture was diluted with water and extracted with DCM (3×100 mL). The combined organic layers were dried over Na$_2$SO$_4$, concentrated and the residue purified by flash chromatography (SiO$_2$, 5% MeOH/DCM) to give Compound 6 (1.38 g, 85% yield). LC/MS: m/z=325.2 [M+H]$^+$ (Calc: 324.3).

Compound 6 (3.6 g, 11.1 mol) was dissolved in a mixture of MeOH (60 mL) and DCM (20 mL), 10% Pd/C (360 mg) was added and the mixture hydrogenated at RT at 50 psi of hydrogen for 3 h. The reaction mixture was filtered through Celite and the filtrate concentrated to give Compound 7 as an off-white solid (2.94 g, 90% yield). This material was of adequate purity for subsequent reactions. LC/MS: m/z=295.2 [M+H]$^+$ (Calc: 294.3).

Example 2

1-(4-(4-Fluorophenoxy)phenyl)-2-(tetrahydro-2H-pyran-4-yl)-1H-benzo[d]imidazole (Compound 9)

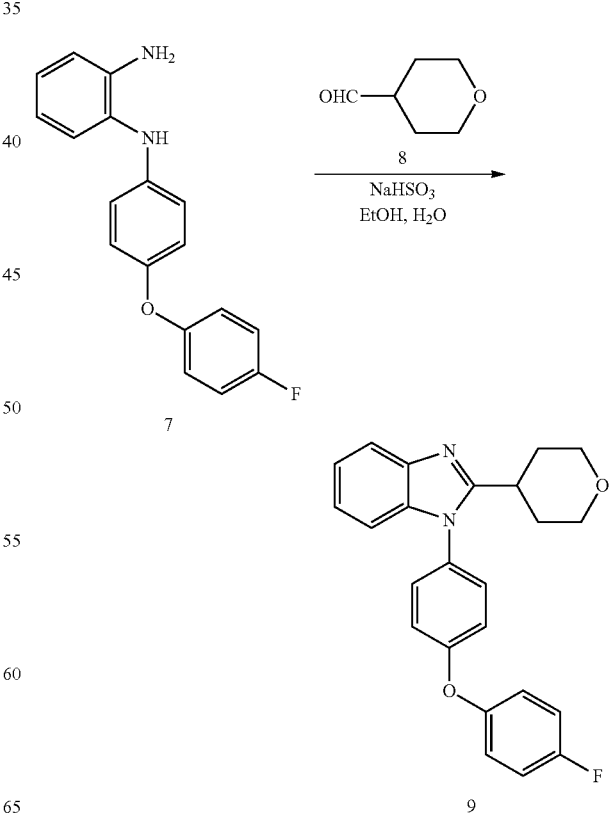

To a solution of Compound 7 (147.2 mg, 0.5 mmol) in EtOH (1 mL) was added Compound 8 (57.1 mg, 0.5 mmol) and 40% aq. NaHSO$_3$ (1.1 mL) at RT. The reaction mixture was heated at 150° C. in a microwave reactor for 30 min. After cooling to RT the reaction mixture was diluted water and extracted with DCM (3×100 mL). The combined organic layers were dried over Na$_2$SO$_4$, concentrated and the residue purified by flash chromatography (SiO$_2$, 0-15% MeOH/DCM) to give Compound 9 (97 mg, 50% yield): $^1$H NMR (400 MHz, CD$_3$OD): δ 7.58 (d, J=8.0 Hz, 1H), 7.35 (m, 2H), 7.18 (m, 1H), 7.14-7.08 (m, 7H), 6.99 (d, J=8.0 Hz, 1H), 3.89 (m, 2H), 3.31 (m, 2H), 2.99 (m, 1H), 1.98 (m, 1H), 1.71 (m, 2H). LC/MS: m/z=389.2 [M+H]$^+$ (Calc: 388.4).

In a similar manner, the following compounds were prepared:

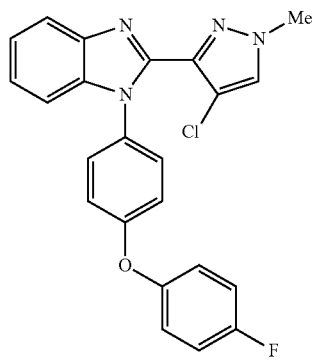

10

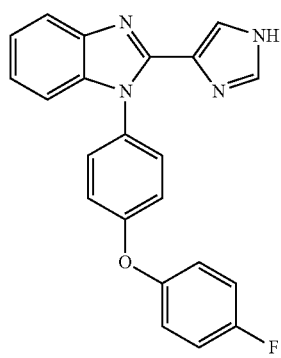

11

2-(4-Chloro-1-methyl-1H-pyrazol-3-yl)-1-(4-(4-fluorophenoxy)phenyl)-1H-benzo[d]imidazole (Compound 10): $^1$H NMR (400 MHz, CD$_3$OD): δ 7.81 (m, 2H), 7.44-7.31 (m, 5H), 7.20-7.05 (m, 6H), 3.88 (s, 3H). LC/MS: m/z=419.1 [M+H]$^+$ (Calc: 418.9).

1-(4-(4-fluorophenoxy)phenyl)-2-(1H-imidazol-4-yl)-1H-benzo[d]imidazole (Compound 11): $^1$H NMR (400 MHz, CD$_3$OD): δ 7.73 (m, 2H), 7.41 (m, 2H), 7.32 (m, 3H), 7.19 (m, 7H). LC/MS: m/z=371.1 [M+H]$^+$ (Calc: 370.4).

Example 3

(S)-5-(1-(4-(4-fluorophenoxy)phenyl)-1H-benzo[d]imidazol-2-yl)pyrrolidin-2-one (Compound 14)

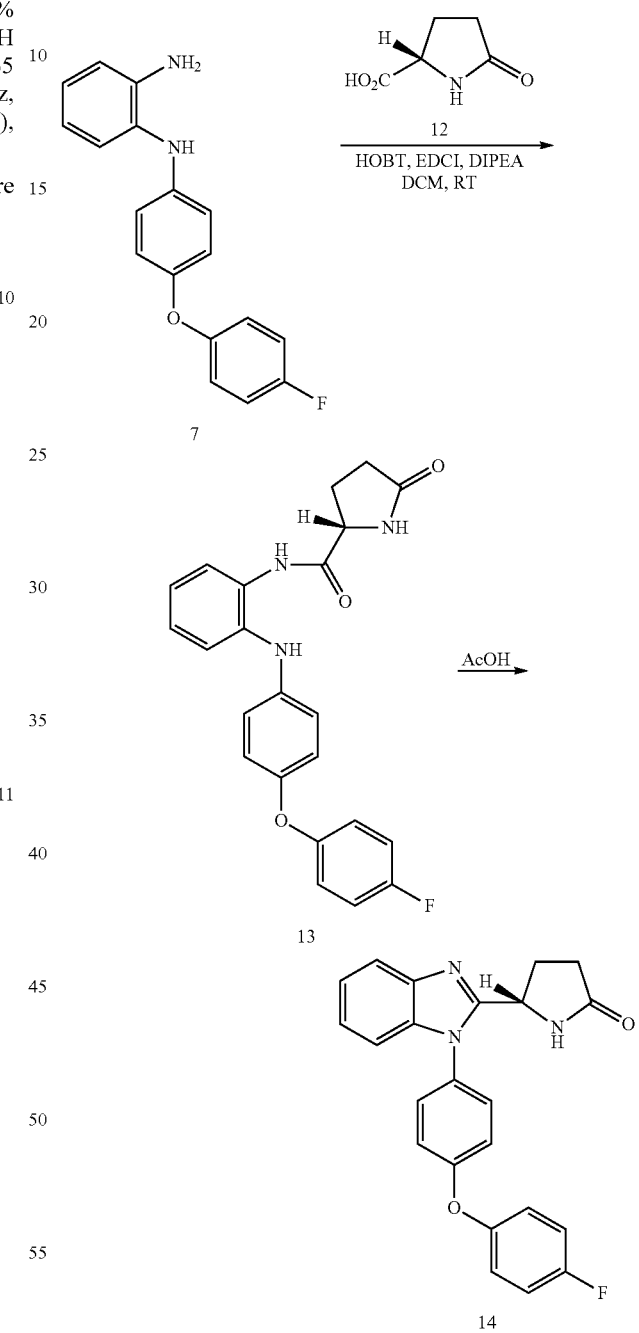

To a mixture of Compound 7 (200 mg, 0.68 mmol) and Compound 12 (88 mg, 0.68 mmol) in DCM (10 mL) was added HOBt (135 mg, 1.0 mmol), EDCI (192 mg, 1.0 mmol) and DIPEA (0.4 mL) at RT. The reaction mixture was stirred at RT for 16 h, quenched by the addition of water and extracted with DCM. The combined organic layers were dried over Na$_2$SO$_4$, concentrated and the residue purified by flash chromatography (SiO$_2$, 0-15% MeOH/DCM) to give Compound 13 (200 mg, 72% yield). LC/MS: m/z=406.3 [M+H]$^+$ (Calc: 405.4).

A mixture of Compound 13 (200 mg, 0.49 mmol) and AcOH (0.4 mL) in toluene (10 mL) was heated at 160° C. in a microwave reactor for 1 h. After cooling to RT, the reaction was quenched by the addition of satd. aq. NaHCO$_3$ and the mixture extracted with DCM. The combined organic layers were dried over Na$_2$SO$_4$, concentrated and the residue purified by flash chromatography (SiO$_2$, 30% (10% NH$_4$OH in MeOH) in DCM) to give Compound 14 (143 mg, 75% yield). $^1$H NMR (400 MHz, CD$_3$OD): δ 7.73 (m, 1H), 7.49 (m, 2H), 7.32 (m, 2H), 7.26-7.13 (m, 7H), 4.97 (m, 1H), 2.57-2.31 (m, 4H). LC/MS: m/z=388.2 [M+H]$^+$ (Calc: 387.4).

In a similar manner, the following compounds were prepared:

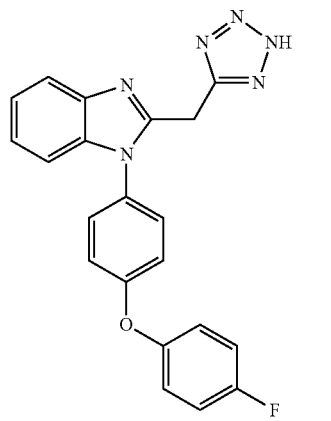

15

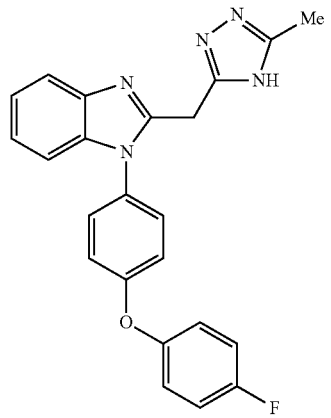

16

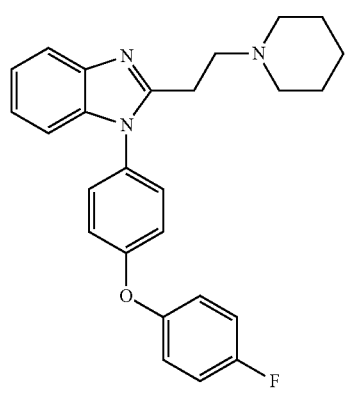

17

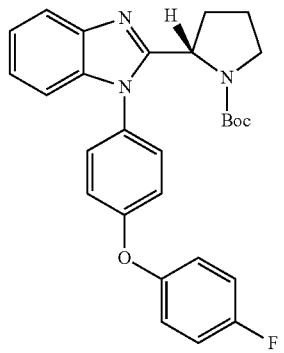

18

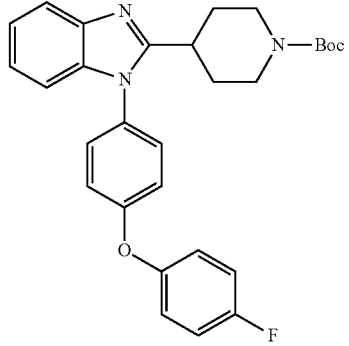

19

2-((1H-tetrazol-5-yl)methyl)-1-(4-(4-fluorophenoxy)phenyl)-1H-benzo[d]imidazole (Compound 15): $^1$H NMR (400 MHz, CD$_3$OD): δ 7.61 (m, 1H), 7.48 (m, 2H), 7.21 (m, 4H), 7.12 (m, 5H), 4.49 (s, 2H). LC/MS: m/z=387.1 [M+H]$^+$ (Calc: 386.4).

1-(4-(4-Fluorophenoxy)phenyl)-2-((5-methyl-4H-1,2,4-triazol-3-yl)methyl)-1H-benzo[d]imidazole (Compound 16): $^1$H NMR (400 MHz, CD$_3$OD): δ 7.68 (m, 1H), 7.41 (m, 2H), 7.29 (m, 2H), 7.23-7.10 (m, 7H), 4.28 (br, 2H), 2.36 (s, 3H). LC/MS: m/z=400.2 [M+H]$^+$ (Calc: 399.4).

1-(4-(4-Fluorophenoxy)phenyl)-2-(2-(piperidin-1-yl)ethyl)-1H-benzo[d]imidazole (Compound 17): $^1$H NMR (400 MHz, CD$_3$OD): δ 7.66 (m, 1H), 7.48 (m, 2H), 7.33-7.12 (m, 9H), 3.03 (m, 2H), 2.79 (m, 2H), 2.41 (br, 4H), 1.57 (m, 4H), 1.45 (m, 2H). LC/MS: m/z=416.2 [M+H]$^+$ (Calc: 415.5).

tert-Butyl (S)-2-(1-(4-(4-fluorophenoxy)phenyl)-1H-benzo[d]imidazol-2-yl)pyrrolidine-1-carboxylate (Compound 18): LC/MS: m/z=47.2 [M+H]$^+$ (Calc: 473.5).

tert-Butyl 4-(1-(4-(4-fluorophenoxy)phenyl)-1H-benzo[d]imidazol-2-yl)piperidine-1-carboxylate (Compound 19): LC/MS: m/z=488.4 [M+H]$^+$ (Calc: 487.6).

Example 4

Synthesis of 1-(4-(4-fluorophenoxy)phenyl)-2-(piperidin-4-yl)-1H-benzo[d]imidazole (Compound 20)

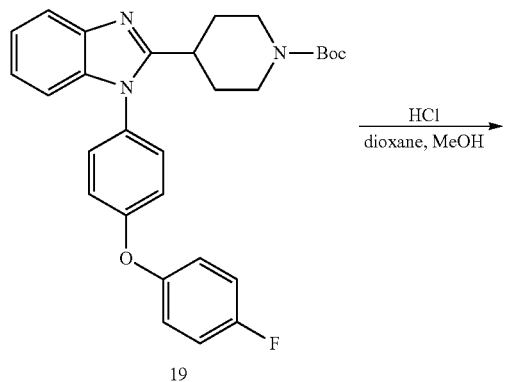

To a solution of Compound 19 (300 mg, 0.61 mmol) in MeOH (4 mL) was added 4N HCl in dioxane (4 mL, 16 mmol), the mixture stirred at RT for 2 h and concentrated. The crude Compound 20 was used without further purification. LC/MS: m/z=388.3 [M+H]$^+$ (Calc: 387.5).

In a similar manner, the following compound was prepared:

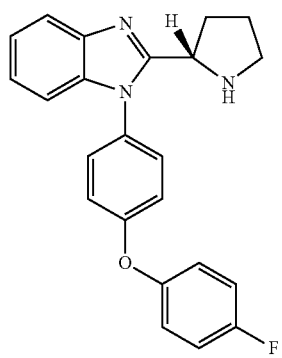

(S)-1-(4-(4-fluorophenoxy)phenyl)-2-(pyrrolidin-2-yl)-1H-benzo[d]imidazole (Compound 21): LC/MS: m/z=374.2 [M+H]$^+$ (Calc: 373.4).

Example 5

2-(4-(1-(4-(4-Fluorophenoxy)phenyl)-1H-benzo[d]imidazol-2-yl)piperidin-1-yl)acetamide (Compound 23)

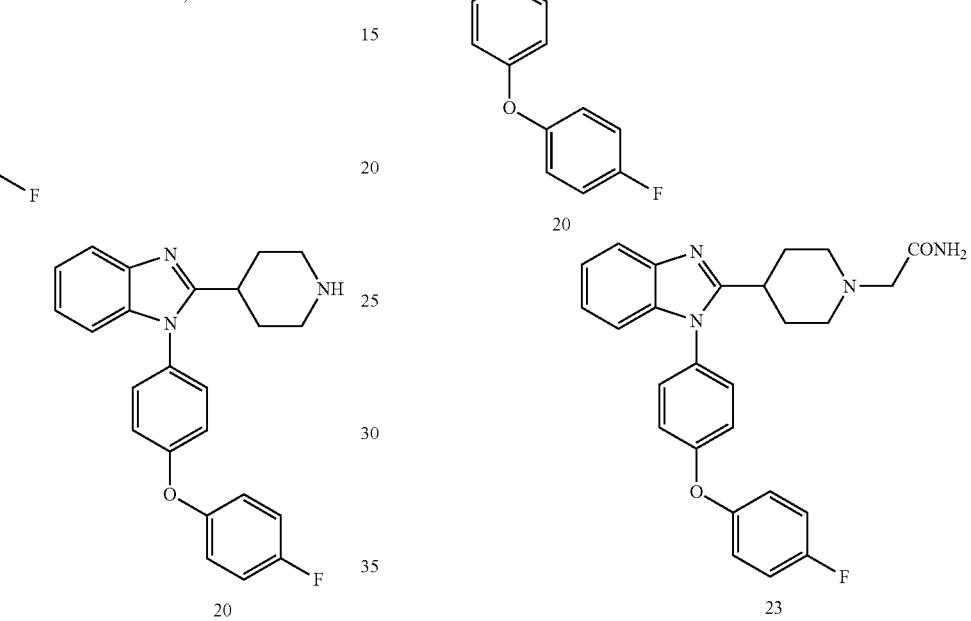

A mixture of Compound 20 (155 mg, 0.4 mmol) and Compound 22 (83 mg, 0.6 mmol) in DMF (4 mL) was stirred at 70 C for 2 h. The reaction mixture was cooled to RT, concentrated and the residue purified by flash chromatography (SiO$_2$, 10% (10% NH$_4$OH in MeOH) in DCM) to give Compound 23 (100 mg, 56% yield). $^1$H NMR (400 MHz, CD$_3$OD): δ 7.70 (d, J=8 Hz, 1H), 7.45 (m, 2H), 7.34-7.18 (m, 8H), 7.10 (m, 1H), 2.98 (m, 4H), 2.79 (m, 1H), 2.15 (m, 4H), 1.90 (m, 2H). LC/MS: m/z=445.2 [M+H]$^+$ (Calc: 444.5).

In a similar manner, the following compounds were prepared:

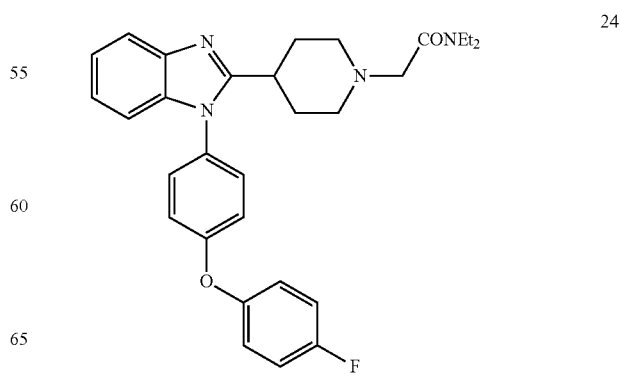

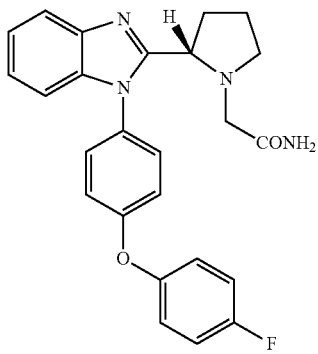

N,N-diethyl-2-(4-(1-(4-(4-fluorophenoxy)phenyl)-1H-benzo[d]imidazol-2-yl)piperidin-1-yl)acetamide (Compound 24): $^1$H NMR (400 MHz, CD$_3$OD): δ 7.57 (m, 1H), 7.33 (m, 2H), 7.21-7.05 (m, 8H), 6.99 (m, 1H), 3.39 (m, 2H), 3.27 (m, 2H), 3.09 (s, 2H), 2.87 (m, 2H), 2.70 (m, 1H), 1.97 (m, 4H), 1.79 (m, 2H), 1.15 (m, 3H), 1.01 (m, 3H). LC/MS: m/z=501.3 [M+H]$^+$ (Calc: 500.6).

(S)-2-(2-(1-(4-(4-fluorophenoxy)phenyl)-1H-benzo[d]imidazol-2-yl)pyrrolidin-1-yl)acetamide (Compound 25): $^1$H NMR (400 MHz, CD$_3$OD): δ 7.61 (m, 1H), 7.33 (m, 2H), 7.26-7.05 (m, 8H), 7.01 (m, 1H), 3.75 (m, 1H), 3.16 (m, 2H), 2.77 (m, 1H), 2.34 (m, 1H), 2.15-1.87 (m, 3H), 1.78 (m, 1H). LC/MS: m/z=431.3 [M+H]$^+$ (Calc: 430.5).

Example 6

In similar manners as those delineated in EXAMPLES 1-5, the following compounds were prepared:

2-((1-(1-(4-(4-(Trifluoromethyl)-phenoxy)phenyl)-1H-benzo[d]imidazol-2-yl)ethyl)amino)acetamide (Compound 27): LC/MS: m/z=455.1 [M+H]$^+$ (Calc: 454.2).

3-Hydroxy-2-(((1-(4-(4-(trifluoro-methyl)phenoxy)phenyl)-1H-benzo-[d]imidazol-2-yl)methyl)amino)propanamide (Compound 30): LC/MS: m/z=471.1 [M+H]$^+$ (Calc: 470.2).

1-((1-(4-(4-(Trifluoromethyl)phenoxy)phenyl)-1H-benzo[d]imidazol-2-yl)methyl)pyrrolidine-2-carboxamide (Compound 33): LC/MS: m/z=481.2 [M+H]$^+$ (Calc: 480.2).

5-Oxo-1-((1-(4-(4-(trifluoromethyl)phenoxy)phenyl)-1H-benzo[d]imidazol-2-yl)methyl)-pyrrolidine-2-carboxylic acid (Compound 42): LC/MS: m/z=496.0 [M+H]$^+$ (Calc: 495.1).

5-Oxo-1-((1-(4-(4-(trifluoro-methyl)phenoxy)phenyl)-1H-benzo[d]imidazol-2-yl)methyl)-pyrrolidine-2-carboxamide (Compound 43): LC/MS: m/z=495.1 [M+H]$^+$ (Calc: 494.2).

Likewise, Compound Nos. 26, 28, 29, 31, 32, and 34 to 41 can be similarly prepared.

Example 7

Representative compounds of the invention have been tested in the FLIPR® or FLIPR$^{TETRA}$® sodium dye assay with KCl assay for sodium channel blocking activity, which is described in detail above. Representative values are presented in TABLE 3.

TABLE 3

Evaluation of compounds as sodium channel (Na$_v$) blockers

| Compound No. | Na$_v$1.7 Activity (μM) FLIPR assay IC$_{50}$ (μM) ± SEM |
|---|---|
| 9 | 0.630 ± 0.050 |
| 10 | 0.313 ± 0.032 |
| 11 | 0.102 ± 0.022 |
| 14 | 0.571 ± 0.070 |
| 16 | 0.957 ± 0.092 |
| 17 | 0.081 ± 0.009 |
| 15 | >20 |
| 24 | 0.516 ± 0.029 |
| 23 | 1.493 ± 0.225 |
| 25 | 1.221 ± 0.035 |

Having now fully described this invention, it will be understood by those of ordinary skill in the art that the same can be performed within a wide and equivalent range of conditions, formulations and other parameters without affecting the scope of the invention or any embodiment thereof.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

All patents and publications cited herein are fully incorporated by reference herein in their entirety.

We claim:

1. The compound of Formula V, or a pharmaceutically acceptable salt, or diastereomer thereof:

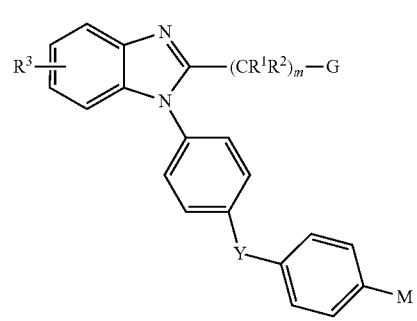

Formula V

Wherein
Y is —O—;
m is 0, 1, or 2;
M is halogen, haloalkyl, haloalkoxy, (alkyl)amino, amino, or (dialkyl)amino;
R$^1$ and R$^2$, each independently, are H or (C$_{1-3}$)alkyl;
R$^3$ is H, (C$_{1-3}$)alkyl, (C$_{1-3}$)alkoxy, amino, hydroxyl, or halogen;
G is
  piperidinyl optionally substituted by one or more substituents independently selected from the group consisting of
  a) —(C$_{0-3}$)alkyl-C(O)N(R$^7$)$_2$ further optionally substituted by one or more substituents independently selected from the group consisting of (C$_{1-3}$)alkyl, —(C$_{0-3}$)alkyl-OH, —(C$_{1-3}$)alkoxy, —(C$_{0-3}$) alkyl-C(O)OH, —(C$_{0-3}$)alkyl-S(O)$_2$NH$_2$, and —(C$_{0-3}$) alkyl-C(O)NH$_2$;

b) (C$_{1-3}$)alkyl optionally substituted by one or more substituents independently selected from the group consisting of (C$_{1-3}$)alkyl, hydroxyl, —NH$_2$, —(C$_{0-3}$)alkyl-OH, halogen, —(C$_{0-3}$)alkyl-C(O)OH, and —(C$_{0-3}$)alkyl-C(O)N(R$^7$)$_2$;
c) (C$_{1-3}$)alkoxy optionally substituted by one or more same or different halogens;
d) halogen;
e) —S(O)$_2$(C$_{1-3}$)alkyl;
f) —C(O)O(C$_{1-3}$)alkyl; and
g) —C(O)(C$_{1-3}$)alkyl;
and, R$^7$ independently is H or (C$_{1-3}$)alkyl.

2. The compound of claim 1, wherein M is halogen or haloalkyl.

3. The compound of claim 1, wherein one of R$^1$ and R$^2$ is H, and the other is (C$_{1-3}$)alkyl.

4. The compound of claim 1, wherein G is piperidinyl that is

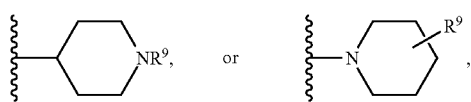

wherein R$^9$ is H, —(C$_{1-3}$)alkyl-C(O)NH$_2$, —C$_{(1-3)}$alkyl-C(O)N((C$_{1-3}$)alkyl)$_2$, C(O)NH$_2$, —C(O)(C$_{1-3}$)alkyl, C(O)O(C1-3)alkyl, —S(O)$_2$(C$_{1-3}$)alkyl, (C$_{1-3}$)alkyl, or halogen.

5. The compound of claim 1, wherein said compound is selected from the group consisting of:
1-(4-(4-Fluorophenoxy)phenyl)-2-(2-(piperidin-1-yl)ethyl)-1H-benzo[d]imidazole (Compound 17);
tert-Butyl 4-(1-(4-(4-fluorophenoxy)phenyl)-1H-benzo[d]imidazol-2-yl)piperidine-1-carboxylate (Compound 19);
1-(4-(4-Fluorophenoxy)phenyl)-2-(piperidin-4-yl)-1H-benzo[d]imidazole (Compound 20);
2-(4-(1-(4-(4-Fluorophenoxy)phenyl)-1H-benzo[d]imidazol-2-yl)piperidin-1-yl)acetamide (Compound 23); and
N,N-diethyl-2-(4-(1-(4-(4-fluorophenoxy)phenyl)-1H-benzo[d]imidazol-2-yl)piperidin-1-yl)acetamide (Compound 24);
and pharmaceutically acceptable salts, solvates, hydrates, and diastereomers thereof.

6. A pharmaceutical composition comprising the compound of claim 1 and a pharmaceutically acceptable carrier or diluent.

7. A method for treating pain in a mammal identified as in need thereof, comprising administering to said mammal an effective amount of a compound of claim 1.

8. A method of modulating Nav1.7 sodium channel in a mammal, comprising administering to the mammal at least one compound of claim 1.

9. The compound of claim 4, wherein G is

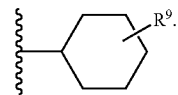

10. The compound of claim 4, wherein G is

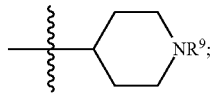

and
R$^9$ is H, —C$_{(1-3)}$alkyl-C(O)NH$_2$, —C$_{(1-3)}$alkyl-C(O)N((C$_{1-3}$)alkyl)$_2$, or C(O)O(C1-3)alkyl.

* * * * *